US011299520B2

(12) United States Patent
Vedantam et al.

(10) Patent No.: US 11,299,520 B2
(45) Date of Patent: Apr. 12, 2022

(54) COMPOSITIONS COMPRISING A CHIMERIC BACTERIAL SURFACE LAYER PROTEIN AND METHODS OF USE THEREOF

(71) Applicant: Arizona Board of Regents on Behalf of the University of Arizona, Tucson, AZ (US)

(72) Inventors: Gayatri Vedantam, Tucson, AZ (US); Virinchipuram Viswanathan, Tucson, AZ (US)

(73) Assignee: Arizona Board of Regents on Behalf of the University of Arizona, Tucson, AZ (US)

( * ) Notice: Subject to any disclaimer, the term of this patent is extended or adjusted under 35 U.S.C. 154(b) by 0 days.

(21) Appl. No.: 16/651,160

(22) PCT Filed: Sep. 25, 2018

(86) PCT No.: PCT/US2018/052656
§ 371 (c)(1),
(2) Date: Mar. 26, 2020

(87) PCT Pub. No.: WO2019/067447
PCT Pub. Date: Apr. 4, 2019

(65) Prior Publication Data

US 2020/0239527 A1 Jul. 30, 2020

Related U.S. Application Data

(60) Provisional application No. 62/563,365, filed on Sep. 26, 2017.

(51) Int. Cl.

| | |
|---|---|
| *A61K 35/74* | (2015.01) |
| *C07K 14/33* | (2006.01) |
| *C07K 14/335* | (2006.01) |
| *C12N 9/90* | (2006.01) |
| *C12N 15/62* | (2006.01) |
| *A61K 9/00* | (2006.01) |
| *A61K 38/00* | (2006.01) |

(52) U.S. Cl.
CPC ............ *C07K 14/33* (2013.01); *C07K 14/335* (2013.01); *C12N 9/90* (2013.01); *C12N 15/62* (2013.01); *A61K 9/0053* (2013.01); *A61K 38/00* (2013.01)

(58) Field of Classification Search
CPC ...................................................... A61K 39/00
USPC ..... 424/9.1, 9.2, 184.1, 185.1, 234.1, 247.1; 536/23.1, 23.7
See application file for complete search history.

(56) References Cited

U.S. PATENT DOCUMENTS

2005/0233408 A1 10/2005 Pouwels et al.

FOREIGN PATENT DOCUMENTS

WO 2016/118900 A1 7/2016
WO WO2016118900 * 7/2016 ............ A61K 39/08

OTHER PUBLICATIONS

Duong et al. Construction of vectors for inducible and constitutive gene expression in Lactobacillus. Microb Biotechnol, May 2011, vol. 4, No. 3, pp. 357-367.
International Search Report and Written Opinion, International Application No. PCT/US2018/052656, dated Mar. 22, 2019, 15 pages.

* cited by examiner

*Primary Examiner* — Jennifer E Graser
(74) *Attorney, Agent, or Firm* — Casimir Jones, S.C.; J. Mitchell Jones

(57) ABSTRACT

The invention features engineered probiotic lacto acid bacteria (LAB) expressing a chimeric *Clostridium difficile/Lactobacillus acidophilus* SlpA, or fragment thereof, and its use for the treatment or prevention of *Clostridium difficile* infection and gut colonization.

9 Claims, 18 Drawing Sheets

Specification includes a Sequence Listing.

Fig. 1 (Part 1/3)

SlpA-CHIMERA-EXPRESSING PLASMID (pMGM15)
pb 1 – pb 7740 (SEQ ID NO: 1)

```
   1 TACTAGTCTC TTTTTTCTTT AGATTAAAAT AACAAACTTA AAGTGCGAAA
  51 AAGGATATTT TTAACGTTGT ATAAAATTGC GTCTTGATGT TATTATCAGT
 101 GTATAAGCTT CTAGAGCGGC CGCGAAGATC TTTA?????? AAAGT?????
 151 ACCTTAACGT AAGTCTTGTC AGTGTTGTCA CGGATCTTGT AGTACTTTTG
 201 GCCGTTCTTG AAGGGTAAG AAGCACCGTA AGTAGTTACA ACTTCACCCT
 251 TCTTCAAATGC AACCTTTTGA GCACGTATGC TTCATGATGC GTAAGCTTA
 301 GCGTTGTGCT TCAAAGTACG CTTACGTCCA TCAGTGTTTG CAGGGGTGAT
 351 GTACTTGTCA ACAGCCTTAC CGTTTTCAAC TACTTGGGTAG GAAGTCTAAC
 401 GGTTGATAGT AGTAGTGTTT GGCAATACGC TTACTGAGCT GTAACGCTTA
 451 ACGGTGTCAG TACCAACACG CTTAGCGTCC TTGTCGGAGT AGTAGGCGTT
 501 GTGCATAATT CGCTGGCGTA CGCTGGCTAC AGTTGGCTCA GCAACAGTAG
 551 GAACAGTAGC AACTACTGGG AAATAGCCTG ACTTACCAGT AGTATTTGAT
 601 GCTAAATCTG TATCATCTTT AGTCACAAAC CGACTTACGG GAACTGCACT
 651 CGGTGTACTA CCACCAGTTA CATCAACTTT AAGGGTTTTG TTGAAATCAA
 701 TAGTTGTTCC TTTGCCTTCA TATTCTAAAC CTGTTGATGG AAGATTGATT
 751 GCAATACCAG CTGTAGAATC ACCTACTTTA CCTATCTTAT CTTCAACAGC
 801 ACCGGCTTTC ATTTGGCAA CATATCCCGT ATCTTGACTA CCTCCACTCT
 851 TTAAGCCAAA AGTTGCCACA TCTTTTACTT TTAAGCCTTT TGTTGCCACA
 901 ACATTCTTTC CTCAGAATC CTGCTTTTA GCACCATTC CAAACTATC
 951 TTTAGTTGCA ATATCAATTA GCCGTCTTTC ATTTAACGAA TTCAATTGAG
1001 TAACAATAGC TTGGCCATCG CCTTGATTGG TGATAATCTT ATTCTCTAGA
1051 TTGTAATCAA CAGAAAAATC TACATAATCG CCATCGGCTA ATTTGTCTAA
1101 TTGTGTATTT ACAAGATTAT ACAACTTTTC TTGGGCTGCA TCTCGATCTG
1151 CTTTCTATT CGTTGATTTA GGTGCTACTT CTCCTACCAC ACCATCATTG
1201 AAACTGACCG TAATTTACC AATACTATTA TCTTTAAGTC CATCTTGTAA
1251 TTGTTTGACA GCCTTTTTCC AATCATTCTT AACCACCGTA TACCCTGTG
1301 TACCAGTGTT TGCAGCAAAT ACAGGTGCAG CAGGCTAAC AGTAGATACA
1351 GCAGAAGCAG CAACTGGAGC AACGGCAAGT AAAGCAGCAG CAGCAGCGCT
1401 AACGATTCTT AAATTTTCT T??GGATCC ATATGCACGT CGACGCC???
1451 ??GAAGCTT CGAATTCT?? ?????????? ?????????? ??????????
1501 ?????????? ?????????? ?????????? ?????????? ??????????
1551 TTGACGTG ACGGTTAAG ACTATTTTG ACATGAAATA TCTC????
1601 ???????GT TTCTCGATC TTTTACGAT TTCAGCTTT TTTTGATGG
1651 ?????????? ?????????? ???????TA AGAGAAGTGT AAAAATCATG
1701 ?????????? ?????????? ?????????? ?????????? ??????????
1751 AAAAACAAAA AGAAATATTT TGTAGTTGCG TTTGTCGTAG TTTATTACTT
1801 GTCGCACCAG GGCAGCAGC GATAGATCTC TAATAAATGG CGTAATTGAG
1851 CAGCTGAAAT AATTACTAAT AAGAATAATT CAACAATAAT TTTAAACATA
1901 TTCGCTACT TTCCTTATAT ACTTGTTCTA ATTATACAAG TAGAGCCGTA
1951 TTTGCACAAA TAACAAAAAG AGTATGAGCA AAAACTCATA CTCTTTTTGT
2001 TATTTAGCAA TTGCTACCAC TCGTTTTTCA CGGATAACGG TAATCTTAAT
2051 ACGACCTGCA GGCGGCCGCG AATTCACTAG TGATATCTGA AGATCCAGC
2101 TGGGTGAGCG GGATCTTT?? ACATAATAGG TAATACCTTT ACTGCATCTT
2151 TAACATTGCT ATAAGTCTTT AATGAACTGA AATTTGCATC TAACTTATTC
2201 ATCTTCATAG CTAATTCAGG CTTAATACCA GTAATGATCA ATCTGTGCC
2251 AGTTAACTTT AGTAGGTGCA TTAACTTAAA GATTTGCGT ACGCGTTTGT
2301 CATTGACTTG TGCAAGACCG CTAGATCAA TAATCAAGTA ATCATCTTTT
2351 GAAGTAGAAA GGATATTAGT TAACGTACAA ACAATACTGT TAAATCTCTC
2401 TTCAGTAAGA TTGCCAACTA GTGGTAACGC TGATATGCCG TTTCTTATAG
2451 GTACAATTGG TGTAGATAAA GCAGTAATCT CTGTTAATGA ATCTTCCAAT
2501 AACTTTTCAT ATTCTTTTG CTTCGTAATA TCATTTGAA TACCAACAAA
2551 GTATGTTTTA TCTTCAATTT CCATAGGATC TATATTCAAT TCGTTCCAAA
2601 ACATAGTTCC GTCTTTTTG TAATTCTGAA TTTGTACTGT GACTGGTTCT
2651 TTATTCTGTA AAGCGGTACG GTGTTATCA ACTTCAGCCG GGTCGGTATG
2701 TTTACCTTGC AAAAAGCGTG CGTTTTTCC AAGAATCTCT TGAACGAATC
2751 TGGCATTTTT CCCAAGAATT TCTTCGGTTT CATAACCAGT CATTTGTACA
```

CLOSTRIDIUM DIFFICILE / L. ACIDOPHILUS SLPA CHIMERA. L. acidophilus sequence in dark red, C. difficile sequence in pink. Start and stop codons underlined with wavy lines CONSTITUTIVE PROMOTER FROM L. ACIDOPHILUS pgm GENE; RIBOSOME-BINDING SITE UNDERLINED YTVA FLOURESCENT ALLELE FROM B. SUBTILIS. Start and stop codons underlined with wavy lines

Fig. 1 (Continued – Part 2/3)

```
2801 AAACCTTGAT TAACATAAAC AATTGGATTA TCTTCCAAAG CTGGATCAGT
2851 AATCACGACT CCAACACGAA CATGATCTAA TGCTTTTTTG ATTACTTCTA
2901 ATTGTCCTGG AATACCAAAT GATTGAAAAG ATGCCATATA AATCCCCCTT
2951 AGGCCGTCAG CTTGCTATGC GAAAGCCTGA TATTCCCCTT TTTAAAAATG
3001 AATTCTACAG TAACCGTAGC ACAACACATG TTCTGATTCA AGCAAGTGCA
3051 GTTTGTTGTT TGTCATTAGG GCTTGTCCTC AGTTTAAACA ATCACTCCTT
3101 CTTAATTACA AATTTTTACG ATCTAATTTA ACTTCAATTC CTATTATACA
3151 AAATTTTAAG ATACTCCACT ATCAACACAC TCTTAAGTTT GCTTCTAAGT
3201 CTTATTTCCA TAACTTCTTT TACGTTTCCG CCATTCTTTG CTGTTTCGAT
3251 TTTTATGATA TGGTGCAAGT CAGCACGAAC ACGAACCGTC TTATCTCCCA
3301 TTATATCTTT TTTTGCACTG ATTGGTGTAT CATTTCGTTT TTCTTTTGCG
3351 CGACTCTAGA GGATCCTGAT AAATATGAAC ATGATGAGTG ATCGTTAAAT
3401 TTATACTGCA ATCGGATGCG ATTATTGAAT AAAAGATATG AGAGATTTAT
3451 CTAATTTCTT TTTTCTTGTA AAAAAAGAAA GTTCTTAAAG GTTTATAGT
3501 TTTGTCGTA GAGCACACGG TTTAACGACT TAATTACGAA GTAAATAAGT
3551 CTAGTGTGTT AGACTTTATG AAATCTATAT ACGTTATAT ATATTTATTA
3601 TCCGATTTTT TATTAAAACG TCTCAAAATC GTTTCTGAGA CGTTTTAGCG
3651 TTTATTTCGT TTAGTTATCG GCATAATCGT TAAAACAGGC GTTATCGTAG
3701 CGTAAAAGCC CTTGAGCGTA GCGTGGCTTT GCAGCGAAGA TGTTGTCTGT
3751 TAGATTATGA AAGCCGATGA CTGAATGAAA TAATAAGCGC AGCGCCCTTC
3801 TATTTCGGTT GGAGGGAGCT CAAGGGAGTA TGAGGGAATG AAATTCCCTC
3851 ATCGGTTTGA TTTTAAAAAT TGCTTGCAAT TTTGCCGAGC GGTAGCGCTG
3901 GAAAATTTTT GAAAAAAATT TGGAATTTGG AAAAAAATGG GGGGAAAGGA
3951 AGCGAATTTT GCTTCCGTAC TACGACCCCC CATTAAGTGC CGAGTGCCAA
4001 TTTTTGTGCC AAAAACGCTC TATCCCAACT GGCTCAAGGG TTTAAGGGGT
4051 TTTTCAATCG CCAACGAATC GCCAACGTTT TCGCCAACGT TTTTTATAAA
4101 TCTATATTTA AGTAGCTTTA TTGTTGTTTT TATGATTACA AAGTGATACA
4151 CTAACTTTAT AAAATTATTT GATTGGAGTT TTTTAAATGG TGATTTCAGA
4201 ATCGAAAAAA AGAGTTATGA TTTCTCTGAC AAAAGAGCAA GATAAAAAAT
4251 TAACAGATAT GGCGAAACAA AAAGTTTTTT CAAAATCTGC GGTTGCGGCG
4301 TTAGCTATAG AAGAATATGC AAGAAAGGAA TCAGAACAAA AAAAATAAGC
4351 GAAAGCTCGC GTTTTTAGAA GGATACGAGT TTTCGCTACT TGTTTTTGAT
4401 AAGGTAATTA TATCATGGCT ATTAAAAATA CTAAAGCTAG AAATTTTGGA
4451 TTTTTATTAT ATCCTGACTC AATTCCTAAT GATTGGAAAG AAAAATTAGA
4501 GAGTTTGGGC GTATCTATGC CTGTCAGTCC TTTACACGAT ATGGACGAAA
4551 AAAAAGATAA AGATACATCG AATAATAGTA ATATTATACA AAATGGAAGA
4601 CACTATAAAA AACCACACTA TCACGTTATA TATATTGCAC GAAATCCTGT
4651 AACAATAGAA AGCGTTAGGA ACAAGATTAA GCGAAAATTG GGGAATAGTT
4701 CAGTTGCTCA TGTTGAGATA CTTGATTATA TCAAAGGTTC ATATGAATAT
4751 TTGACTCATG AATCAAAGGA CGCCTATTCT AAGAATAAAC ATATATACGA
4801 CAAAAAAGAT ATTTTGAACA TTAATGATTT TGATATTGAC CGGTATATAA
4851 CACTTGATGA AAGCCAAAAA AGAGAATTGA AGATTTACT TTTAGATATA
4901 GTGGATGCT ATAATTTCGT AAATACAAAA GATTAATGG CTTTATTCG
4951 CCTTAGGGGA GCGGAGTTTG GAATTTTAAA TACGAATGAT GTAAAGATA
5001 TTGTTTCAAC AAACTCTAGC GCCTTTAGAT TATGGTTTGA GGGCAATTAT
5051 CAGTGTGGAT ATAGACCAAG TTATCCAAAG GTTCTTGATG CTGAAACGGG
5101 GGAAATAAAA TGGCAAACAA AGAAAAAGAG TTATTTGCTG AAAATGAGGA
5151 ATTAAAAAAA GAAATTAAGG ACTTAAAAGA GCGTATTGAA AGATACAGAG
5201 AAATGGAAGT TGAATTAAGT ACAACAATAG ATTTATTGAG AGGAGGGATT
5251 ATTGAATAAA TAAAAGCCCC CTGACGAAAG TCGAAGGGGG TTTTTATTTT
5301 GGTTTGATGT TGCGAATAAT AGCAATAACA TTGCAATAAT CAAAATGATC
5351 TTCCTTCAGG TTATGACCAT CTGTGCCAGT TCGTAATGTC TGGTCAACTT
5401 TCCGACTCTG AGAAACTTCT GGAATCGCTA GAGAATTTCT GGAATGGGAT
5451 TCAGGAGTGG ACAGAACGAC ACGGATATAT AGTGGATGTG TCAAAACGCA
5501 TACCATTTTG AACGATGACC TCTAATAATT GTAATCATG TTGGTTACGT
5551 ATTTATTAAC TTCTCCTAGT ATTAGTAATT ATCATGGCTG TCATGGCGCA
5601 TTAACGGAAT AAAGGGTGTG CTTAAATCGG GCCATTTTGC GTAATAAGAA
5651 AAAGGATTAA TTATGAGCGA ATTGAATTAA TAATAAGGTA ATAGATTTAC
5701 ATTAGAAAAT GAAAGGGGAT TTTATGCGTG AGAATGTTAC AGTCTATCCC
5751 TGCCGAAAGG GGGATGTGCT GCAAGGCGAT TAAGTTGGGT AACGCCAGGG
5801 TTTTCCCAGT CACGACGTTG TAAAACGACG GCCAGTGAGC GCGCGTAATA
```

TEMPERATURE-SENSITIVE REPA GENE TO FORCE PLASMID INTEGRATION INTO GENOME. Start and stop codons underlined with wavy lines Fig. 1 (Continued – Part 3/3)

```
5851 CGACTCACTA TAGGGCGAAT TGGGTACCGG GCCCCCCCTC GAGGTCGACG
5901 GTATCGATAA GCTTTTTAGA CATCTAAATC TAGGTACTAA AACAATTCAT
5951 CCAGTAAAAT ATAATATTTC CTGCAGGGCC AGTGGGCAAG TTGAAAAATT
6001 CACAAAAATG TGGTATAATA TCTTTGTTCA TTAGACGGAT AAACTTGAAT
6051 TTGAGAGGGA ACTTAGATGG TATTTGAAAA AATTGATAAA AATAGTTGGA
6101 ACAGAAAACA GTATTTTGAC CACTACTTTG CAAGTGTACC TTGTACCTAC
6151 AGCATGACCG TTAAAGTGGA TATCACACAA ATAAAGGAAA AGGGAATGAA
6201 ACTATATCCT GCAATGCTTT ATTATATTGC AATGATTGTA AACCGCCATT
6251 CAGAGTTTAG GACGGCAATC AATCAAGATG GTGAATTGGG GATATATGAT
6301 GAGATGATAC CAAGCTATAC AATATTTCAC AATGATACTG AAACATTTTC
6351 CAGCCTTTGG ACTGAGTGTA AGTCTGACTT TAAATCATTT TTAGCAGATT
6401 ATGAAGTGA TACGCAACGG TATGGAAACA ATCATAGAAT GGAAGGAAAG
6451 CCAAATGCTC CGGAAAACAT TTTAATGTA TCTATGATAC CGTGGTCAAC
6501 CTTCGATGCC TTTAATCTGA ATTCAGAA AGGATATGAT TATTTGATTC
6551 CTATTTTTAC TATGGGGAAA TATTATAAAG AAGATAACAA AATTATACTT
6601 CCTTTGGCAA TTCAAGTTCA TCACCACGTA TGTGACGGAT TTCACATTTG
6651 CCGTTTTGTA AACGAATTGC AGGAATTGAT AAATAGTTAA CTTCAGGTTT
6701 GTCTGTAACT AAAAACAAGT ATTTAAGCAA AAACATCGTA GAAATACGGT
6751 GTTTTTTGTT ACCCTAAGGC CGGCCGAATT GGGCCCGACG TCGCATGCTC
6801 CCGGCCGCCA TGGCGGCCGC GGGAATTCGA TATCACTAGT GAATTCGCGG
6851 CCGCCTGCAG GTCGACCATA TGGGAGAGCT CCCAACGCGT TGGATGCAT

6901 TACATTTCA ATTGATCA GAAGCTACC ATCTGCCTT TCCAATGGC
6951 GCCAATGCC ACCAAAACG TCGGCCAAAT TGCAGATTT TTTGGCAAG
7001 TTCTCACAT CAAGAAACG TCGATCAAAT TTTTGAATT CAGCTTGCTC
7051 AATTTTATTA AATCCGGAT CACTTTGCT TCGTAAACCA AAACAGTTCA
7101 TATCAGGCC AGTAGATTCA TCACGTTAA CCCAATTTTT AAATGCCCAC
7151 TCTTCCCAA TACGATTTTT ATGTCTAAT AAAAACGAA TATTAGTGTC
7201 CCCTGGAAG AACCATAGGA GTTGACTTTT AATTAGGCG GATACCGTCA
7251 AGCGTCGCA GTATGGAGCC GCGTAAACT GCTGAACAC ATCCCCAGCC
7301 TGGCGATGG TGTCACCACG ACTGGTAGCC CACGCCGCC ATTGCAGCC
7351 ATAAACCAAT CCTAAATCAC CGGATTTGCC TGCAAAGGAC TCGGCAGTGA
7401 GAAATGCTTC GTCAAACTTG GCCATCTGTT CACGATAACT GCGGGCAAAT
7451 TCAGGATCTT TCTGGCTGCC ATGACCAAAA TCGGTCATAT CCGGACCAAG
7501 ATAATCGGGG CTGGCAACCC ACTTCTCAAA GGGCCATTCA TCCCACGTGT
7551 GATTTTATC CTGCAATAGG AAACGATGT TGTGTCGCC ACGGAAGAAC
7601 CAAGTAACT CGCTTTAAT GAGCCAAAG GCACCTTT TGGTGTGAG
7651 TAAGGAAAC CCTTGCTAA GTCAAACGG CATTGGTGA CCAAAATAC
7701 TGTACGTGCC AGTATGCGTA CGATCAGGCT TGAAATGTA
```

CHLORAMPHENICOL RESISTANCE CASSETTE. Start and stop codons underlined with wavy lines

L. ACIDOPHILUS THYA FRAGMENT TO FACILITATE CAMPBELL INTEGRATION

L. CASEI THYA FRAGMENT TO FACILITATE CAMPBELL INTEGRATION

Amino acid translations of all pMGM15 coding regions:

*Clostridium difficile* – L. acidophilus SlpA chimera (SEQ ID NO: 9): 45.54kDa

```
MKKNLRIVSAAAAALLAVAPVAASAVSTVSAAAPVFAATTGTQGYTVVKN   50
DWKKAVKQLQDGLKDNSIGKITVSFNDGVVGEVAPKSANKKADRDAAAEK  100
LYNLVNTQLDKLGDGDYVDFSVDYNLENKIITNQADAEAIVTKLNSLNEK  150
TLIDIATKDTFGMVSKTQDSEGKNVAATKALVKDVATFGLKSGGSEDTG   200
YVVEMKAGAVEDKYGKVGDSTAGIAINLPSTGLEYAGKGTTIDFNKTLKV  250
DVTGGSTPSAVAVSGFVTKDDTDLASNTNGKSATLFVVTVPNVAEPTVA   300
SVSKRIMHNAYYYDKDAKRVGTDSVKRYNSVSVLPNTTTINGKTYYQVVE  350
NGKAVDKYINAANIDGTKRTLKHNAYVYASSKKRANKVVLKKGEVVTTYG  400
ASYTFKNGQKYYKIGDNTDKTYVKVANFR*
```

YtvA fluorescent protein (SEQ ID NO: 10): 30.03kDa

```
MASFQSFGIPGQLEVIKKALDHVRVGVVITDPALEDNPIVYVNQGFVQMT   50
GYETEEILGKNARFLQEILGKNARFLQGKHTDPAEVDNIRTALQNKEPVT  100
VQIQNYKKDGTMFWNELNIDPMEIEDKTYFVGIQNDITKQKEYEKLLEDS  150
LTEITALSTPIVPIRNGISALPLVGNLTEERFNSIVCTLTNILSTSKDDY  200
LIIDLSGLAQVNEQTADQIFKLSHLLKLTGTELIITGIKPELAMKMNKLD  250
ANFSSLKTYSNVKDAVKVLPIM*
```

RepA temperature-sensitive protein (SEQ ID NO: 11): 26.86kDa

```
MAIKNTKARNFGFLLYPDSIPNDWKEKLESLGVSMAVSPLHDMDEKKDKD   50
TWNNSNIIQNGKHYKKPHYHVIYIARNPVTIESVRNKIKRKLGNSSVAHV  100
EILDYIKGSYEYLTHESKDAIAKNKHIYDKKDILNINDFDIDRYITLDES  150
QKRELKNLLLDIVDDYNLVNTKDLMAFIRLRGAEFGILNTNDVKDIVSTN  200
SSAFRLWFEGNYQCGYRASYAKVLDAETGEIK*
```

Chloramphenicol acetyltransferase (SEQ ID NO: 12): 24.3kDa

```
MVFEKIDKNSWNRKEYFDHYFASVPCTYSMTVKVDITQIKEKGMKLYPAM   50
LYYIAMIVNRHSEFRTAINQDGELGIYDEMIPSYTIFHNDTETFSSLWTE  100
CKSDFKSFLADYESDTQRYGNNHRMEGKPNAPENIFNVSMIPWSTFDGFN  150
LNLQKGYDYLIPIFTMGKYYKEDNKIILPLAIQVHHAVCDGFHICRFVNE  200
LQELINS*
```

Fig. 3

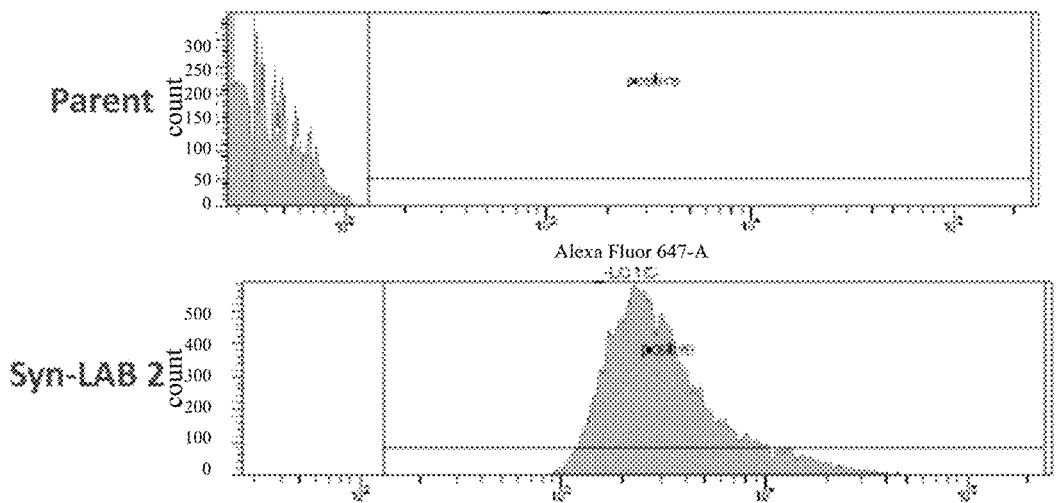
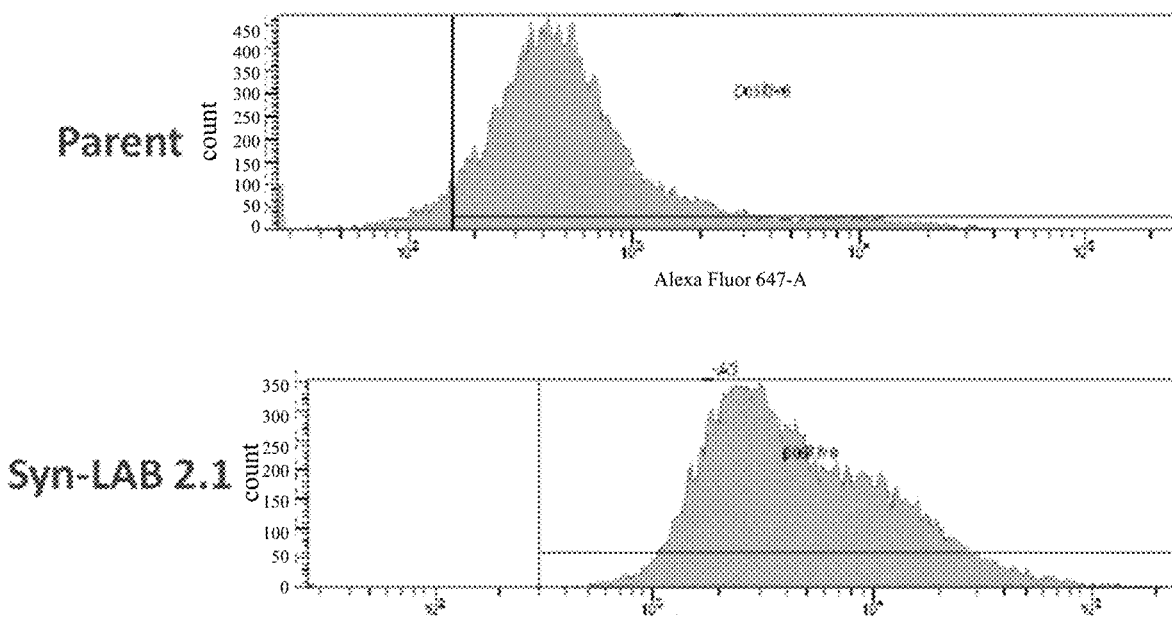
Fig. 6

SEQUENCE LISTING

```
<160> NUMBER OF SEQ ID NOS: 18

<210> SEQ ID NO 1
<211> LENGTH: 7740
<212> TYPE: DNA
<213> ORGANISM: Artificial Sequence
<220> FEATURE:
<223> OTHER INFORMATION: Artificially synthesized

<400> SEQUENCE: 1
tactagtctc ttttttcttt agattaaaat aacaaactta aagtgcgaaa aaggatattt      60
ttaacgttgt ataaaattgc gtcttgatgt tattatcagt gtataagctt ctagagcggc     120
cgcgaagatc tttattatct aaagtttgca accttaacgt aagtcttgtc agtgttgtca     180
ccgatcttgt agtactttg gccgttcttg aatgtgtatg aagcaccgta agtagttaca      240
acttcaccct tcttcaatac aaccttgtta gcacgcttct ttgatgatgc gtaaacgtaa     300
gcgttgtgct tcaaagtacg cttagtacca tcgatgtttg cagcgttgat gtacttgtca     360
acagccttac cgttttcaac tacttggtag taagtcttac cgttgatagt agtagtgttt     420
ggcaatacgc ttactgagtt gtaacgctta acgctgtcag taccaacacg cttagcgtcc     480
ttgtcgtagt agtatgcgtt gtgcataatt ctcttgctta cgctggctac agttggctca    540
gcaacattag gaacagtaac aactactggc aaagtagctg acttaccatt agtatttgat    600
gctaaatctg tatcatcttt agtcacaaac ccacttacgg caactgcact cggtgtacta    660
ccaccagtta catcaacttt aagggttttg ttgaaatcaa tagttgttcc tttgcctgca    720
tattctaaac ctgttgatgg aagattgatt gcaataccag ctgtagaatc acctacttta    780
ccatacttat cttcaacagc acccgctttc atttcgacaa catatccggt atcttcacta    840
cctccactct ttaagccaaa agttgccaca tcttttactt ttaacgcttt tgttgccgca    900
acattctttc cttcagaatc ctgcgtttta gacaccattc caaacgtatc tttagttgca    960
```

-continued

| | | |
|---|---|---|
| atatcaatta gcgtctttc atttaacgaa ttcaatttag taacaatagc ttcggcatcg | 1020 |
| gcttgattgg tgataatctt attctctaga ttgtaatcaa cagaaaaatc tacataatcg | 1080 |
| ccatcgccta atttgtctaa ttgtgtattt acaagattat acaacttttc tgcggctgca | 1140 |
| tctcgatctg ctttcttatt cgctgattta ggtgctactt ctcctaccac accatcattg | 1200 |
| aaactgaccg taatcttacc aatactatta tctttaagtc catcttgtaa ttgtttgaca | 1260 |
| gccttttcc aatcattctt aaccaccgta tagccttgtg taccagtggt tgcagcaaat | 1320 |
| acaggtgcag cagcgctaac agtagataca gcagaagcag caactggagc aacagcaagt | 1380 |
| aaagcagcag cagcagcgct aacgattctt aaattttct tcatggatcc atatgcacgt | 1440 |
| cgacgcgcct gcagaagctt cgaattctgc cttctgagct tcttcaacac cttttctga | 1500 |
| aaggttaacg tcaacccaac cagtaaattg gtttgaaagg ttccattcac tttgaccgtg | 1560 |
| acggattaaa actaattttg acatgaaata tctccttta aattcaatgt ttcatccata | 1620 |
| ttttacacat ttcacagttt ttttcataga gatatgggca aaaaacatc ttttttatt | 1680 |
| tctactttt attttctgct tttttgtgct aacttataac aagcatacta agagaagtgt | 1740 |
| aaaaatcatg aaaaacaaaa agaaatattt tgtagttgcg tttgtcgtag tttattactt | 1800 |
| gtcgcaccag ggcaggcagc gatagatctc taataaatgg cgtaattgag cagctgaaat | 1860 |
| aattactaat aagaataatt caacaataat tttaaacata ttcggctact ttccttatat | 1920 |
| acttgttcta attatacaag tagagcggta tttgcacaaa taacaaaaag gtatgagca | 1980 |
| aaaactcata ctcttttgt tatttagcaa ttgctaccac tcgttttca cggataacgg | 2040 |
| taatcttaat acgacctgca ggcggccgcg aattcactag tgatatctga agatccagc | 2100 |
| tgggtgagcg ggatctttt acataatagg taatacctt actgcatctt taacattgct | 2160 |
| ataagtcttt aatgaactga aatttgcatc taacttattc atcttcatag ctaattcagg | 2220 |
| cttaatacca gtaatgatca attctgtgcc agttaacttt agtaggtgac ttaacttaaa | 2280 |
| gatttgatca gcagtttgtt cattcacttg tgcaagaccg ctaagatcaa taatcaagta | 2340 |
| atcatctttt gaagtagaaa ggatattagt taacgtacaa acaatactgt taaatctctc | 2400 |
| ttcagtaaga ttgccaacta gtggtaacgc tgatatgccg tttcttatag gtacaattgg | 2460 |
| tgtagataaa gcagtaatct ctgttaatga atcttccaat aacttttcat attctttttg | 2520 |
| cttcgtaata tcattttgaa taccaacaaa gtatgtttta tcttcaattt ccataggatc | 2580 |
| tatattcaat tcgttccaaa acatagttcc gtctttttg taattctgaa tttgtactgt | 2640 |
| gactggttct ttattctgta aagcggtacg gatgttatca acttcagccg ggtcggtatg | 2700 |
| tttaccttgc aaaaagcgtg cgtttttcc aagaatctct tgaaggaatc tggcattttt | 2760 |
| cccaagaatt tcttcggttt cataaccagt catttgtaca aaaccttgat taacataaac | 2820 |
| aattggatta tcttccaaag ctggatcagt aatcacgact ccaacacgaa catgatctaa | 2880 |
| tgcttttttg attacttcta attgtcctgg aataccaaat gattgaaaag atgccatata | 2940 |
| aatcccctt aggccgtcag cttgctatgc gaaagcctga tattcccctt tttaaaaatg | 3000 |
| aattctacag taaccgtagc acaacacatg ttctgattca agcaagtgca gtttgttgtt | 3060 |
| tgtcattagg gcttgtcctc agtttaaaca atcactcctt cttaattaca aattttagc | 3120 |
| atctaattta acttcaattc ctattataca aaattttaag atactgcact atcaacacac | 3180 |
| tcttaagttt gcttctaagt cttatttcca taacttcttt tacgtttccg ccattctttg | 3240 |
| ctgtttcgat ttttatgata tggtgcaagt cagcacgaac acgaaccgtc ttatctccca | 3300 |
| ttatatcttt ttttgcactg attggtgtat catttcgttt ttcttttgcg cgactctaga | 3360 |

```
ggatcctgat aaatatgaac atgatgagtg atcgttaaat ttatactgca atcggatgcg    3420
attattgaat aaaagatatg agagatttat ctaatttctt ttttcttgta aaaaagaaa     3480 gttcttaaag gttttatagt tttggtcgta gagcacacgg tttaacgact taattacgaa    3540
gtaaataagt ctagtgtgtt agactttatg aaatctatat acgtttatat atatttatta   3600
tccgattttt tattaaaacg tctcaaaatc gtttctgaga cgttttagcg tttatttcgt    3660
ttagttatcg gcataatcgt taaaacaggc gttatcgtag cgtaaaagcc cttgagcgta    3720
gcgtggcttt gcagcgaaga tgttgtctgt tagattatga aagccgatga ctgaatgaaa    3780
taataagcgc agcgcccttc tatttcggtt ggaggaggct caaggagta tgagggaatg     3840 aaattccctc atgggtttga ttttaaaaat tgcttgcaat tttgccgagc ggtagcgctg    3900
gaaaattttt gaaaaaaatt tggaatttgg aaaaaaatgg ggggaaagga agcgaatttt    3960
gcttccgtac tacgaccccc cattaagtgc cgagtgccaa ttttttgtgcc aaaaacgctc   4020 tatcccaact ggctcaaggg tttaaggggt tttcaatcg ccaacgaatc gccaacgttt     4080
tcgccaacgt tttttataaa tctatattta agtagcttta ttgttgtttt tatgattaca    4140
aagtgataca ctaactttat aaaattattt gattggagtt ttttaaatgg tgatttcaga    4200
atcgaaaaaa agagttatga tttctctgac aaaagagcaa gataaaaaat taacagatat    4260
ggcgaaacaa aaaggttttt caaaatctgc ggttgcggcg ttagctatag aagaatatgc    4320
aagaaaggaa tcagaacaaa aaaataagc gaaagctcgc gtttttagaa ggatacgagt     4380
tttcgctact tgttttgat aaggtaatta tatcatggct attaaaaata ctaaagctag     4440
aaattttgga tttttattat atcctgactc aattcctaat gattggaaag aaaaattaga    4500
gagtttgggc gtatctatgg ctgtcagtcc tttacacgat atggacgaaa aaaaagataa    4560
agatacatgg aataatagta atattataca aaatggaaag cactataaaa aaccacacta    4620
tcacgttata tatattgcac gaaatcctgt aacaatagaa agcgttagga acaagattaa    4680
gcgaaaattg gggaatagtt cagttgctca tgttgagata cttgattata tcaaaggttc    4740
atatgaatat ttgactcatg aatcaaagga cgctattgct aagaataaac atatatacga    4800
caaaaaagat attttgaaca ttaatgattt tgatattgac cgctatataa cacttgatga    4860
aagccaaaaa agagaattga agaatttact tttagatata gtggatgact ataatttggt    4920
aaatacaaaa gatttaatgg cttttattcg ccttagggga gcggagtttg gaattttaaa    4980
tacgaatgat gtaaaagata ttgtttcaac aaactctagc gcctttagat tatggtttga    5040
gggcaattat cagtgtggat atagagcaag ttatgcaaag gttcttgatg ctgaaacggg    5100
ggaaataaaa tgacaaacaa agaaaaagag ttatttgctg aaaatgagga attaaaaaaa    5160 gaattaagg acttaaaaga gcgtattgaa agatacagaa aatggaagt tgaattaagt     5220 acaacaatag atttattgag aggagggatt attgaataaa taaaagcccc ctgacgaaag    5280
tcgaaggggg tttttatttt ggtttgatgt tgcgattaat agcaatacaa ttgcaataaa    5340
caaaatgatc ttccttcagg ttatgaccat ctgtgccagt tcgtaatgtc tggtcaactt    5400
tccgactctg agaaacttct ggaatcgcta gagaatttct ggaatgggat tcaggagtgg    5460
acagaacgac acgatatat agtggatgtg tcaaaacgca taccattttg aacgatgacc     5520
tctaataatt gttaatcatg ttggttacgt atttattaac ttctcctagt attagtaatt    5580
atcatggctg tcatggcgca ttaacggaat aaagggtgtg cttaaatcgg gccattttgc    5640
gtaataagaa aaaggattaa ttatgagcga attgaattaa taataaggta atagatttac    5700
```

```
attagaaaat gaaggggat tttatgcgtg agaatgttac agtctatccc tggcgaaagg      5760
gggatgtgct gcaaggcgat taagttgggt aacgccaggg ttttcccagt cacgacgttg      5820
taaaacgacg gccagtgagc gcgcgtaata cgactcacta tagggcgaat tgggtaccgg      5880
gccccccctc gaggtcgacg gtatcgataa gcttttttaga catctaaatc taggtactaa      5940
aacaattcat ccagtaaaat ataatatttc ctgcagggcc agtgggcaag ttgaaaaatt      6000
cacaaaaatg tggtataata tctttgttca ttagagcgat aaacttgaat ttgagaggga      6060
acttagatgg tatttgaaaa aattgataaa aatagttgga acagaaaaga gtattttgac      6120
cactactttg caagtgtacc ttgtacctac agcatgaccg ttaaagtgga tatcacacaa      6180
ataaaggaaa agggaatgaa actatatcct gcaatgcttt attatattgc aatgattgta      6240
aaccgccatt cagagtttag gacggcaatc aatcaagatg gtgaattggg gatatatgat      6300
gagatgatac caagctatac aatatttcac aatgatactg aaacattttc cagcctttgg      6360
actgagtgta agtctgactt taaatcattt ttagcagatt atgaaagtga tacgcaacgg      6420
tatggaaaca atcatagaat ggaaggaaag ccaaatgctc cggaaaacat ttttaatgta      6480
tctatgatac cgtggtcaac cttcgatggc tttaatctga atttgcagaa aggatatgat      6540
tatttgattc ctattttttac tatggggaaa tattataaag aagataacaa aattatactt      6600
cctttggcaa ttcaagttca tcacgcagta tgtgacggat ttcacatttg ccgttttgta      6660
aacgaattgc aggaattgat aaatagttaa cttcaggttt gtctgtaact aaaaacaagt      6720
atttaagcaa aaacatcgta gaaatacggt gttttttgtt accctaaggc cggccgaatt      6780
gggcccgacg tcgcatgctc ccggccgcca tggcggccgc gggaattcga tatcactagt      6840
gaattcgcgg ccgcctgcag gtcgaccata tgggagagct cccaacgcgt tggattcaat      6900
tacattttca atttgatcaa taaagctacc atctcgcttt tgccaatggc gccattgtgc      6960
accataaacg tcgcctaaat taccatattt tttggcgaag ttctcatcat caaggatacg      7020
tcgatcaaat ttttttaatt cagcttgata aattttatta aattccggat cactttgact      7080
tcgtaaacca aaatcagtca tatcaggacc agtatattca tcactgttaa cccaattttt      7140
aaatgcccac tcatcccaaa tatgattttt atgttctaat aaaaaacgaa tattagtgtc      7200
ccctcgtaag aaccatagga gttcacttttt aattaaggcg gatacgatca agcgtcgcga      7260
gtatggatgc gtcttaatct gctcaatcac atcccccagc tggtcgatgg tgtcaccacg      7320
actggtatgc cacgcccgcc attgcgagcc ataaaccaat cctaaatcac cgtatttagc      7380
tgcaaatgac tcgtcagtga gaatacgttc gtcaaacttg gccatctgtt cacgataact      7440
ggcggcaaat tcaggatctt tctggctgcg atgaccaaaa tcggtcatat ccggaccatg      7500
ataatcgggg ctggcaaccc acttctcaaa ggcccattca tcccagatgt gattttatg      7560 ctgcaatagg aaacgaatgt tggtgtcgcc acgcaagaac caaagtaact cgcttttaat      7620
gagaccaaag gcacctttt tggttgttag taaaggaaac cctttgctaa ggtcaaaccg      7680
catttggtga ccaaaaatac tgtacgtgcc agtatgcgta cgatcaggct tgaaatggta      7740
```

<210> SEQ ID NO 2  
<211> LENGTH: 1290  
<212> TYPE: DNA  
<213> ORGANISM: Artificial Sequence  
<220> FEATURE:  
<223> OTHER INFORMATION: Artificially synthesized

<400> SEQUENCE: 2

```
tatctaaagt ttgcaacctt aacgtaagtc ttgtcagtgt tgtcaccgat cttgtagtac        60
```

```
ttttggccgt tcttgaatgt gtatgaagca ccgtaagtag ttacaacttc acccttcttc      120
aatacaacct tgttagcacg cttctttgat gatgcgtaaa cgtaagcgtt gtgcttcaaa      180
gtacgcttag taccatcgat gtttgcagcg ttgatgtact tgtcaacagc cttaccgttt      240
tcaactactt ggtagtaagt cttaccgttg atagtagtag tgtttggcaa tacgcttact      300
gagttgtaac gcttaacgct gtcagtacca acacgcttag cgtccttgtc gtagtagtat      360
gcgttgtgca taattctctt gcttacgctg gctacagttg gctcagcaac attaggaaca      420
gtaacaacta ctggcaaagt agctgactta ccattagtat ttgatgctaa atctgtatca      480
tctttagtca caaacccact tacggcaact gcactcggtg tactaccacc agttacatca      540
actttaaggg ttttgttgaa atcaatagtt gttcctttgc ctgcatattc taaacctgtt      600
gatggaagat tgattgcaat accagctgta gaatcaccta ctttaccata cttatcttca      660
acagcacccg ctttcatttc gacaacatat ccggtatctt cactacctcc actctttaag      720
ccaaaagttg ccacatcttt tacttttaac gcttttgttg ccgcaacatt ctttccttca      780
gaatcctgcg ttttagacac cattccaaac gtatctttag ttgcaatatc aattagcgtc      840
ttttcattta acgaattcaa tttagtaaca atagcttcgg catcggcttg attggtgata      900
atcttattct ctagattgta atcaacagaa aaatctacat aatcgccatc gcctaatttg      960
tctaattgtg tatttacaag attatacaac ttttctgcgg ctgcatctcg atctgctttc     1020
ttattcgctg atttaggtgc tacttctcct accacaccat cattgaaact gaccgtaatc     1080
ttaccaatac tattatcttt aagtccatct tgtaattgtt tgacagcctt tttccaatca     1140
ttcttaacca ccgtatagcc ttgtgtacca gtggttgcag caaatacagg tgcagcagcg     1200
ctaacagtag atacagcaga agcagcaact ggagcaacag caagtaaagc agcagcagca     1260
gcgctaacga ttcttaaatt tttcttcatg                                      1290

<210> SEQ ID NO 3
<211> LENGTH: 281
<212> TYPE: DNA
<213> ORGANISM: Artificial Sequence
<220> FEATURE:
<223> OTHER INFORMATION: Artificially synthesized

<400> SEQUENCE: 3
cctgcagaag cttcgaattc tgccttctga gcttcttcaa cacctttttc tgaaaggtta       60
acgtcaaccc aaccagtaaa ttggtttgaa aggttccatt cactttgacc gtgacggatt      120
aaaactaatt ttgacatgaa atatctcctt ttaaattcaa tgtttcatcc atattttaca      180
catttcacag ttttttttcat agagatatgg gcaaaaaaac atctttttt atttctactt       240 tttattttct gcttttttgt gctaacttat aacaagcata c                          281

<210> SEQ ID NO 4
<211> LENGTH: 817
<212> TYPE: DNA
<213> ORGANISM: Artificial Sequence
<220> FEATURE:
<223> OTHER INFORMATION: Artificially synthesized

<400> SEQUENCE: 4
ttacataata ggtaatacct ttactgcatc tttaacattg ctataagtct ttaatgaact       60
gaaatttgca tctaacttat tcatcttcat agctaattca ggcttaatac cagtaatgat      120
caattctgtg ccagttaact ttagtaggtg acttaactta aagatttgat cagcagtttg      180
```

```
ttcattcact tgtgcaagac cgctaagatc aataatcaag taatcatctt ttgaagtaga      240
aaggatatta gttaacgtac aaacaatact gttaaatctc tcttcagtaa gattgccaac      300
tagtggtaac gctgatatgc cgtttcttat aggtacaatt ggtgtagata aagcagtaat      360
ctctgttaat gaatcttcca ataacttttc atattctttt tgcttcgtaa tatcattttg      420
aataccaaca aagtatgttt tatcttcaat ttccatagga tctatattca attcgttcca      480
aaacatagtt ccgtcttttt tgtaattctg aatttgtact gtgactggtt ctttattctg      540
taaagcggta cggatgttat caacttcagc cgggtcggta tgtttacctt gcaaaaagcg      600
tgcgtttttt ccaagaatct cttgaaggaa tctggcattt ttcccaagaa tttcttcggt      660
ttcataacca gtcatttgta caaaaccttg attaacataa acaattggat tatcttccaa      720
agctggatca gtaatcacga ctccaacacg aacatgatct aatgcttttt tgattacttc      780
taattgtcct ggaataccaa atgattgaaa agatgcc                              817
```

<210> SEQ ID NO 5
<211> LENGTH: 697
<212> TYPE: DNA
<213> ORGANISM: Artificial Sequence
<220> FEATURE:
<223> OTHER INFORMATION: Artificially synthesized

<400> SEQUENCE: 5

```
atggctatta aaaatactaa agctagaaat tttggatttt tattatatcc tgactcaatt       60
cctaatgatt ggaaagaaaa attagagagt ttgggcgtat ctatggctgt cagtccttta      120
cacgatatgg acgaaaaaaa agataaagat acatggaata atagtaatat tatacaaaat      180
ggaaagcact ataaaaaacc acactatcac gttatatata ttgcacgaaa tcctgtaaca      240
atagaaagcg ttaggaacaa gattaagcga aaattgggga atagttcagt tgctcatgtt      300
gagatacttg attatatcaa aggttcatat gaatatttga ctcatgaatc aaaggacgct      360
attgctaaga ataaacatat atacgacaaa aaagatattt tgaacattaa tgattttgat      420
attgaccgct atataacact tgatgaaagc caaaaagag aattgaagaa tttactttta       480
gatatagtgg atgactataa tttggtaaat acaaaagatt taatggcttt tattcgcctt      540
aggggagcgg agtttggaat tttaaatacg aatgatgtaa aagatattgt ttcaacaaac      600
tctagcgcct ttagattatg gtttgagggc aattatcagt gtggatatag agcaagttat      660
gcaaaggttc ttgatgctga acgggggaa ataaaat                                697
```

<210> SEQ ID NO 6
<211> LENGTH: 624
<212> TYPE: DNA
<213> ORGANISM: Artificial Sequence
<220> FEATURE:
<223> OTHER INFORMATION: Artificially synthesized

<400> SEQUENCE: 6

```
atggtatttg aaaaaattga taaaaatagt tggaacagaa aagagtattt tgaccactac       60
tttgcaagtg taccttgtac ctacagcatg accgttaaag tggatatcac acaaataaag      120
gaaaagggaa tgaaactata tcctgcaatg ctttattata ttgcaatgat tgtaaaccgc      180
cattcagagt ttaggacggc aatcaatcaa gatggtgaat tggggatata tgatgagatg      240
ataccaagct atacaatatt tcacaatgat actgaaacat tttccagcct ttggactgag      300
tgtaagtctg actttaaatc attttttagca gattatgaaa gtgatacgca acggtatgga      360
aacaatcata gaatggaagg aaagccaaat gctccggaaa acatttttaa tgtatctatg      420
```

```
ataccgtggt caaccttcga tggctttaat ctgaatttgc agaaaggata tgattatttg    480
attcctattt ttactatggg gaaatattat aaagaagata caaaattat acttcctttg    540 gcaattcaag ttcatcacgc agtatgtgac ggatttcaca tttgccgttt gtaaacgaa     600 ttgcaggaat tgataaatag ttaa                                           624
```

<210> SEQ ID NO 7  
<211> LENGTH: 341  
<212> TYPE: DNA  
<213> ORGANISM: Artificial Sequence  
<220> FEATURE:  
<223> OTHER INFORMATION: Artificially synthesized

<400> SEQUENCE: 7

```
tcaattacat tttcaatttg atcaataaag ctaccatctc gcttttgcca atggcgccat     60
tgtgcaccat aaacgtcgcc taaattacca tattttttgg cgaagttctc atcatcaagg   120
atacgtcgat caattttttt taattcagct tgataaattt tattaaattc cggatcactt    180
tgacttcgta aaccaaaatc agtcatatca ggaccagtat attcatcact gttaacccaa    240
tttttaaatg cccactcatc ccaaatatga tttttatgtt ctaataaaaa acgaatatta    300
gtgtcccctc gtaagaacca taggagttca cttttaatta a                       341
```

<210> SEQ ID NO 8  
<211> LENGTH: 501  
<212> TYPE: DNA  
<213> ORGANISM: Artificial Sequence  
<220> FEATURE:  
<223> OTHER INFORMATION: Artificially synthesized

<400> SEQUENCE: 8

```
gcggatacga tcaagcgtcg cgagtatgga tgcgtcttaa tctgctcaat cacatccccc     60
agctggtcga tggtgtcacc acgactggta tgccacgccc gccattgcga gccataaacc   120
aatcctaaat caccgtatt agctgcaaat gactcgtcag tgagaatacg ttcgtcaaac    180
ttggccatct gttcacgata actggcggca aattcaggat ctttctggct gcgatgacca    240
aaatcggtca tatccggacc atgataatcg gggctggcaa cccacttctc aaaggcccat    300
tcatcccaga tgtgattttt atgctgcaat aggaaacgaa tgttggtgtc gccacgcaag    360
aaccaaagta actcgctttt aatgagacca aagggcaccct ttttggttgt tagtaaagga   420 aacccctttgc taaggtcaaa ccgcatttgg tgaccaaaaa tactgtacgt gccagtatgc    480
gtacgatcag gcttgaaatg g                                              501
```

<210> SEQ ID NO 9  
<211> LENGTH: 428  
<212> TYPE: PRT  
<213> ORGANISM: Artificial Sequence  
<220> FEATURE:  
<223> OTHER INFORMATION: Artificially synthesized

<400> SEQUENCE: 9

```
Lys Lys Asn Leu Arg Ile Val Ser Ala Ala Ala Ala Leu Leu Ala
1               5                   10                  15

Val Ala Pro Val Ala Ala Ser Ala Val Ser Thr Val Ser Ala Ala Ala
            20                  25                  30

Pro Val Phe Ala Ala Thr Thr Gly Thr Gln Gly Tyr Thr Val Val Lys
        35                  40                  45

Asn Asp Trp Lys Lys Ala Val Lys Gln Leu Gln Asp Gly Leu Lys Asp
```

```
            50                  55                  60
Asn Ser Ile Gly Lys Ile Thr Val Ser Phe Asn Asp Gly Val Val Gly
 65                  70                  75                  80

Glu Val Ala Pro Lys Ser Ala Asn Lys Lys Ala Asp Arg Asp Ala Ala
                 85                  90                  95

Ala Glu Lys Leu Tyr Asn Leu Val Asn Thr Gln Leu Asp Lys Leu Gly
            100                 105                 110

Asp Gly Asp Tyr Val Asp Phe Ser Val Asp Tyr Asn Leu Glu Asn Lys
        115                 120                 125

Ile Ile Thr Asn Gln Ala Asp Ala Glu Ala Ile Val Thr Lys Leu Asn
    130                 135                 140

Ser Leu Asn Glu Lys Thr Leu Ile Asp Ile Ala Thr Lys Asp Thr Phe
145                 150                 155                 160

Gly Met Val Ser Lys Thr Gln Asp Ser Glu Gly Lys Asn Val Ala Ala
                165                 170                 175

Thr Lys Ala Leu Lys Val Lys Asp Val Ala Thr Phe Gly Leu Lys Ser
            180                 185                 190

Gly Gly Ser Glu Asp Thr Gly Tyr Val Val Glu Met Lys Ala Gly Ala
        195                 200                 205

Val Glu Asp Lys Tyr Gly Lys Val Gly Asp Ser Thr Ala Gly Ile Ala
    210                 215                 220

Ile Asn Leu Pro Ser Thr Gly Leu Glu Tyr Ala Gly Lys Gly Thr Thr
225                 230                 235                 240

Ile Asp Phe Asn Lys Thr Leu Lys Val Asp Val Thr Gly Gly Ser Thr
                245                 250                 255

Pro Ser Ala Val Ala Val Ser Gly Phe Val Thr Lys Asp Asp Thr Asp
            260                 265                 270

Leu Ala Ser Asn Thr Asn Gly Lys Ser Ala Thr Leu Pro Val Val Val
        275                 280                 285

Thr Val Pro Asn Val Ala Glu Pro Thr Val Ala Ser Val Ser Lys Arg
    290                 295                 300

Ile Met His Asn Ala Tyr Tyr Asp Lys Asp Ala Lys Arg Val Gly
305                 310                 315                 320

Thr Asp Ser Val Lys Arg Tyr Asn Ser Val Ser Val Leu Pro Asn Thr
                325                 330                 335

Thr Thr Ile Asn Gly Lys Thr Tyr Tyr Gln Val Val Glu Asn Gly Lys
            340                 345                 350

Ala Val Asp Lys Tyr Ile Asn Ala Ala Asn Ile Asp Gly Thr Lys Arg
        355                 360                 365

Thr Leu Lys His Asn Ala Tyr Val Tyr Ala Ser Ser Lys Lys Arg Ala
    370                 375                 380

Asn Lys Val Val Leu Lys Lys Gly Glu Val Val Thr Thr Tyr Gly Ala
385                 390                 395                 400

Ser Tyr Thr Phe Lys Asn Gly Gln Lys Tyr Tyr Lys Ile Gly Asp Asn
                405                 410                 415

Thr Asp Lys Thr Tyr Val Lys Val Ala Asn Phe Arg
            420                 425
```

<210> SEQ ID NO 10
<211> LENGTH: 272
<212> TYPE: PRT
<213> ORGANISM: Artificial Sequence
<220> FEATURE:
<223> OTHER INFORMATION: Artificially synthesized

<400> SEQUENCE: 10

Met Ala Ser Phe Gln Ser Phe Gly Ile Pro Gly Gln Leu Glu Val Ile
1               5                   10                  15

Lys Lys Ala Leu Asp His Val Arg Val Gly Val Val Ile Thr Asp Pro
            20                  25                  30

Ala Leu Glu Asp Asn Pro Ile Val Tyr Val Asn Gln Gly Phe Val Gln
        35                  40                  45

Met Thr Gly Tyr Glu Thr Glu Glu Ile Leu Gly Lys Asn Ala Arg Phe
    50                  55                  60

Leu Gln Glu Ile Leu Gly Lys Asn Ala Arg Phe Leu Gln Gly Lys His
65                  70                  75                  80

Thr Asp Pro Ala Glu Val Asp Asn Ile Arg Thr Ala Leu Gln Asn Lys
                85                  90                  95

Glu Pro Val Thr Val Gln Ile Gln Asn Tyr Lys Lys Asp Gly Thr Met
            100                 105                 110

Phe Trp Asn Glu Leu Asn Ile Asp Pro Met Glu Ile Glu Asp Lys Thr
        115                 120                 125

Tyr Phe Val Gly Ile Gln Asn Asp Ile Thr Lys Gln Lys Glu Tyr Glu
    130                 135                 140

Lys Leu Leu Glu Asp Ser Leu Thr Glu Ile Thr Ala Leu Ser Thr Pro
145                 150                 155                 160

Ile Val Pro Ile Arg Asn Gly Ile Ser Ala Leu Pro Leu Val Gly Asn
                165                 170                 175

Leu Thr Glu Glu Arg Phe Asn Ser Ile Val Cys Thr Leu Thr Asn Ile
            180                 185                 190

Leu Ser Thr Ser Lys Asp Asp Tyr Leu Ile Ile Asp Leu Ser Gly Leu
        195                 200                 205

Ala Gln Val Asn Glu Gln Thr Ala Asp Gln Ile Phe Lys Leu Ser His
    210                 215                 220

Leu Leu Lys Leu Thr Gly Thr Glu Leu Ile Ile Thr Gly Ile Lys Pro
225                 230                 235                 240

Glu Leu Ala Met Lys Met Asn Lys Leu Asp Ala Asn Phe Ser Ser Leu
                245                 250                 255

Lys Thr Tyr Ser Asn Val Lys Asp Ala Val Lys Val Leu Pro Ile Met
            260                 265                 270

<210> SEQ ID NO 11
<211> LENGTH: 232
<212> TYPE: PRT
<213> ORGANISM: Artificial Sequence
<220> FEATURE:
<223> OTHER INFORMATION: Artificially synthesized

<400> SEQUENCE: 11

Met Ala Ile Lys Asn Thr Lys Ala Arg Asn Phe Gly Phe Leu Leu Tyr
1               5                   10                  15

Pro Asp Ser Ile Pro Asn Asp Trp Lys Glu Lys Leu Glu Ser Leu Gly
            20                  25                  30

Val Ser Met Ala Val Ser Pro Leu His Asp Met Asp Glu Lys Lys Asp
        35                  40                  45

Lys Asp Thr Trp Asn Asn Ser Asn Ile Ile Gln Asn Gly Lys His Tyr
    50                  55                  60

Lys Lys Pro His Tyr His Val Ile Tyr Ile Ala Arg Asn Pro Val Thr
65                  70                  75                  80

Ile Glu Ser Val Arg Asn Lys Ile Lys Arg Lys Leu Gly Asn Ser Ser

```
                85                  90                  95
Val Ala His Val Glu Ile Leu Asp Tyr Ile Lys Gly Ser Tyr Glu Tyr
            100                 105                 110

Leu Thr His Glu Ser Lys Asp Ala Ile Ala Lys Asn Lys His Ile Tyr
            115                 120                 125

Asp Lys Lys Asp Ile Leu Asn Ile Asn Asp Phe Asp Ile Asp Arg Tyr
            130                 135                 140

Ile Thr Leu Asp Glu Ser Gln Lys Arg Glu Leu Lys Asn Leu Leu Leu
145                 150                 155                 160

Asp Ile Val Asp Asp Tyr Asn Leu Val Asn Thr Lys Asp Leu Met Ala
                165                 170                 175

Phe Ile Arg Leu Arg Gly Ala Glu Phe Gly Ile Leu Asn Thr Asn Asp
                180                 185                 190

Val Lys Asp Ile Val Ser Thr Asn Ser Ala Phe Arg Leu Trp Phe
                195                 200                 205

Glu Gly Asn Tyr Gln Cys Gly Tyr Arg Ala Ser Tyr Ala Lys Val Leu
            210                 215                 220

Asp Ala Glu Thr Gly Glu Ile Lys
225                 230

<210> SEQ ID NO 12
<211> LENGTH: 207
<212> TYPE: PRT
<213> ORGANISM: Artificial Sequence
<220> FEATURE:
<223> OTHER INFORMATION: Artificially synthesized

<400> SEQUENCE: 12

Met Val Phe Glu Lys Ile Asp Lys Asn Ser Trp Asn Arg Lys Glu Tyr
1               5                   10                  15

Phe Asp His Tyr Phe Ala Ser Val Pro Cys Thr Tyr Ser Met Thr Val
                20                  25                  30

Lys Val Asp Ile Thr Gln Ile Lys Glu Lys Gly Met Lys Leu Tyr Pro
            35                  40                  45

Ala Met Leu Tyr Tyr Ile Ala Met Ile Val Asn Arg His Ser Glu Phe
        50                  55                  60

Arg Thr Ala Ile Asn Gln Asp Gly Glu Leu Gly Ile Tyr Asp Glu Met
65                  70                  75                  80

Ile Pro Ser Tyr Thr Ile Phe His Asn Asp Thr Glu Thr Phe Ser Ser
                85                  90                  95

Leu Trp Thr Glu Cys Lys Ser Asp Phe Lys Ser Phe Leu Ala Asp Tyr
            100                 105                 110

Glu Ser Asp Thr Gln Arg Tyr Gly Asn Asn His Arg Met Glu Gly Lys
        115                 120                 125

Pro Asn Ala Pro Glu Asn Ile Phe Asn Val Ser Met Ile Pro Trp Ser
130                 135                 140

Thr Phe Asp Gly Phe Asn Leu Asn Leu Gln Lys Gly Tyr Asp Tyr Leu
145                 150                 155                 160

Ile Pro Ile Phe Thr Met Gly Lys Tyr Tyr Lys Glu Asp Asn Lys Ile
                165                 170                 175

Ile Leu Pro Leu Ala Ile Gln Val His His Ala Val Cys Asp Gly Phe
            180                 185                 190

His Ile Cys Arg Phe Val Asn Glu Leu Gln Glu Leu Ile Asn Ser
        195                 200                 205
```

<210> SEQ ID NO 13
<211> LENGTH: 719
<212> TYPE: PRT
<213> ORGANISM: Clostridium difficile

<400> SEQUENCE: 13

| Met | Asn | Lys | Lys | Asn | Ile | Ala | Ile | Ala | Met | Ser | Gly | Leu | Thr | Val | Leu |
| 1 | | | | 5 | | | | | 10 | | | | | 15 | |

| Ala | Ser | Ala | Ala | Pro | Val | Phe | Ala | Ala | Thr | Thr | Gly | Thr | Gln | Gly | Tyr |
| | | | 20 | | | | | 25 | | | | | 30 | | |

| Thr | Val | Val | Lys | Asn | Asp | Trp | Lys | Ala | Val | Lys | Gln | Leu | Gln | Asp |
| | | 35 | | | | | 40 | | | | | 45 | | |

| Gly | Leu | Lys | Asp | Asn | Ser | Ile | Gly | Lys | Ile | Thr | Val | Ser | Phe | Asn | Asp |
| | 50 | | | | | 55 | | | | | 60 | | | | |

| Gly | Val | Val | Gly | Glu | Val | Ala | Pro | Lys | Ser | Ala | Asn | Lys | Lys | Ala | Asp |
| 65 | | | | | 70 | | | | | 75 | | | | | 80 |

| Arg | Asp | Ala | Ala | Ala | Glu | Lys | Leu | Tyr | Asn | Leu | Val | Asn | Thr | Gln | Leu |
| | | | | 85 | | | | | 90 | | | | | 95 | |

| Asp | Lys | Leu | Gly | Asp | Gly | Asp | Tyr | Val | Asp | Phe | Ser | Val | Asp | Tyr | Asn |
| | | | 100 | | | | | 105 | | | | | 110 | | |

| Leu | Glu | Asn | Lys | Ile | Ile | Thr | Asn | Gln | Ala | Asp | Ala | Glu | Ala | Ile | Val |
| | | | 115 | | | | 120 | | | | | 125 | | | |

| Thr | Lys | Leu | Asn | Ser | Leu | Asn | Glu | Lys | Thr | Leu | Ile | Asp | Ile | Ala | Thr |
| 130 | | | | | 135 | | | | | 140 | | | | | |

| Lys | Asp | Thr | Phe | Gly | Met | Val | Ser | Lys | Thr | Gln | Asp | Ser | Glu | Gly | Lys |
| 145 | | | | | 150 | | | | | 155 | | | | | 160 |

| Asn | Val | Ala | Ala | Thr | Lys | Ala | Leu | Lys | Val | Lys | Asp | Val | Ala | Thr | Phe |
| | | | | 165 | | | | | 170 | | | | | 175 | |

| Gly | Leu | Lys | Ser | Gly | Gly | Ser | Glu | Asp | Thr | Gly | Tyr | Val | Val | Glu | Met |
| | | | 180 | | | | | 185 | | | | | 190 | | |

| Lys | Ala | Gly | Ala | Val | Glu | Asp | Lys | Tyr | Gly | Lys | Val | Gly | Asp | Ser | Thr |
| | | 195 | | | | | 200 | | | | | 205 | | | |

| Ala | Gly | Ile | Ala | Ile | Asn | Leu | Pro | Ser | Thr | Gly | Leu | Glu | Tyr | Ala | Gly |
| 210 | | | | | 215 | | | | | 220 | | | | | |

| Lys | Gly | Thr | Thr | Ile | Asp | Phe | Asn | Lys | Thr | Leu | Lys | Val | Asp | Val | Thr |
| 225 | | | | | 230 | | | | | 235 | | | | | 240 |

| Gly | Gly | Ser | Thr | Pro | Ser | Ala | Val | Ala | Val | Ser | Gly | Phe | Val | Thr | Lys |
| | | | | 245 | | | | | 250 | | | | | 255 | |

| Asp | Asp | Thr | Asp | Leu | Ala | Lys | Ser | Gly | Thr | Ile | Asn | Val | Arg | Val | Ile |
| | | | 260 | | | | | 265 | | | | | 270 | | |

| Asn | Ala | Lys | Glu | Glu | Ser | Ile | Asp | Ile | Asp | Ala | Ser | Ser | Tyr | Thr | Ser |
| | | 275 | | | | | 280 | | | | | 285 | | | |

| Ala | Glu | Asn | Leu | Ala | Lys | Arg | Tyr | Val | Phe | Asp | Pro | Asp | Glu | Ile | Ser |
| 290 | | | | | 295 | | | | | 300 | | | | | |

| Glu | Ala | Tyr | Lys | Ala | Ile | Val | Ala | Leu | Gln | Asn | Asp | Gly | Ile | Glu | Ser |
| 305 | | | | | 310 | | | | | 315 | | | | | 320 |

| Asn | Leu | Val | Gln | Leu | Val | Asn | Gly | Lys | Tyr | Gln | Val | Ile | Phe | Tyr | Pro |
| | | | | 325 | | | | | 330 | | | | | 335 | |

| Glu | Gly | Lys | Arg | Leu | Glu | Thr | Lys | Ser | Ala | Asn | Asp | Thr | Ile | Ala | Ser |
| | | | 340 | | | | | 345 | | | | | 350 | | |

| Gln | Asp | Thr | Pro | Ala | Lys | Val | Val | Ile | Lys | Ala | Asn | Lys | Leu | Lys | Asp |
| | | 355 | | | | | 360 | | | | | 365 | | | |

| Leu | Lys | Asp | Tyr | Val | Asp | Leu | Lys | Thr | Tyr | Asn | Asn | Thr | Tyr | Ser |
| 370 | | | | | 375 | | | | | 380 | | | | | |

Asn Val Val Thr Val Ala Gly Glu Asp Arg Ile Glu Thr Ala Ile Glu
385                 390                 395                 400

Leu Ser Ser Lys Tyr Tyr Asn Ser Asp Asp Lys Asn Ala Ile Thr Asp
            405                 410                 415

Lys Ala Val Asn Asp Ile Val Leu Val Gly Ser Thr Ser Ile Val Asp
            420                 425                 430

Gly Leu Val Ala Ser Pro Leu Ala Ser Glu Lys Thr Ala Pro Leu Leu
            435                 440                 445

Leu Thr Ser Lys Asp Lys Leu Asp Ser Ser Val Lys Ser Glu Ile Lys
    450                 455                 460

Arg Val Met Asn Leu Lys Ser Asp Thr Gly Ile Asn Thr Ser Lys Lys
465                 470                 475                 480

Val Tyr Leu Ala Gly Val Asn Ser Ile Ser Lys Asp Val Glu Asn
            485                 490                 495

Glu Leu Lys Asn Met Gly Leu Lys Val Thr Arg Leu Ser Gly Glu Asp
            500                 505                 510

Arg Tyr Glu Thr Ser Leu Ala Ile Ala Asp Glu Ile Gly Leu Asp Asn
    515                 520                 525

Asp Lys Ala Phe Val Val Gly Gly Thr Gly Leu Ala Asp Ala Met Ser
    530                 535                 540

Ile Ala Pro Val Ala Ser Gln Leu Lys Asp Gly Asp Ala Thr Pro Ile
545                 550                 555                 560

Val Val Val Asp Gly Lys Ala Lys Glu Ile Ser Asp Ala Lys Ser
            565                 570                 575

Phe Leu Gly Thr Ser Asp Val Asp Ile Ile Gly Gly Lys Asn Ser Val
            580                 585                 590

Ser Lys Glu Ile Glu Glu Ser Ile Asp Ser Ala Thr Gly Lys Thr Pro
    595                 600                 605

Asp Arg Ile Ser Gly Asp Asp Arg Gln Ala Thr Asn Ala Glu Val Leu
610                 615                 620

Lys Glu Asp Asp Tyr Phe Thr Asp Gly Glu Val Val Asn Tyr Phe Val
625                 630                 635                 640

Ala Lys Asp Gly Ser Thr Lys Glu Asp Gln Leu Val Asp Ala Leu Ala
            645                 650                 655

Ala Ala Pro Ile Ala Gly Arg Phe Lys Glu Ser Pro Ala Pro Ile Ile
            660                 665                 670

Leu Ala Thr Asp Thr Leu Ser Ser Asp Gln Asn Val Ala Val Ser Lys
            675                 680                 685

Ala Val Pro Lys Asp Gly Gly Thr Asn Leu Val Gln Val Gly Lys Gly
            690                 695                 700

Ile Ala Ser Ser Val Ile Asn Lys Met Lys Asp Leu Leu Asp Met
705                 710                 715

<210> SEQ ID NO 14
<211> LENGTH: 444
<212> TYPE: PRT
<213> ORGANISM: Lactobacillus acidophilus

<400> SEQUENCE: 14

Met Lys Lys Asn Leu Arg Ile Val Ser Ala Ala Ala Ala Leu Leu
1               5                   10                  15

Ala Val Ala Pro Val Ala Ala Ser Ala Val Ser Thr Val Ser Ala Ala
            20                  25                  30

Thr Thr Ile Asn Ala Ser Ser Ser Ala Ile Asn Thr Asn Thr Asn Ala
        35                  40                  45

Lys Tyr Asp Val Asp Val Thr Pro Ser Val Ser Ala Val Ala Asn
            50                  55                  60

Thr Ala Asn Asn Thr Pro Ala Ile Ala Gly Asn Leu Thr Gly Thr Ile
 65                  70                  75                  80

Ser Ala Ser Tyr Asn Gly Lys Thr Tyr Thr Ala Asn Leu Lys Ala Asp
                 85                  90                  95

Thr Glu Asn Ala Thr Ile Thr Ala Ala Gly Ser Thr Thr Ala Val Lys
            100                 105                 110

Pro Ala Glu Leu Ala Ala Gly Val Ala Tyr Thr Val Thr Val Asn Asp
            115                 120                 125

Val Ser Phe Asn Phe Gly Ser Glu Asn Ala Gly Lys Thr Val Thr Leu
130                 135                 140

Gly Ser Ala Asn Ser Asn Val Lys Phe Thr Gly Thr Asn Ser Asp Asn
145                 150                 155                 160

Gln Thr Glu Thr Asn Val Ser Thr Leu Lys Val Lys Leu Asp Gln Asn
                165                 170                 175

Gly Val Ala Ser Leu Thr Asn Val Ser Ile Ala Asn Val Tyr Ala Ile
            180                 185                 190

Asn Thr Thr Asp Asn Ser Asn Val Asn Phe Tyr Asp Val Thr Ser Gly
            195                 200                 205

Ala Thr Val Thr Asn Gly Ala Val Ser Val Asn Ala Asp Asn Gln Gly
210                 215                 220

Gln Val Asn Val Ala Asn Val Ala Ala Ile Asn Ser Lys Tyr Phe
225                 230                 235                 240

Ala Ala Gln Tyr Ala Asp Lys Lys Leu Asn Thr Arg Thr Ala Asn Thr
                245                 250                 255

Glu Asp Ala Ile Lys Ala Ala Leu Lys Asp Gln Lys Ile Asp Val Asn
            260                 265                 270

Ser Val Gly Tyr Phe Lys Ala Pro His Thr Phe Thr Val Asn Val Lys
            275                 280                 285

Ala Thr Ser Asn Thr Asn Gly Lys Ser Ala Thr Leu Pro Val Val Val
290                 295                 300

Thr Val Pro Asn Val Ala Glu Pro Thr Val Ala Ser Val Ser Lys Arg
305                 310                 315                 320

Ile Met His Asn Ala Tyr Tyr Tyr Asp Lys Asp Ala Lys Arg Val Gly
                325                 330                 335

Thr Asp Ser Val Lys Arg Tyr Asn Ser Val Ser Val Leu Pro Asn Thr
            340                 345                 350

Thr Thr Ile Asn Gly Lys Thr Tyr Tyr Gln Val Val Glu Asn Gly Lys
            355                 360                 365

Ala Val Asp Lys Tyr Ile Asn Ala Ala Asn Ile Asp Gly Thr Lys Arg
            370                 375                 380

Thr Leu Lys His Asn Ala Tyr Val Tyr Ala Ser Ser Lys Lys Arg Ala
385                 390                 395                 400

Asn Lys Val Val Leu Lys Lys Gly Glu Val Val Thr Thr Tyr Gly Ala
                405                 410                 415

Ser Tyr Thr Phe Lys Asn Gly Gln Lys Tyr Tyr Lys Ile Gly Asp Asn
            420                 425                 430

Thr Asp Lys Thr Tyr Val Lys Val Ala Asn Phe Arg
            435                 440

<210> SEQ ID NO 15
<211> LENGTH: 244

```
<212> TYPE: PRT
<213> ORGANISM: Clostridium difficile

<400> SEQUENCE: 15

Ala Ala Pro Val Phe Ala Ala Thr Thr Gly Thr Gln Gly Tyr Thr Val
1               5                   10                  15

Val Lys Asn Asp Trp Lys Lys Ala Val Lys Gln Leu Gln Asp Gly Leu
            20                  25                  30

Lys Asp Asn Ser Ile Gly Lys Ile Thr Val Ser Phe Asn Asp Gly Val
        35                  40                  45

Val Gly Glu Val Ala Pro Lys Ser Ala Asn Lys Lys Ala Asp Arg Asp
    50                  55                  60

Ala Ala Ala Glu Lys Leu Tyr Asn Leu Val Asn Thr Gln Leu Asp Lys
65                  70                  75                  80

Leu Gly Asp Gly Asp Tyr Val Asp Phe Ser Val Asp Tyr Asn Leu Glu
                85                  90                  95

Asn Lys Ile Ile Thr Asn Gln Ala Asp Ala Glu Ala Ile Val Thr Lys
            100                 105                 110

Leu Asn Ser Leu Asn Glu Lys Thr Leu Ile Asp Ile Ala Thr Lys Asp
        115                 120                 125

Thr Phe Gly Met Val Ser Lys Thr Gln Asp Ser Glu Gly Lys Asn Val
130                 135                 140

Ala Ala Thr Lys Ala Leu Lys Val Lys Asp Val Ala Thr Phe Gly Leu
145                 150                 155                 160

Lys Ser Gly Gly Ser Glu Asp Thr Gly Tyr Val Val Glu Met Lys Ala
                165                 170                 175

Gly Ala Val Glu Asp Lys Tyr Gly Lys Val Gly Asp Ser Thr Ala Gly
            180                 185                 190

Ile Ala Ile Asn Leu Pro Ser Thr Gly Leu Glu Tyr Ala Gly Lys Gly
        195                 200                 205

Thr Thr Ile Asp Phe Asn Lys Thr Leu Lys Val Asp Val Thr Gly Gly
    210                 215                 220

Ser Thr Pro Ser Ala Val Ala Val Ser Gly Phe Val Thr Lys Asp Asp
225                 230                 235                 240

Thr Asp Leu Ala

<210> SEQ ID NO 16
<211> LENGTH: 323
<212> TYPE: PRT
<213> ORGANISM: Lactobacillus acidophilus

<400> SEQUENCE: 16

Ala Gly Glu Asp Arg Ile Glu Thr Ala Ile Glu Leu Ser Ser Lys Tyr
1               5                   10                  15

Tyr Asn Ser Asp Asp Lys Asn Ala Ile Thr Asp Lys Ala Val Asn Asp
            20                  25                  30

Ile Val Leu Val Gly Ser Thr Ser Ile Val Asp Gly Leu Val Ala Ser
        35                  40                  45

Pro Leu Ala Ser Glu Lys Thr Ala Pro Leu Leu Leu Thr Ser Lys Asp
    50                  55                  60

Lys Leu Asp Ser Ser Val Lys Ser Glu Ile Lys Arg Val Met Asn Leu
65                  70                  75                  80

Lys Ser Asp Thr Gly Ile Asn Thr Ser Lys Lys Val Tyr Leu Ala Gly
                85                  90                  95

Gly Val Asn Ser Ile Ser Lys Asp Val Glu Asn Glu Leu Lys Asn Met
```

```
            100                 105                 110
Gly Leu Lys Val Thr Arg Leu Ser Gly Glu Asp Arg Tyr Glu Thr Ser
            115                 120                 125

Leu Ala Ile Ala Asp Glu Ile Gly Leu Asp Asn Asp Lys Ala Phe Val
            130                 135                 140

Val Gly Gly Thr Gly Leu Ala Asp Ala Met Ser Ile Ala Pro Val Ala
145                 150                 155                 160

Ser Gln Leu Lys Asp Gly Asp Ala Thr Pro Ile Val Val Asp Gly
                165                 170                 175

Lys Ala Lys Glu Ile Ser Asp Ala Lys Ser Phe Leu Gly Thr Ser
                180                 185                 190

Asp Val Asp Ile Ile Gly Gly Lys Asn Ser Val Ser Lys Glu Ile Glu
            195                 200                 205

Glu Ser Ile Asp Ser Ala Thr Gly Lys Thr Pro Asp Arg Ile Ser Gly
    210                 215                 220

Asp Asp Arg Gln Ala Thr Asn Ala Glu Val Leu Lys Glu Asp Tyr
225                 230                 235                 240

Phe Thr Asp Gly Glu Val Val Asn Tyr Phe Ala Lys Asp Gly Ser
                245                 250                 255

Thr Lys Glu Asp Gln Leu Val Asp Ala Leu Ala Ala Pro Ile Ala
                260                 265                 270

Gly Arg Phe Lys Glu Ser Pro Ala Pro Ile Ile Leu Ala Thr Asp Thr
            275                 280                 285

Leu Ser Ser Asp Gln Asn Val Ala Val Ser Lys Ala Val Pro Lys Asp
    290                 295                 300

Gly Gly Thr Asn Leu Val Gln Val Gly Lys Gly Ile Ala Ser Ser Val
305                 310                 315                 320

Ile Asn Lys
```

<210> SEQ ID NO 17
<211> LENGTH: 429
<212> TYPE: PRT
<213> ORGANISM: Artificial Sequence
<220> FEATURE:
<223> OTHER INFORMATION: Artificially synthesized

<400> SEQUENCE: 17

```
Met Lys Lys Asn Leu Arg Ile Val Ser Ala Ala Ala Ala Leu Leu
1               5                   10                  15

Ala Val Ala Pro Val Ala Ala Ser Ala Val Ser Thr Val Ser Ala Ala
            20                  25                  30

Ala Pro Val Phe Ala Ala Thr Thr Gly Thr Gln Gly Tyr Thr Val Val
            35                  40                  45

Lys Asn Asp Trp Lys Lys Ala Val Lys Gln Leu Gln Asp Gly Leu Lys
    50                  55                  60

Asp Asn Ser Ile Gly Lys Ile Thr Val Ser Phe Asn Asp Gly Val Val
65                  70                  75                  80

Gly Glu Val Ala Pro Lys Ser Ala Asn Lys Lys Ala Asp Arg Asp Ala
                85                  90                  95

Ala Ala Glu Lys Leu Tyr Asn Leu Val Asn Thr Gln Leu Asp Lys Leu
            100                 105                 110

Gly Asp Gly Asp Tyr Val Asp Phe Ser Val Asp Tyr Asn Leu Glu Asn
        115                     120                 125

Lys Ile Ile Thr Asn Gln Ala Asp Ala Glu Ala Ile Val Thr Lys Leu
    130                 135                 140
```

```
Asn Ser Leu Asn Glu Lys Thr Leu Ile Asp Ile Ala Thr Lys Asp Thr
145                 150                 155                 160

Phe Gly Met Val Ser Lys Thr Gln Asp Ser Glu Gly Lys Asn Val Ala
                165                 170                 175

Ala Thr Lys Ala Leu Lys Val Lys Asp Val Ala Thr Phe Gly Leu Lys
            180                 185                 190

Ser Gly Gly Ser Glu Asp Thr Gly Tyr Val Val Glu Met Lys Ala Gly
            195                 200                 205

Ala Val Glu Asp Lys Tyr Gly Lys Val Gly Asp Ser Thr Ala Gly Ile
        210                 215                 220

Ala Ile Asn Leu Pro Ser Thr Gly Leu Glu Tyr Ala Gly Lys Gly Thr
225                 230                 235                 240

Thr Ile Asp Phe Asn Lys Thr Leu Lys Val Asp Val Thr Gly Gly Ser
                245                 250                 255

Thr Pro Ser Ala Val Ala Val Ser Gly Phe Val Thr Lys Asp Asp Thr
            260                 265                 270

Asp Leu Ala Ser Asn Thr Asn Gly Lys Ser Ala Thr Leu Pro Val Val
        275                 280                 285

Val Thr Val Pro Asn Val Ala Glu Pro Thr Val Ala Ser Val Ser Lys
290                 295                 300

Arg Ile Met His Asn Ala Tyr Tyr Tyr Asp Lys Asp Ala Lys Arg Val
305                 310                 315                 320

Gly Thr Asp Ser Val Lys Arg Tyr Asn Ser Val Ser Val Leu Pro Asn
                325                 330                 335

Thr Thr Thr Ile Asn Gly Lys Thr Tyr Tyr Gln Val Val Glu Asn Gly
            340                 345                 350

Lys Ala Val Asp Lys Tyr Ile Asn Ala Ala Asn Ile Asp Gly Thr Lys
        355                 360                 365

Arg Thr Leu Lys His Asn Ala Tyr Val Tyr Ala Ser Ser Lys Lys Arg
370                 375                 380

Ala Asn Lys Val Val Leu Lys Lys Gly Glu Val Val Thr Thr Tyr Gly
385                 390                 395                 400

Ala Ser Tyr Thr Phe Lys Asn Gly Gln Lys Tyr Tyr Lys Ile Gly Asp
                405                 410                 415

Asn Thr Asp Lys Thr Tyr Val Lys Val Ala Asn Phe Arg
            420                 425
```

<210> SEQ ID NO 18
<211> LENGTH: 1594
<212> TYPE: DNA
<213> ORGANISM: Artificial Sequence
<220> FEATURE:
<223> OTHER INFORMATION: Artificially synthesized

<400> SEQUENCE: 18

```
ttatctaaag tttgcaacct taacgtaagt cttgtcagtg ttgtcaccga tcttgtagta      60
cttttggccg ttcttgaatg tgtatgaagc accgtaagta gttacaactt caccttctt     120 caatacaacc ttgttagcac gcttctttga tgatgcgtaa acgtaagcgt tgtgcttcaa    180
agtacgctta gtaccatcga tgtttgcagc gttgatgtac ttgtcaacag ccttaccgtt    240
ttcaactact tggtagtaag tcttaccgtt gatagtagta gtgtttggca atacgcttac    300
tgagttgtaa cgcttaacgc tgtcagtacc aacacgctta gcgtccttgt cgtagtagta    360
tgcgttgtgc ataattctct tgcttacgct ggctacagtt ggctcagcaa cattaggaac    420
```

```
agtaacaact actggcaaag tagctgactt accattagta tttgatgcta aatctgtatc      480
atctttagtc acaaacccac ttacggcaac tgcactcggt gtactaccac cagttacatc      540
aactttaagg gttttgttga aatcaatagt tgttcctttg cctgcatatt ctaaacctgt      600
tgatggaaga ttgattgcaa taccagctgt agaatcacct actttaccat acttatcttc      660
aacagcaccc gctttcattt cgacaacata tccggtatct tcactacctc cactctttaa      720
gccaaaagtt gccacatctt ttacttttaa cgcttttgtt gccgcaacat tctttccttc      780
agaatcctgc gttttagaca ccattccaaa cgtatcttta gttgcaatat caattagcgt      840
cttttcattt aacgaattca atttagtaac aatagcttcg gcatcggctt gattggtgat      900
aatcttattc tctagattgt aatcaacaga aaaatctaca taatcgccat cgcctaattt      960
gtctaattgt gtatttacaa gattatacaa cttttctgcg gctgcatctc gatctgcttt     1020
cttattcgct gatttaggtg ctacttctcc taccacacca tcattgaaac tgaccgtaat     1080
cttaccaata ctattatctt taagtccatc ttgtaattgt ttgacagcct ttttccaatc     1140
attcttaacc accgtatagc cttgtgtacc agtggttgca gcaaatacag gtgcagcagc     1200
gctaacagta gatacagcag aagcagcaac tggagcaaca gcaagtaaag cagcagcagc     1260
agcgctaacg attcttaaat ttttcttcat ggatccatat gcacgtcgac gcgcctgcag     1320
aagcttcgaa ttctgccttc tgagcttctt caacaccttt ttctgaaagg ttaacgtcaa     1380
cccaaccagt aaattggttt gaaaggttcc attcactttg accgtgacgg attaaaacta     1440
attttgacat gaaatatctc cttttaaatt caatgtttca tccatatttt acacatttca     1500
cagttttttt catagagata tgggcaaaaa aacatctttt tttatttcta cttttttattt    1560 tctgcttttt tgtgctaact tataacaagc atac                                 1594
```

COMPOSITIONS COMPRISING A CHIMERIC BACTERIAL SURFACE LAYER PROTEIN AND METHODS OF USE THEREOF

CROSS-REFERENCE TO RELATED APPLICATION

The present application is a Section 371 U.S. national stage entry of International Patent Application No. PCT/US2018/052656, International Filing Date Sep. 25, 2018 which is entitled to priority under 35 U.S.C. § 119(e) to U.S. Provisional Patent Application No. 62/563,365, filed Sep. 26, 2017 which are hereby incorporated by reference in their entireties.

STATEMENT OF RIGHTS TO INVENTIONS MADE UNDER FEDERALLY SPONSORED RESEARCH

This invention was made with government support under Grant No. AI 121590 awarded by the National Institutes of Health (NIH). The government has certain rights in the invention.

BACKGROUND OF THE INVENTION

*Clostridium difficile* infection (CDI) is the leading cause of antibiotic- and healthcare-associated diarrhea and its containment and treatment imposes a significant financial burden, estimated to be over $3 billion in the USA alone. Since the year 2000, CDI epidemics and outbreaks have occurred in North America, Europe and Asia. These outbreaks have been variously associated with, or attributed to, the emergence of *Clostridium difficile* strains with increased virulence, an increase in resistance to commonly used antimicrobials such as the fluoroquinolones, or host susceptibilities, including the use of gastric acid suppressants, to name a few.

CDI affects 500,000-1,000,000 patients annually in the USA, and morbidity and mortality due to this pathogen have increased over the past 15 years. Currently, the only FDA-approved treatment involves prolonged antibiotic use, which is ironically, associated with disease relapse and the threat of burgeoning antibiotic resistance. CDI is precipitated when commensal flora are suppressed following antibiotic treatment. The use of antibiotics can suppress the protective normal microbiota causing susceptibility to infection. Exposure to *C. difficile* spores results in colonization of the host gastrointestinal tract. Current treatments include use of antibiotics, which alter the bacterial composition of the gut microbiome. Vaccines are being developed for preventing *C. difficile* disease, but do not protect against *C. difficile* colonization.

Bacterial adherence is thought to be an important *C. difficile* virulence attribute, with surface-layer proteins (SLPs) playing key roles (Merrigan et al., PLoS ONE 8, e78404 (2013)). *C. difficile* elaborates up to 29 different SLPs, which are displayed in para-crystalline architecture on the cell surface. *C. difficile* SLPs are also implicated in immune modulation; thus, they are critical non-toxin virulence factors. While SLPs have been proposed as anti-CDI vaccine candidates, the SLP-based vaccine trials have not been successful most likely due to the variability in SLP epitope antigenicity (Biazzo et al., J Med Microbiol 62, 1444-1452 (2013)). At present, effective treatments and preventatives for CDI and colonization are lacking.

There is an urgent need in the art for new compositions and methods for CDI treatment. This invention addresses this need.

SUMMARY OF THE INVENTION

In one aspect, the invention includes a chimeric nucleic acid molecule comprising a nucleic acid sequence having a phosphoglycerate mutase (pgm) constitutive promoter (pgm promoter) and a nucleic acid sequence encoding a chimeric bacterial surface layer protein A (SlpA) comprising a *Clostridium difficile* derived host-cell binding domain and a lactic acid bacterium (LAB) derived peptidoglycan anchor.

In another aspect, the invention includes a chimeric polypeptide encoded by a nucleic acid sequence comprising a phosphoglycerate mutase (pgm) constitutive promoter (pgm promoter) and a nucleic acid sequence encoding a bacterial surface layer protein A (SlpA) comprising a *Clostridium difficile* derived host-cell binding domain and a lactic acid bacterium (LAB) derived peptidoglycan anchor.

In yet another aspect, the invention includes a vector comprising a nucleic acid sequence comprising a chimeric surface layer protein A (slpA) gene of *Lactobacillus acidophilus* and *Clostridium difficile*; a pgm promoter; an ytvA fluorescent allele from *B. subtilis*; a temperature sensitive repA gene; a chloramphenicol resistance cat gene; an internal fragment of *Lactobacillus acidophilus* thymidylate synthase A (thyA); and an internal fragment of *Lactobacillus casei* thyA.

In yet another aspect, the invention includes an engineered cell comprising the aforementioned chimeric nucleic acid molecule and the aforementioned vector.

In yet another aspect, there is provided a method of treating or preventing *Clostridium difficile* infection in a mammal. The method comprises administering to the mammal the engineered cell, thereby treating or preventing *Clostridium difficile* infection in the mammal.

In yet another aspect, the invention is a method of colonizing the gut of a mammal with an engineered lactic acid bacterium (LAB). The method comprising administering to the mammal the engineered cell, thereby colonizing the gut of the mammal with the LAB In certain embodiments, the pgm of the chimeric nucleic acid molecule is from a *Lactobacillus* species selected from the group consisting of *Lactobacillus acidophilus* or *Lactobacillus casei*. In certain embodiments, the LAB of the chimeric nucleic acid molecule is from a *Lactobacillus* species selected from the group consisting of *Lactobacillus acidophilus* or *Lactobacillus casei*. In certain other embodiments, the nucleic acid sequence comprising the pgm promoter and the nucleic acid sequence encoding the SlpA has the nucleic acid sequence of SEQ ID NO: 18.

In certain embodiments, the pgm of the chimeric polypeptide is from a *Lactobacillus* species selected from the group consisting of *Lactobacillus acidophilus* or *Lactobacillus casei*. In certain embodiments, the LAB of the chimeric polypeptide is selected from the group consisting of *Lactobacillus acidophilus* or *Lactobacillus casei*. In certain other embodiments, the nucleic acid sequence comprising the pgm promoter and the nucleic acid sequence encoding the SlpA have the nucleic acid sequence of SEQ ID NO: 18.

In certain embodiments, the pgm of the vector is from a *Lactobacillus* species selected from the group consisting of *Lactobacillus acidophilus* or *Lactobacillus casei*. In certain embodiments, the vector is a *Lactobacillus* expression vector. In certain embodiments, the vector is pMGM15. In certain embodiments, the vector comprises the nucleic acid sequence of SEQ ID NO: 1.

In certain embodiments, the chimeric nucleic acid molecule or the nucleic acid sequence encoding the vector is integrated into the chromosome of the engineered cell. In certain embodiments, the engineered cell comprises a LAB selected from the group consisting of a human-derived *Lactobacillus* species, a human-derived *Lactobacillus acidophilus*, and a human-derived *Lactobacillus casei*.

In certain embodiments, the administered engineered cell is selected from the group consisting of a human-derived *Lactobacillus*, a human-derived *Lactobacillus acidophilus*, and a human-derived *Lactobacillus casei*. In certain embodiments, the engineered cell is administered orally. In certain other embodiments, the engineered cell is administered daily. In certain embodiments, the mammal is a human.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1 depicts the nucleic acid sequence of SlpA-chimera-expressing plasmid (pMGM15; SEQ ID NO: 1). This plasmid comprises a *Clostridium difficile/L. acidophilus* SlpA chimera; a constitutive promoter from *L. acidophilus* pgm gene (located at bp1448-bp1728; a ribosome-binding site (highlighted and underlined); a ytvA fluorescent allele from *B. subtilis*; a temperature-sensitive repA gene to force plasmid integration into genome; a chloramphenicol resistance cassette cat; a *L. acidophilus* thyA fragment to facilitate Campbell integration; and a *L. casei* thyA fragment to facilitate Campbell integration. Translation start and stop codons are denoted by wavy lines below the specific codons.

FIG. 2A: pMGM15 comprises slpA *L. acidophilus/C. difficile* chimera: bp135-bp1424 (SEQ ID NO: 2); a strong constitutive promoter from *L. acidophilus* phosphoglycerate mutase (pgm) gene: bp1448-bp1728 (Duong et al., 2011, Microb Biotechnol, 4(3), 357-367); (SEQ ID NO: 3); ytvA fluorescent allele of ytvA from *B. subtilis*: bp2119-bp2937; (SEQ ID NO: 4); a temperature sensitive repA gene: bp4415-bp5113; (SEQ ID NO: 5); a Chloramphenicol resistance cat gene: bp6067-bp6690; (SEQ ID NO: 6); an internal fragment of *L. acidophilus* thyA: bp6895-7236; (SEQ ID NO: 7) and an internal fragment of *L. casei* thyA bp7238-bp7738; (SEQ ID NO: 8). FIG. 2B: The slpA *L. acidophilus/C. difficile* chimera was designed with: (1) a strong *L. acidophilus* (LA) phosphoglyceromutase (pgm) promoter; (2) LA Shine-Dalgarno (ribosome binding site) sequence; (3) a LA signal sequence ("SS" from the LA SlpA ortholog); (4) the *C. difficile* strain 630 host-cell-binding fragment; and (5) the LA bacterial cell-wall-binding domain.

FIG. 3 depicts the amino acid sequences of all the coding regions of the pMGM15 plasmid: *Clostridium difficile-L. acidophilus* SlpA chimera (SEQ ID NO: 9); YtvA fluorescent protein (SEQ ID NO: 10); RepA temperature-sensitive protein (SEQ ID NO: 11); and chloramphenicol acetyltransferase (SEQ ID NO: 12).

FIG. 6 is a series of fluorescence-activated cell sorting (FACS) graphs generated using anti-*C. difficile* SlpA antiserum to detect surface-exposed chimeric protein. The graphs show that Syn-LAB 2.0 and Syn-LAB 2.1 bacteria strongly express the SlpA chimera. Syn-LAB 2.0 and Syn-LAB 2.1 display chimeric SlpA. *L. casei* does not have a classic SLP layer, therefore, Syn-LAB 2.0 shift is unique (second graph). *L. acidophilus* has a SLP layer (unrelated to *C. difficile* SLP), therefore, Syn-LAB 2.1 chimeric SlpA is detected as a discrete, strong fluorescence shift (fourth graph).

FIGS. 7A and 7B depicts fluorescence-activating cell sorting analyses. (a) unstained *L. casei* parent strain; (b) unstained Syn-LAB 2.0; (c) SlpA-stained *L. casei* parent strain; (d) SlpA-stained Syn-LAB 2.0 (median fluorescence >100,000). *L. casei* does not have a classic S-layer, therefore, Syn-LAB shift is unique. (e) unstained *L. acidophilus* parent strain; (f) unstained Syn-LAB 2.1; (g) SlpA-stained *L. acidophilus* parent strain; (h) SlpA-stained Syn-LAB 2.1 (median fluorescence >4,000). *L. acidophilus* has a native S-layer; therefore, chimeric SlpA is detected as a discrete, strong fluorescence shift. Panels C-F, microscopy; FIG. 7C shows brightfield image, *L. casei* parent strain with minimal detectable SlpA fluorescence; FIG. 7D shows brightfield image, *L. acidophilus* parent strain with undetectable SlpA fluorescence; FIG. 7E shows immunofluorescence, Syn-LAB 2.0 with intense, punctate, SlpA staining, and FIG. 7F shows immunofluorescence, Syn-LAB 2.1 with intense SlpA staining. All strains were probed with a *C. difficile*-specific anti-SlpA serum. Images are representative of at least 20 fields and >1000 bacteria visualized. All images were visualized with a high-resolution DeltaVision deconvolution microscope. Gram's stained bacteria are shown in rectangles below each of FIG. 7C-7F.

*dophilus* strain (d), or Syn-LAB 2.1 (f), for 8 hours. Experiments were performed in at least three biological replicates. Host cells were treated with 100 bacteria per cell (MOI=100).

Figures 10A, 10B:
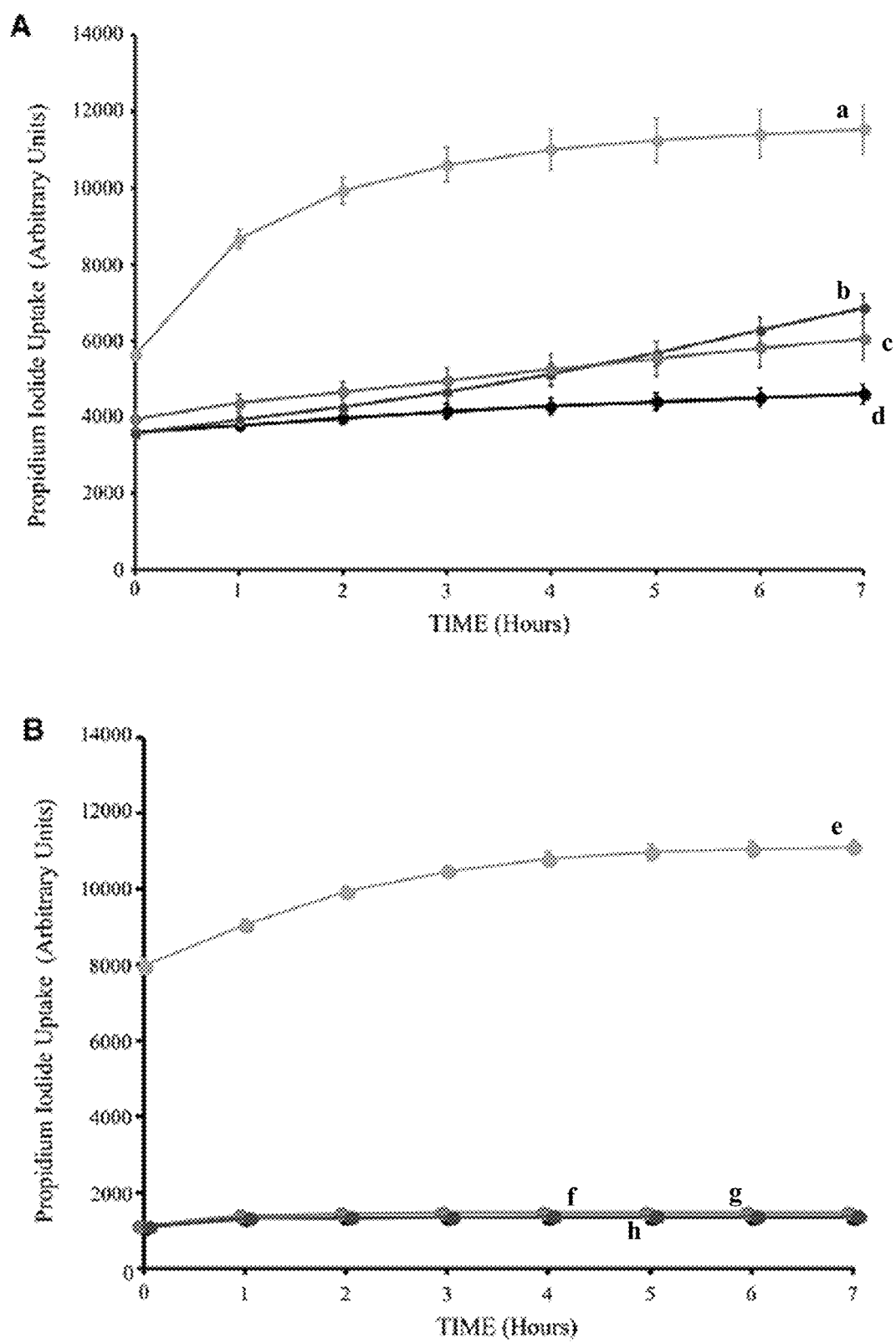

FIGS. 10A and 10B show that Lactic acid bacteria (LAB) treatment does not impact host-cell viability. Propidium iodide uptake assays of C2BBe monolayers mock-treated (d), or exposed to the parent *L. casei* strain (c), or Syn-LAB 2.0 (b) or parent *L. acidophilus* strain (f), or Syn-LAB 2.1 (g), for 8 h. Methanol-treated monolayers representative of maximal cell death (a & e). Experiments were performed in at least three biological replicates. Host cells were treated with 100 bacteria per cell (MOI=100).

Figure 11:
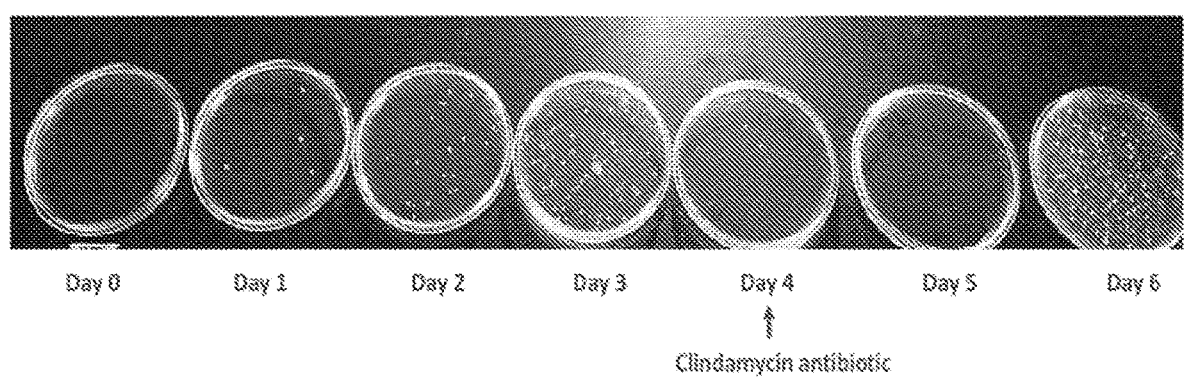

FIG. 11 is a series of images of petri dishes validating that Syn-LAB 2.0 efficiently colonizes Golden Syrian hamster gastrointestinal tract, is detectable as soon as 1 day post-administration, and is cleared from the intestine by antibiotics.

Figures 12A, 12B:
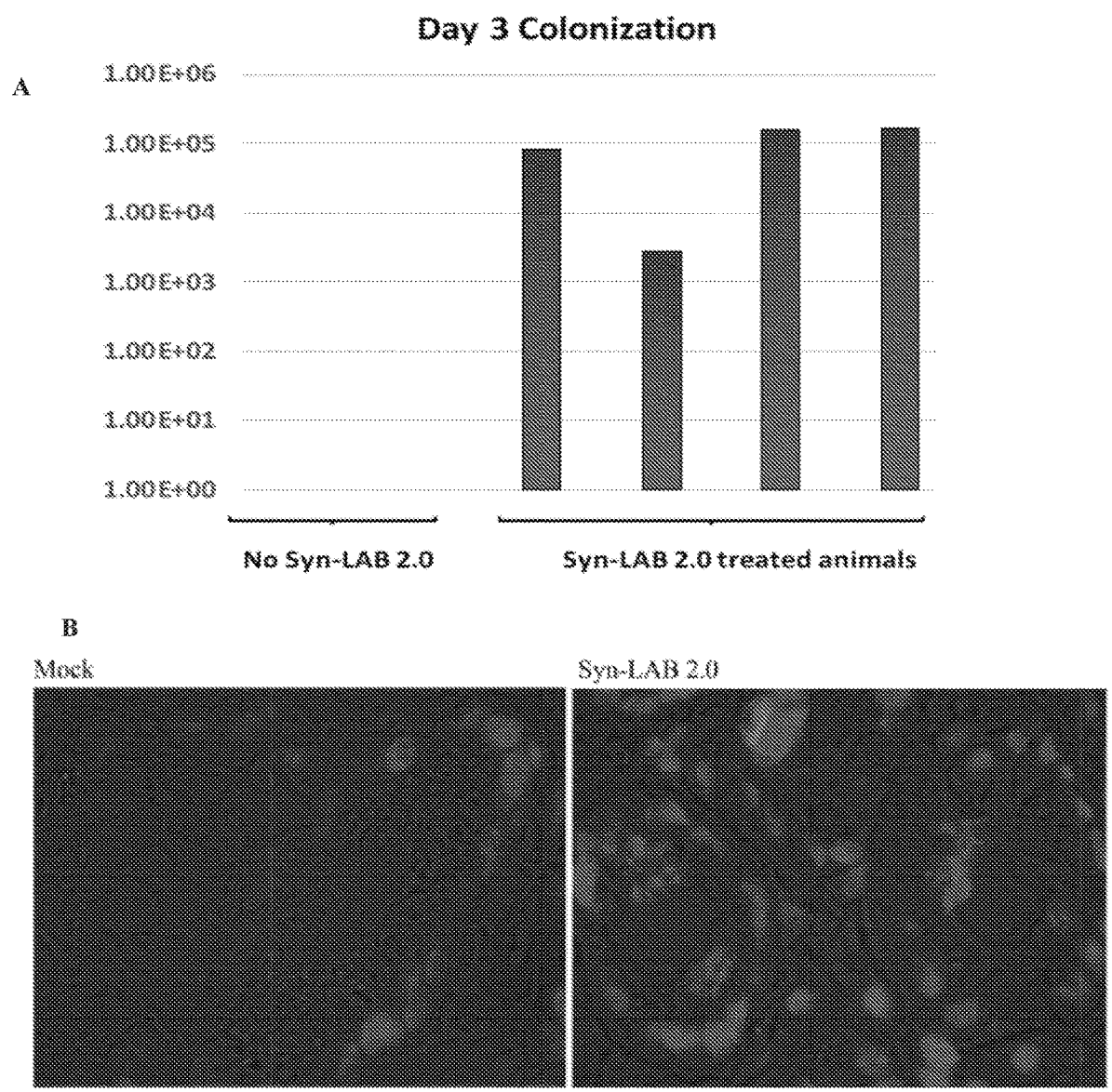

FIG. 12A is a histogram showing that in the treated animals Syn-LAB 2.0 fecal titers reached, or exceeded $10^5$ colony forming unit/gram stool on Day 3 post-treatment. Each bar represents an individual animal.

FIG. 12B illustrates that immunofluorescence analysis using anti-*C. difficile* SlpA serum reveals intense staining in the colonic lumen of Syn-LAB 2.0-fed animals (right), but not in mock-treated animals (left). Images are representative at least 10 fields visualized per section.

Figure 13:

FIG. 13 is a photograph illustrating that Syn-LAB treatment is safe and tolerable. No adverse effects in any Syn-LAB-treated animals was detected. The treated animals showed appropriate activity and alertness throughout the study.

Figures 14A, 14B:
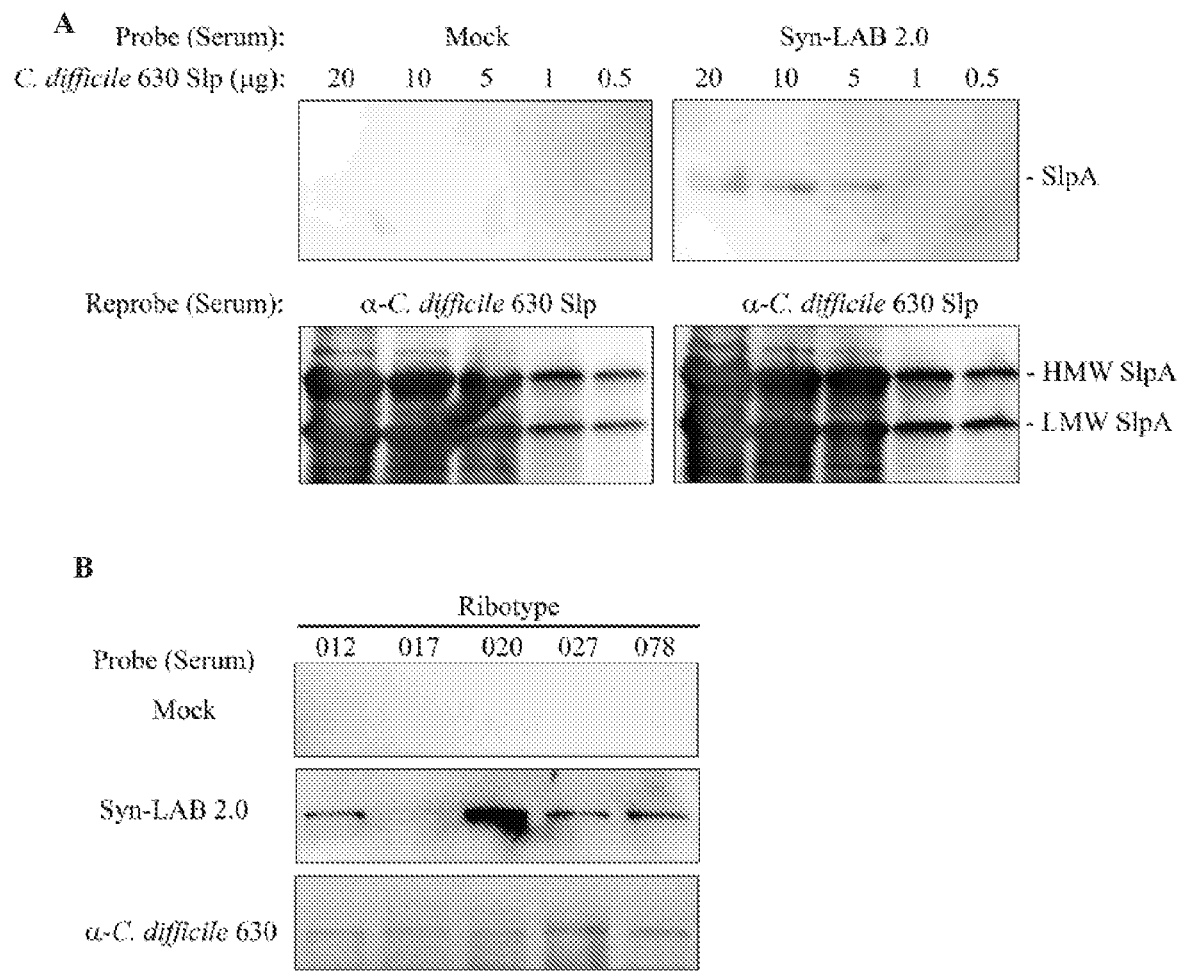

FIG. 14A shows Syn-LAB 2.0 elicits an anti-*C. difficile* SlpA immune response. Top panels, dose-response immunoblots of S-layer proteins (20 to 0.5 mg) from *C. difficile* strain 630 probed with serum from a Syn-LAB 2.0-treated animal (right), or serum from an untreated, age- and weight-matched hamster (left). Bottom panels, to verify efficient separation and transfer of the S-layer proteins, the membranes were stripped and re-probed with a polyclonal *C. difficile* anti-SlpA antiserum. Both *C. difficile* SlpA subunits were detected (arrows).

FIG. 14B shows S-layer proteins from *C. difficile* clinical isolates of diverse ribotypes probed with serum from an untreated animal (upper row), a Syn-LAB 2.0-treated animal (middle row), or with anti-*C. difficile* strain 630 SlpA serum (bottom row).

Figures 15A, 15B, 15C:
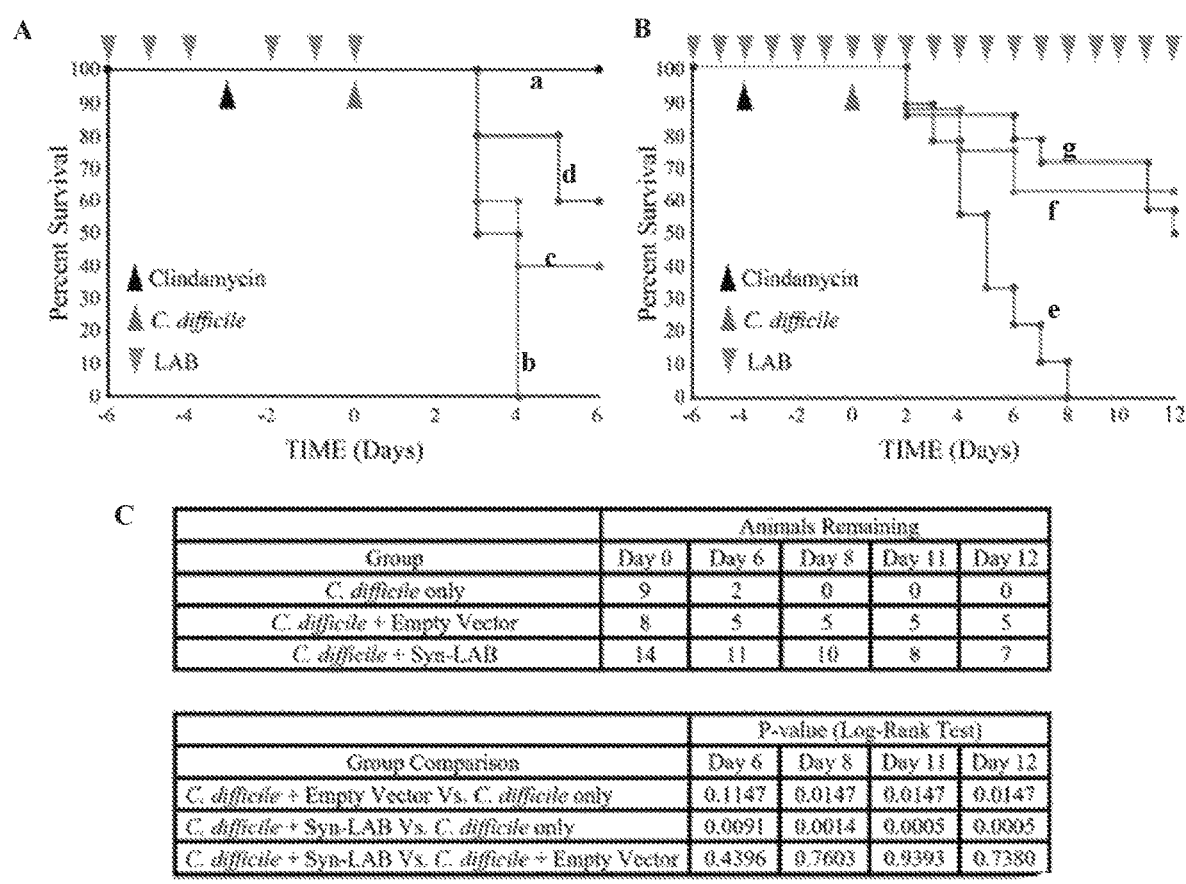

FIGS. 15A and 15B show that co-administration of Syn-LAB 2.0 and 2.1 protects Golden Syrian hamsters from CDI. FIG. 15A shows pilot study; Kaplan-Meier survival plot. Pre-treatment with Syn-LABs (6 once-daily doses of $1 \times 10^{10}$ CFU each) delays death of hamsters infected with 1000 *C. difficile* spores. (a) untreated, uninfected animals; (b) *C. difficile*-infected animals; (c) animals treated with parent LAB strains harboring empty vector, and then infected; (d) animals treated with Syn-Lab 2.0+2.1 and then infected. FIG. 15B shows powered study, Kaplan-Meier survival plot. Continuous Syn-LAB 2.0+2.1 dosing (pre- and post-infection) prevents death of *C. difficile*-infected hamsters. (e), *C. difficile*-infected animals; (f) animals treated with parent LAB strains harboring empty vector, and then infected; (g) animals treated with Syn-Lab 2.0+2.1 and then infected.

FIG. 15C shows group comparisons and statistical test results. Number of surviving animals in powered study (top), and Log-Rank tests (bottom). p 0.01=significant.

Figures 16A, 16B:
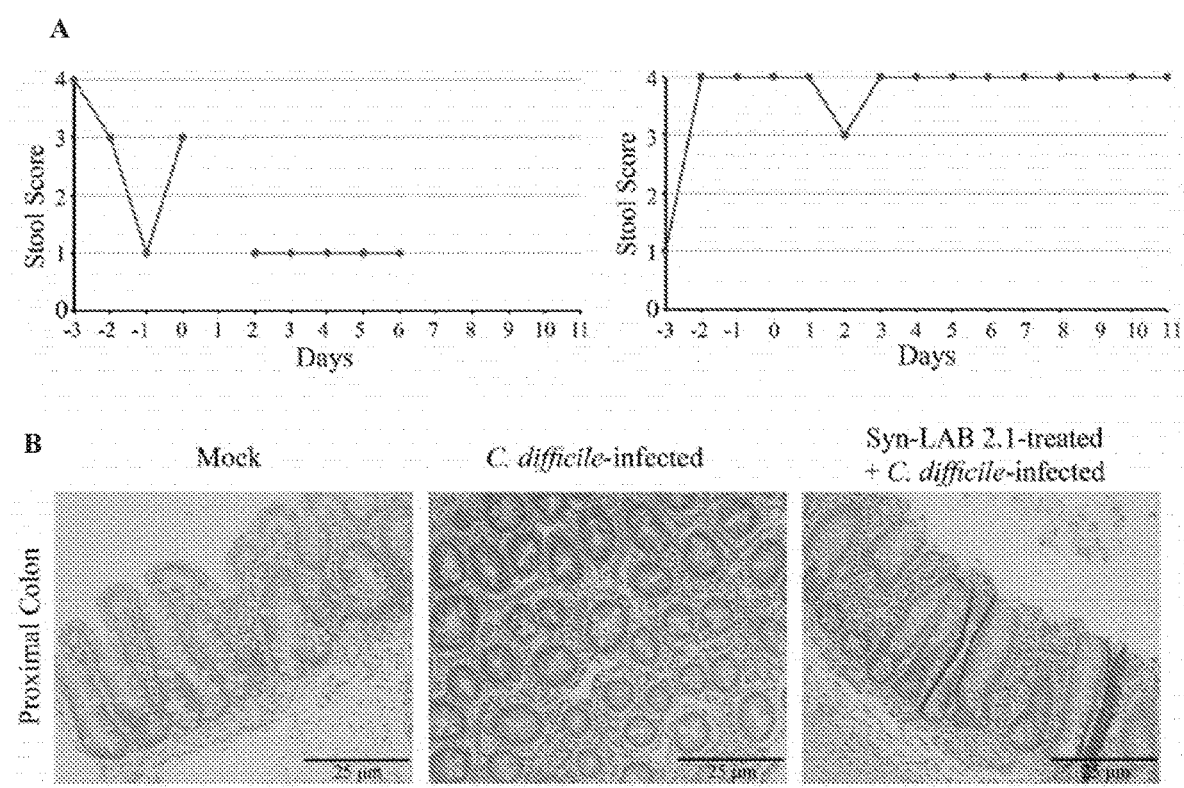

FIGS. 16A and 16B show Syn-LAB 2.1 protects piglets from CDI diarrhea. Pilot, non-lethal CDI model. FIG. 16A show stool consistency scoring; 1=diarrheic, 4=fully formed. Left, *C. difficile*-infected animal, with consistently low stool scores indicating unremitting diarrhea. Right, Syn-LAB 2.1 treated+*C. difficile*-infected animal, with consistently high stool score, indicating no diarrhea. The example shown is representative of 3 animals studied. The animal in the left panel was euthanized after the last time-point shown due to unremitting diarrhea, increasing dehydration and inappetence. Similar results for the other two animals. All infected animals in the group received 1000 spores of *C. difficile*. FIG. 16B depicts microscopic examination of proximal colon tissues from piglets. Left, hematoxylin-eosin staining of tissue from uninfected animal showing normal epithelium, little/no inflammatory infiltrate and no overt damage or necrosis. Middle, *C. difficile*-infected animal, revealing gross hemorrhage with an abundance of inflammatory infiltrates. Right, Syn-LAB 2.1-treated and *C. difficile*-infected animal tissue showing marked reduction in both overt hemorrhage and inflammation.

DETAILED DESCRIPTION

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "Surface-Layer Protein A (SlpA)" is meant a polypeptide or fragment thereof having at least about 85% or greater amino acid identity to the amino acid sequence provided at NCBI Accession No. CAJ69681 or WP_011254065 and having bacterial adherence activity. Exemplary SlpA amino acid sequences are provided below:

```
Clostridium difficile SlpA (full length sequence)
                                                      (SEQ ID NO: 13)
  1  mnkkniaiam sgltvlasaa pvfaattgtq gytvvkndwk kavkqlqdgl kdnsigkitv 61  sfndgvvgev apksankkad rdaaaeklyn lvntqldklg dgdyvdfsvd ynlenkiitn 121  qadaeaivtk lnslnektli diatkdtfgm vsktqdsegk nvaatkalkv kdvatfglks 181  ggsedtgyvv emkagavedk ygkvgdstag iainlpstgl eyagkgttid fnktlkvdvt 241  ggstpsavav sgfvtkddtd laksgtinvr vinakeesid idassytsae nlakryvfdp
```

```
301 deiseaykai valqndgies nlvqlvngky qvifypegkr letksandti asqdtpakvv 361 ikanklkdlk dyvddlktyn ntysnvvtva gedrietaie lsskyynsdd knaitdkavn 421 divlvgstsi vdglvaspla sektaplllt skdkldssvk seikrvmnlk sdtgintskk 481 vylaggvnsi skdvenelkn mglkvtrlsg edryetslai adeigldndk afvvggtgla 541 damsiapvas qlkdgdatpi vvvdgkakei sddaksflgt sdvdiiggkn syskeieesi 601 dsatgktpdr isgddrqatn aevlkeddyf tdgevvnyfv akdgstkedq lvdalaaapi 661 agrfkespap iilatdtlss dqnvayskav pkdggtnlvq vgkgiassvi nkmkdlldm
```

*Lactobacillus acidophilus* SlpA ortholog cell-wall anchor
(SEQ ID NO: 14)

```
  1 mkknlrivsa aaaallavap vaasavstvs aattinasss aintntnaky dvdvtpsvsa 61 vaantanntp aiagnltgti sasyngktyt anlkadtena titaagstta vkpaelaagv 121 aytvtvndvs fnfgsenagk tvtlgsansn vkftgtnsdn qtetnvstlk vkldqngvas 181 ltnvsianvy ainttdnsnv nfydvtsgat vtngavsvna dnqgqvnvan vvaainskyf 241 aaqyadkkln trtantedai kaalkdqkid vnsvgyfkap htftvnvkat sntngksatl 301 pvvvtvpnva eptvasvskr imhnayyydk dakrvgtdsv krynsysvlp ntttingkty 361 yqvvengkav dkyinaanid gtkrtlkhna yvyasskkra nkvvlkkgev vttygasytf 421 kngqkyykig dntdktyvkv anfr
```

By "SlpA nucleic acid molecule" is meant a polynucleotide encoding SlpA.

By "SlpA variable domain" is meant a polypeptide having 85% identity to the following sequence (SEQ ID NO: 15):

AAPVFAATTGTQGYTVVKNDWKKAVKQLQDGLKDNSIGKITVSFNDGVVG

EVAPKSANKKADRDAAAEKLYNLVNTQLDKLGDGDYVDFSVDYNLENKII

TNQADAEAIVTKLNSLNEKTLIDIATKDTFGMVSKTQDSEGKNVAATKAL

KVKDVATFGLKSGGSEDTGYVVEMKAGAVEDKYGKVGDSTAGIAINLPST

GLEYAGKGTTIDFNKTLKVDVTGGSTPSAVAVSGFVTKDDTDLA

In one embodiment, the SlpA variable domain is from *C. difficile* SlpA.

By "SlpA cell wall binding domain" is meant a polypeptide having 85% identity to the following sequence (SEQ ID NO: 16):

agedrietaielsskyynsddknaitdkavndivlvgstsivdglvaspl asektaplllltskdkldssvkseikrvmnlksdtgintskkvylaggvns iskdvenelknmglkvtrlsgedryetslaiadeigldndkafvvggtgl adamsiapvasqlkdgdatpivvvdgkakeisddaksflgtsdvdiiggk nsvskeieesidsatgktpdrisgddrqatnaevlkeddyftdgevvnyf vakdgstkedqlvdalaaapiagrfkespapiilatdtlssdqnvavska vpkdggtnlvqvgkgiassvink In one embodiment, the SlpA cell wall binding domain is from *Lactobacillus* (e.g., *Lactobacillus acidophilus*).

By "chimeric SlpA" is meant a polypeptide having two or more SlpA sequences from two or more bacterial strains. In one embodiment, a chimeric SlpA has an SlpA variable domain from *C. difficile* SlpA and an SlpA cell wall binding from *Lactobacillus acidophilus*.

In another embodiment, a chimeric SlpA has an SlpA signal sequence from *Lactobacillus acidophilus*, an SlpA variable domain from *C. difficile* SlpA and an SlpA cell wall binding from *Lactobacillus acidophilus*. An exemplary chimeric SlpA sequence is provided below (SEQ ID NO: 17):

| | |
|---|---|
| MKKNLRIVSAAAAALLAVAPVAASAVSTVSAAAPVFAATTGTQGYTVVKN | 50 |
| DWKKAVKQLQDGLKDNSIGKITVSFNDGVVGEVAPKSANKKADRDAAAEK | 100 |
| LYNLVNTQLDKLGDGDYVDFSVDYNLENKIITNQADAEAIVTKLNSLNEK | 150 |
| TLIDIATKDTEGMVSKTQDSEGKNVAATKALKVKDVATEGLKSGGSEDTG | 200 |
| YVVEMKAGAVEDKYGKVGDSTAGIAINLPSTGLEYAGKGTTIDFNKTLKV | 250 |
| DVTGGSTPSAVAVSGFVTKDDTDLASNTNGKSATLPVVVTVPNVAEPTVA | 300 |
| SVSKRIMHNAYYYDKDAKRVGTDSVKRYNSVSVLPNTTTINGKTYYQVVE | 350 |

-continued

```
NGKAVDKYINAANIDGTKRTLKHNAYVYASSKKRANKVVLKKGEVVTTYG    400

ASYTEKNGQKYYKIGDNTDKTYVKVANFR*
```

By "undesirable gut microbiome" is meant a community of microbes comprising a pathogen or having a biological activity associated with a pathogenic process. In one embodiment, an undesirable gut microbiome comprises an increased number or percentage of *Clostridium difficile* relative to the number or percentage of *C. difficile* present in the gut of a healthy control subject.

By "normal gut flora" is meant a population of microbes that is substantially similar to the population of microbes present in the gut of a healthy control subject.

By "ameliorate" is meant decrease, suppress, attenuate, diminish, arrest, or stabilize the development or progression of a disease.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

By "effective amount" is meant the amount of a composition of the invention (e.g., comprising a probiotic bacteria expressing *Clostridium difficile* SlpA, or fragment thereof) required to ameliorate the symptoms of a disease relative to an untreated patient. The effective amount of probiotic bacteria of the invention varies depending upon the manner of administration, the age, body weight, and general health of the subject. Ultimately, the attending physician or veterinarian will decide the appropriate amount and dosage regimen. Such amount is referred to as an "effective" amount.

By "expression vector" is meant a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as plasmids, cosmids, and viruses that incorporate the recombinant polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like.

By "fragment" is meant a portion of a polypeptide or nucleic acid molecule. This portion contains, preferably, at least 10%, 20%, 30%, 40%, 50%, 60%, 70%, 80%, or 90% of the entire length of the reference polypeptide or nucleic acid molecule. A fragment may contain 5, 10, 15, 20, 30, 40, 50, 60, 70, 80, 90, or 100 amino acids or nucleotides.

The term "human-derived bacteria" means bacterial species that have been isolated from a fecal sample or from a gastrointestinal biopsy obtained from a human individual or whose ancestors were isolated from a fecal sample or from a gastrointestinal biopsy obtained from a human (e.g., are progeny of bacteria obtained from a fecal sample or a gastrointestinal biopsy). For example, the bacterial species may have been previously isolated from a fecal sample or from a gastrointestinal biopsy obtained from a human and cultured for a sufficient time to generate progeny. The progeny can then be further cultured or frozen. The human-derived bacteria are naturally occurring commensals that populate the gastrointestinal tract of human individuals, preferably healthy human individuals.

The terms "isolated," "purified," or "biologically pure" refers to material that is free to varying degrees from components which normally accompany it as found in its native state. "Isolate" denotes a degree of separation from original source or surroundings. "Purify" denotes a degree of separation that is higher than isolation. Thus, a purified isolated bacterium that is part of a culture or inoculum is at least about 90%, 95% or 100% free of bacteria, fungi, viruses, or other undefined microbes.

By "marker" is meant any analyte associated with a disease or disorder.

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

"Pharmaceutically acceptable" refers to those properties and/or substances that are acceptable to the patient from a pharmacological/toxicological point of view and to the manufacturing pharmaceutical chemist from a physical/ chemical point of view regarding composition, formulation, stability, patient acceptance and bioavailability. "Pharmaceutically acceptable carrier" refers to a medium that does not interfere with the effectiveness of the biological activity of the active ingredient(s) and is not toxic to the host to which it is administered.

As used herein, the term "pharmaceutical composition" or "pharmaceutically acceptable composition" refers to a mixture of at least one compound or molecule useful within the invention with a pharmaceutically acceptable carrier. The pharmaceutical composition facilitates administration of the compound or molecule to a patient. Multiple techniques of administering a compound or molecule exist in the art including, but not limited to, intravenous, oral, aerosol, parenteral, ophthalmic, pulmonary, rectal and topical administration.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound or molecule useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound or molecule useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

By "reference" is meant a standard or control condition.

A "reference sequence" is a defined sequence used as a basis for sequence comparison.

By "subject" is meant a mammal, including, but not limited to, a human or non-human mammal, such as a bovine, equine, canine, ovine, or feline.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95%, 96%, 97%, 98%, or even 99% or more identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

DETAILED DESCRIPTION OF THE INVENTION

The invention provides a probiotic human-derived lactic acid bacteria (LAB) (e.g., *Lactobacillus*) expressing a chimeric nucleic acid molecule, and its use for colonizing the gut or digestive tract of a subject to treat CDI. The invention also provides a method of treating or preventing *Clostridium difficile* infection and colonization. The invention features use of the probiotic bacteria of the invention for the replacement of a gut microbiome associated with disease.

The invention is based, at least in part, on the discovery that expression of a chimeric SlpA from *Clostridium difficile* and *Lactobacillus acidophilus*, in an engineered LAB (e.g. *Lactobacillus acidophilus*) is effective for colonizing the gut with the engineered LAB. It was also found that the engineered LAB of the invention protected the gut from virulent *Clostridium difficile* challenge. These findings indicate that administration of an engineered LAB expressing a chimeric SlpA from *Clostridium difficile* and *Lactobacillus acidophilus* is useful for treating or preventing *Clostridium difficile* infection and colonization.

Compositions

Surface-Layer Protein a (SlpA) and Expression Thereof

Many gram-positive bacteria including *C. difficile* possess a surface-layer that covers the peptidoglycan-rich cell wall. The most abundant Surface layer protein in *C. difficile* is slpA, a major contributor of adhesion to, and colonization of, intestinal epithelial cells. (Merrigan et al. PLoS ONE 8(11): e78404,2013). SlpA plays a major role in *C. difficile* infection, and that it may represent an attractive target for interventions aimed at abrogating gut colonization by this pathogen.

In one aspect, the invention provides a chimeric nucleic acid molecule comprising a nucleic acid sequence comprising a phosphoglycerate mutase (pgm) strong constitutive promoter (pgm promoter) and a nucleic acid sequence encoding a bacterial surface layer protein A (SlpA) consisting of a *Clostridium difficile* derived host-cell binding domain and a lactic acid bacterium (LAB) derived peptidoglycan anchor. In some embodiments, the LAB is a *Lactobacillus* species selected from the group consisting of *Lactobacillus acidophilus* or *Lactobacillus casei*. In some embodiments, the nucleic acid sequence comprising the pgm promoter and the nucleic acid sequence encoding the chimeric SplA gene from *Clostridium difficile* and *Lactobacillus acidophilus* has the following sequence (SEQ ID NO: 18):

TTATCTAAAGTTTGCAACCTTAACGTAAGTCTTGTCAGTGTTGTCACCGA

TCTTGTAGTACTTTTGGCCGTTCTTGAATGTGTATGAAGCACCGTAAGTA

GTTACAACTTCACCCTTCTTCAATACAACCTTGTTAGCACGCTTCTTTGA

TGATGCGTAAACGTAAGCGTTGTGCTTCAAAGTACGCTTAGTACCATCGA

TGTTTGCAGCGTTGATGTACTTGTCAACAGCCTTACCGTTTTCAACTACT

TGGTAGTAAGTCTTACCGTTGATAGTAGTAGTGTTTGGCAATACGCTTAC

-continued

TGAGTTGTAACGCTTAACGCTGTCAGTACCAACACGCTTAGCGTCCTTGT

CGTAGTAGTATGCGTTGTGCATAATTCTCTTGCTTACGCTGGCTACAGTT

GGCTCAGCAACATTAGGAACAGTAACAACTACTGGCAAAGTAGCTGACTT

ACCATTAGTATTTGATGCTAAATCTGTATCATCTTTAGTCACAAACCCAC

TTACGGCAACTGCACTCGGTGTACTACCACCAGTTACATCAACTTTAAGG

GTTTTGTTGAAATCAATAGTTGTTCCTTTGCCTGCATATTCTAAACCTGT

TGATGGAAGATTGATTGCAATACCAGCTGTAGAATCACCTACTTTACCAT

ACTTATCTTCAACAGCACCCGCTTTCATTTCGACAACATATCCGGTATCT

TCACTACCTCCACTCTTTAAGCCAAAAGTTGCCACATCTTTTACTTTTAA

CGCTTTTGTTGCCGCAACATTCTTTCCTTCAGAATCCTGCGTTTTAGACA

CCATTCCAAACGTATCTTTAGTTGCAATATCAATTAGCGTCTTTTCATTT

AACGAATTCAATTTAGTAACAATAGCTTCGGCATCGGCTTGATTGGTGAT

AATCTTATTCTCTAGATTGTAATCAACAGAAAAATCTACATAATCGCCAT

CGCCTAATTTGTCTAATTGTGTATTTACAAGATTATACAACTTTTCTGCG

GCTGCATCTCGATCTGCTTTCTTATTCGCTGATTTAGGTGCTACTTCTCC

TACCACACCATCATTGAAACTGACCGTAATCTTACCAATACTATTATCTT

TAAGTCCATCTTGTAATTGTTTGACAGCCTTTTTCCAATCATTCTTAACC

ACCGTATAGCCTTGTGTACCAGTGGTTGCAGCAAATACAGGTGCAGCAGC

GCTAACAGTAGATACAGCAGAAGCAGCAACTGGAGCAACAGCAAGTAAAG

CAGCAGCAGCAGCGCTAACGATTCTTAAATTTTTCTTCATGGATCCATAT

GCACGTCGACGCGCCTGCAGAAGCTTCGAATTCTGCCTTCTGAGCTTCTT

CAACACCTTTTTCTGAAAGGTTAACGTCAACCCAACCAGTAAATTGGTTT

GAAAGGTTCCATTCACTTTGACCGTGACGGATTAAAACTAATTTTGACAT

GAAATATCTCCTTTTAAATTCAATGTTTCATCCATATTTTACACATTTCA

CAGTTTTTTCATAGAGATATGGGCAAAAAAACATCTTTTTTTATTTCTA

CTTTTTATTTTCTGCTTTTTTGTGCTAACTTATAACAAGCATAC

In another aspect, the invention provides a chimeric polypeptide encoded and expressed by the nucleic acid sequence described above herein.

Expression of a Chimeric Polypeptide

In order to express the chimeric polypeptide of the invention, DNA molecules obtained by any of the methods described herein or those that are known in the art, can be inserted into appropriate expression vectors by techniques well known in the art. For example, a double stranded DNA can be cloned into a suitable vector by restriction enzyme linking involving the use of synthetic DNA linkers or by blunt-ended ligation. DNA ligases are usually used to ligate the DNA molecules and undesirable joining can be avoided by treatment with alkaline phosphatase.

Therefore, the invention includes vectors (e.g., recombinant plasmids) that include nucleic acid molecules (e.g., genes or recombinant nucleic acid molecules encoding genes) as described herein. In some embodiments, the vector of the invention is a recombinant vector (e.g., plasmid, phage, phasmid, virus, cosmid, fosmid, or other purified nucleic acid vector) that has been altered, modified or engineered such that it contains greater, fewer or different nucleic acid sequences than those included in the native or natural nucleic acid molecule from which the recombinant vector was derived. For example, a recombinant vector may include a nucleotide sequence encoding an SlpA chimeric polypeptide operatively linked to regulatory sequences, e.g., promoter sequences, terminator sequences, and the like, as defined herein. Recombinant vectors which allow for expression of the genes or nucleic acids included in them are referred to as "expression vectors."

In one aspect, although the pgm promoter is exemplified herein, the invention should not be construed to be limited solely to this promoter sequence. In certain embodiments, promoter sequences that are useful in the invention include any promoter known in the art that induces high levels of expression of the gene of interest.

The vector may also include conventional control elements which are operably linked to a gene of interest in the vector (e.g. a heterologous gene) in a manner which permits its transcription, translation and/or expression in a cell infected with the vector produced by the invention (i.e. pMGM15).

As used herein, "operably linked" sequences include both expression control sequences that are contiguous with the gene of interest and expression control sequences that act in trans or at a distance to control the gene of interest. Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. There are numerous expression control sequences, including promoters which are native, constitutive, inducible and/or tissue-specific, are known in the art that may be used in the compositions of the invention.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, individual elements may function either cooperatively or independently to activate transcription.

In one embodiment, a suitable promoter is the pgm promoter sequence. This promoter sequence is a strong constitutive promoter sequence capable of driving high levels of expression of any polynucleotide sequence operatively linked thereto. However, other bacterial constitutive promoter sequences may also be used, including, but not limited to the T7 promoter and Sp6 promoter. Further, the invention should not be construed to be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a Lac promoter, an araBAD promoter, and a pL promoter.

In order to assess the expression of the heterologous gene of interest (e.g. chimeric SlpA), the expression vector to be introduced into a cell can also contain either a selectable marker gene or a reporter gene or both to facilitate identification and selection of expressing cells from the population of cells sought to be transformed through the vector (e.g. pMGM15). In other aspects, the selectable marker may be carried on a separate piece of DNA and used in a transformation/protoplating/electroporation procedure. Both selectable markers and reporter genes may be flanked with appropriate regulatory sequences to enable expression in the host cells. Useful selectable markers include, for example, antibiotic-resistance genes, such as the chloramphenicol resistant gene and the like.

Reporter genes are used for identifying potentially infected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Suitable reporter genes may include genes encoding luciferase, beta-galactosidase, chloramphenicol acetyl transferase, secreted alkaline phosphatase, or the green fluorescent protein gene such as ytvA from *B. subtilis* (Ui-Tei et al., 2000 FEBS Letters 479: 79-82).

In some of the molecules of the invention described herein, one or more DNA molecules having a nucleotide sequence encoding one or more polypeptides of the invention are operatively linked to one or more regulatory sequences, which are capable of integrating the desired DNA molecule into a prokaryotic host cell. Cells which have been stably transformed by the introduced DNA can be selected, for example, by introducing one or more markers which allow for selection of host cells which contain the expression vector. A selectable marker gene can either be linked directly to a nucleic acid sequence to be expressed, or be introduced into the same cell by co-transfection. Additional elements may also be needed for optimal synthesis of proteins described herein. It would be apparent to one of ordinary skill in the art which additional elements to use.

Factors of importance in selecting a particular vector include, but are not limited to, the ease with which recipient cells that contain the vector are recognized and selected from those recipient cells which do not contain the vector; the number of copies of the vector which are desired in a particular host; and whether it is desirable to be able to "shuttle" the vector between host cells of different species.

Once the vector(s) is constructed to include a DNA sequence for expression, it may be introduced into an appropriate host cell by one or more of a variety of suitable methods that are known in the art, including but not limited to, for example, transformation, transfection, conjugation, protoplast fusion, electroporation, calcium phosphate-precipitation, direct microinjection, etc.

After the introduction of one or more vector(s), host cells (e.g. *Lactobacillus* sp.) are usually grown in a selective medium, which selects for the growth of vector-containing cells. Expression of recombinant proteins can be detected by immunoassays including Western blot analysis, immunoblot, and immunofluorescence. Purification of recombinant proteins can be carried out by any of the methods known in the art or described herein, for example, any conventional procedures involving extraction, precipitation, chromatography and electrophoresis. A further purification procedure that may be used for purifying proteins is affinity chromatography using monoclonal antibodies which bind a target protein. Generally, crude preparations containing a recombinant protein are passed through a column on which a suitable monoclonal antibody is immobilized. The protein usually binds to the column via the specific antibody while the impurities pass through. After washing the column, the protein is eluted from the gel by changing pH or ionic strength, for example.

In one aspect, the invention provides a vector comprising a nucleic acid sequence comprising: (a) a chimeric surface layer protein A (slpA) gene of *Lactobacillus. acidophilus* and *Clostridium difficile*; (b) a phosphoglycerate mutase (pgm) constitutive promoter; (c) an ytvA fluorescent allele from *B. subtilis*; (d) a temperature sensitive repA gene; (e) a chloramphenicol resistance cat gene; (0 an internal fragment of *Lactobacillus acidophilus* thymidylate synthase A (thyA); and, (g) an internal fragment of *Lactobacillus casei* thyA.

In some embodiments, the vector is a *Lactobacillus* expression vector. In some embodiments, the vector is pMGM15. In other embodiments, the vector has a nucleic acid sequence of SEQ ID NO: 1 (as detailed in FIG. 1).

In one aspect the invention provides an engineered cell comprising the chimeric nucleic acid molecule described above herein.

In one aspect the invention provides an engineered cell comprising the vector described above herein.

In some embodiments, the chimeric nucleic acid molecule or the nucleic acid sequence encoding the vector is integrated into the chromosome of the engineered cell. In some embodiments, the engineered cell is a human-derived *Lactobacillus*, a human-derived *Lactobacillus acidophilus*, or a human-derived or milk-derived *Lactobacillus* casei.

Therapeutic Compositions

The invention features engineered probiotic bacteria expressing *Clostridium difficile* SlpA or fragment thereof (e.g., chimeric SlpA). In particular, *Clostridium difficile* SlpA, or fragment thereof, is expressed in lactic acid bacteria (LAB) particularly *Lactobacillus* cells (e.g., *Lactobacillus acidophilus* or *Lactobacillus casei*). In additional embodiments, one or more strains of probiotic bacteria expressing a chimeric SlpA polypeptide are administered or formulated as a therapeutic composition. In certain embodiments, the SlpA expressed is a chimeric SlpA comprising a *C. difficile* SlpA variable domain and *Lactobacillus* (e.g., *Lactobacillus acidophilus* or *Lactobacillus casei*) SlpA cell wall binding domain. The SlpA additionally includes a bacterial secretion signal that is appropriate for surface expression in its host cell (e.g., Lactoccocus, *Lactobacillus, Lactobacillus acidophilus* or *Lactobacillus casei*). In various embodiments, the invention also includes nucleic acid molecules and vectors encoding a chimeric SlpA polypeptide. Vectors encoding the chimeric SlpA polypeptide can be used to direct or regulate the expression of the chimeric SlpA by the cell (see e.g., Duong et al., Microbial Biotechnology 2010, 4(3): 357-367 which is herein incorporated in its entirety by reference). Such vectors contain one or more origin of replication sequences that can be used by a bacterial cell, promoter sequences for expression in a bacterial cell (e.g., constitutive or inducible), genetic markers for selection (e.g., antibiotic resistance); origin of transfer sequences for bacterial conjugation (e.g., traJ), and may also be codon optimized for protein expression.

Alternatively, nucleic acid sequences encoding chimeric SlpA may be integrated into the *Lactobacillus* genome. In certain embodiments, nucleic acid sequences encoding the chimeric SlpA can be integrated into the *Lactobacillus* genome through recombination between vectors comprising the nucleic acid sequence encoding the chimeric SlpA poly peptide and bacterial chromosome. Such techniques are well known in the art (see e.g., Leenhouts, et al., Appl. Environ. Microbiol. 1989, 55(2): 394-400, and Gaspar, et al., Appl. Environ. Microbiol. 2004, 70(3): 1466-74 which are herein incorporated in their entirety by reference).

Probiotic strains may also be engineered with auxotrophic selection, for example requiring thiamine or thymine supplementation for survival.

Methods of the Invention

The present invention provides methods of treating diseases or symptoms thereof associated with the presence of one or more undesirable bacteria in the gut of a subject (e.g. *C. difficile*). Accordingly, the invention provides compositions and methods for treating a subject having or at risk of developing a disease associated with undesirable changes in the gut microbiome, the method involving administering a therapeutically effective amount of a composition comprising a engineered probiotic lactic acid bacterium (LAB) of the invention to a subject (e.g., a mammal, such as a human). In particular, the compositions and methods of the invention are effective for treating or preventing *Clostridium difficile* infection, colonization, or diseases and symptoms thereof (e.g., diarrhea). Without wishing to be bound by theory, an engineered *Lactobacillus* expressing the chimeric *Clostridium difficile/Lactobacillus acidophilus* SlpA of the invention can colonize the gut and compete with *Clostridium difficile* for binding and colonization. Accordingly, the method includes the step of administering to a mammal a therapeutic amount of an amount of a composition comprising one or more engineered cell (i.e. LAB) the invention sufficient to treat the disease or disorder or symptom thereof, under conditions such that the disease or disorder is treated.

In one aspect the invention provides a method of treating or preventing *Clostridium difficile* infection in a mammal. The method comprises administering an engineered LAB expressing the vector as described above herein, thereby treating or preventing *Clostridium difficile* infection in the mammal.

In yet another aspect the invention provides, a method of colonizing the gut of a mammal with an engineered LAB. The method comprises administering an engineered LAB expressing the vector as described above herein, thereby colonizing the gut of the mammal with the engineered LAB.

In some embodiments, the administered engineered LAB is selected from the group consisting of a human-derived *Lactobacillus*, a human-derived *Lactobacillus acidophilus*, and a human-derived *Lactobacillus* casei.

Identifying a subject in need of treatment for a disease associated with the gut microbiome can be conducted by a health care professional and can be subjective (e.g. opinion) or objective (e.g. measurable by a test or diagnostic method). In certain embodiments, the subject has undergone or is undergoing treatment with antibiotics. As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated. As used herein, the terms "prevent," "preventing," "prevention," "prophylactic treatment" and the like refer to reducing the probability of developing a disorder or condition in a subject, who does not have, but is at risk of or susceptible to developing a disorder or condition.

The therapeutic methods of the invention (which include prophylactic treatment) in general comprise administration of a therapeutically effective amount of a composition comprising the probiotic bacteria of the invention to a subject (e.g., human) in need thereof. Such treatment will be suitably administered to subjects, particularly humans, suffering from, having, susceptible to, or at risk for a disease, disorder, or symptom thereof. Determination of those subjects "at risk" can be made by any objective or subjective determination by a diagnostic test or opinion of a subject or health care provider. The compositions herein may be also used in the treatment of any other disorders in which a microbial imbalance in the digestive tract may be implicated.

Methods of Delivery

One skilled in the art will recognize that although more than one route can be used for administration, a particular route can provide a more immediate and more effective reaction than another route.

Routes of administration of any of the compositions of the invention include inhalational, oral, nasal, rectal, parenteral, sublingual, transdermal, transmucosal (e.g., sublingual, lingual, (trans)buccal, (trans)urethral, vaginal (e.g., trans- and perivaginally), (intra)nasal, and (trans)rectal), intravesical, intrapulmonary, intraduodenal, intragastrical, intrathecal, subcutaneous, intramuscular, intradermal, intra-arterial, intravenous, intrabronchial, inhalation, and topical administration. Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

In one embodiment, the compositions comprising the engineered cell (LAB) of the invention may be administered orally, rectally, or enterally. Preferably the compositions are administered to a subject in tablet form, by feeding tube, by enema, or by colonoscopy. Preferably, the probiotic bacteria of the invention are diluted in a suitable excipient (e.g., saline solution). A non-limiting example of an effective dose may include $10^6$-$10^9$ colony forming units of bacteria per day). In some embodiments, the engineered cell of the invention is administered orally. In some embodiments, the engineered cell is administered daily as needed.

Kits

The invention provides kits for colonizing probiotic engineered LAB of the invention in the gut of a mammalian host (such as a human). The invention also provides kits for the treatment or prevention of *Clostridium difficile* infection or colonization. In particular embodiments, the kit comprises a sterile container which contains a therapeutic or prophylactic composition comprising the engineered LAB of the invention; such containers can be boxes, ampoules, bottles, vials, tubes, bags, pouches, blister-packs, or other suitable container forms known in the art. Such containers can be made of plastic, glass, laminated paper, metal foil, or other materials suitable for holding medicaments.

The kit preferably contains instructions that generally include information about the use of the composition for the expansion of the microbial consortia in the gut of the subject. The kit further contains precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

Examples

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

The Materials and Methods used in the performance of the experiments disclosed herein are now described.

Cell lines. The human intestinal epithelial cell line C2BBe, a brush border-expressing Caco-2 sub-clone (Peterson et al (1992), J Cell Sci, 102 (Pt 3), 581-600), was used in this study and cultured as previously reported (Roxas et al., 2014, Am J Physiol Gastrointest Liver Physiol 307(3), G374-380).

Bacterial Strains and plasmids. All strains and plasmid are described in Table 1. Lactic acid bacteria were purchased from the American Type Culture Collection (ATCC, Manassas, Va.). Specifically, *Lactobacillus casei* strain 334 [Orla-Jensen; (Dellaglio et al., 2002, Int J Syst Evol Microbiol, 52(Pt 1), 285-287), and *Lactobacillus acidophilus* strain 4356 (Roussel et al., 1993, Appl Bacteriol 74(5), 549-556) were used for these studies. Lactic acid bacteria were grown in De Man, Rogosa and Sharpe (MRS) broth (Duong et al., 2011, Microb Biotechnol, 4(3), 357-367) and incubated at 30° C. in the presence of 5% CO2. Bacteria were cultured for 3-5 days to reach saturation [>1.0×108 colony forming units (CFU) per mL].

*L. acidophilus* and *L. casei* strains ferment the dextrose in MRS to distinct products, and the corresponding pH changes can be detected by including bromophenol blue into the media (MRS-BPB)(Lee et. al., 2008, Lett Appl Microbiol 46(6), 676-681). *L acidophilus*, a homo-fermenter, metabolizes dextrose to lactic acid, and the plates remain violet/blue (pH>4.6); *L. casei*, a hetero-fermenter converts dextrose to acetic acid, and the drop in pH (<3.0) results in a color change to yellow/white. Further, *L. casei*, unlike *L. acidophilus*, can ferment mannitol, and this can be verified by growth on Purple Broth Base (Difco™ Becton, Dickinson and Company Sparks, MD); the acidic change resulting from mannitol fermentation causes the pH indicator bromocresol purple to turn yellow.

The slpA *C. difficile/L. acidophilus* "chimera" fragment was designed with a strong lactic-acid-bacterial (LAB) promoter [endogenous to the phosphoglycerate mutase (pgm) gene in plasmid pTRK848 (Duong et al., 2011, Microb Biotechnol, 4(3), 357-367), a lactic-acid-bacterial Shine-Dalgarno (ribosome binding site) sequence (Duong et al., 2011, Microb Biotechnol, 4(3), 357-367), a signal sequence from a *Lactobacillus acidophilus* S-layer protein, a codon-optimized *C. difficile* strain 630 host-cell-binding fragment, and the *L. acidophilus* SlpA-ortholog cell-wall-binding domain (Michon et al., 2016, Microb Cell Fact 15, 70). The entire fragment (F1) was chemically synthesized (DNA 2.0, now ATUM, Newark, Calif.), and cloned into the DNA 2.0 maintenance vector pJ241 to yield pMGM13. A second DNA fragment (F2) comprising a broad host-range temperature-sensitive origin of replication (repA), and a chloramphenicol resistance gene (catP) was also chemically synthesized based on sequence information obtained from the broad host-range plasmid [pKS1(Steen et al., 2010, Nature 463(7280), 559-562)]. This fragment was self-ligated to form pMGM11 ("empty vector"). The two synthesized fragments F1 and F2 harbored PmeI and FseI restriction sites at their termini; following digestion with those enzymes, linear F1 and F2 were ligated using T4 DNA ligase (Sigma, St. Louis Mo.) to generate pMGM14. Plasmid integrity of pMGM14 was confirmed by complete DNA sequencing. All plasmids were transformed into *E. coli* strains DH10b, TOP10 or NCK1753 for maintenance or propagation purposes, or into *E. coli* GCS prior to extraction for electroporation. All plasmids were PCR-verified prior to any use in lactic acid bacteria.

Lactic acid bacterial (LAB) transformation. The pMGM14 plasmid described above was first extracted from the *E. coli* storage strain, and 10 μg used for each LAB transformation. *Lactobacillus acidophilus* strain 4356 and *Lactobacillus* casei 343 were propagated in Mann-Rogosa-Sharpe (MRS) medium (Remel, Lenexa, Kans.) per the method of Walker et al. (Walker et al., 1996, FEMS Microbiol Lett 138(2-3), 233-237) and Kim et al. (Kim et al., 2005, Anaerobe 51, 42-46). In brief, LAB strains were grown to saturation at 37° C. in 5% CO2, sub-cultured at a 1:50 dilution, and re-grown using the same process two more times. To shear cell-wall proteins, and prepare the resulting protoplasts for electroporation, a fourth sub-culture was grown for 15 hours in MRS supplemented with 1% glycine, and then sub-cultured in the same medium at a 1:50 dilution for an additional 6 hours. Bacteria were harvested using centrifugation, and chilled pellets subjected to electroporation with 10 μg plasmid DNA, followed by recovery in MRS broth for 3 hours, and growth on MRS-agar+5 μg/mL chloramphenicol (Sigma, St. Louis, Mo.) at 30° C. in 5% CO2. Plasmid was extracted from one-half of a colony of multiple purified transformants, and verified via DNA sequence analysis. The remaining bacterial colonies were propagated in the presence of chloramphenicol at 42° C., the non-permissive temperature, at which repA is non-functional, thus selecting for integrants. For pMGM14-based transformants, putative integrants were purified, and assessed for chimeric slpA presence by PCR. All confirmations were performed at the non-permissive temperature. Three independently-isolated and PCR-verified identical transformants were bio-banked for the *L. casei* strain (herein referred to as Syn-LAB 2.0 clones), and seventeen independently-isolated and PCR-verified identical transformants for the *L. acidophilus* strain (herein referred to as Syn-LAB 2.1 clones). For in vitro studies only, all LAB strains were propagated at the non-permissive temperature with antibiotic selection as appropriate (5 μg/mL chloramphenicol). However, for all in vivo studies, while strains were propagated as above, no selection antibiotic was administered to the animals.

An identical procedure was used to generate empty-vector harboring LAB strains (Table 1); these strains were PCR-verified, and used only for in vivo studies. Plasmids were maintained episomally; the lack of homology with the LAB host limited the possibility of integration of vector sequences into the chromosome.

Transepithelial electrical resistance (TEER) measurements. Polarized human intestinal epithelial cells [C2BBe; (Peterson et al., 1992, J Cell Sci 102 (Pt 3), 581-600.)] were grown on 0.33-cm2 collagen-coated Corning™ Transwells (Thermo Fisher Scientific) for 14 days. Monolayers were treated apically with 1.42×107 cfu/well and 1.96×107 cfu/well of parental and Syn-LAB 2.0 respectively. Measurements were made every hour for 7 hours, and at 24 hours post-treatment using an epithelial volt-Ohm voltmeter (World Precision Instruments, Sarasota, Fla.), and TEER calculated by applying Ohm's Law. An identical setup was used when testing Syn-LAB 2.1 and its *L. acidophilus* parent strain.

Host cell survival measurement. C2BBe monolayers were treated with media alone, the parent LAB strain, or the corresponding Slp chimera-expressing Syn-LAB derivatives, and host cell viability was assessed using the propidium iodide (PI) uptake assay as described previously (Roxas et al., 2012, Infect Immun 80(11), 3850-3857). Briefly, PI (2 μg/ml; Molecular Probes) was added to the treated cells, and fluorescence measured after 30 minutes using a microplate reader (Synergy HT; BioTek instruments, Winooski, Vt.). To estimate maximal PI uptake, a set of wells were treated with 70% methanol prior to PI treatment.

Immunoblot Analyses. Surface layer proteins (Slp) were extracted from *Lactobacillus* parent and Syn-LAB strain saturated cultures (OD600 nm=1.5) using 0.2M glycine (pH2.2), as described by Calabi et al (Calabi et al., 2001, Mol Microbiol 40(5), 1187-1199). For dot blot analyses, 31.25 ng, 62.5 ng, 125 ng, 500 ng, 1 μg and 2 μg of total protein were blotted on nitrocellulose membranes (Bio-rad, Richmond, Calif.). Slp extracts (5-10 μg) were also separated on 4-20% TGXTM pre-cast protein gels (Bio-rad, Richmond, Calif.). Separated proteins were transferred to 0.2-pin nitrocellulose membranes (Transblot Cell Apparatus, Bio-Rad). Blots were blocked with 5% nonfat milk in Tris-buffered saline containing Tween 20 (TBST) for 1 hour, incubated with antiserum specific to *C. difficile* SlpA (raised against the *C. difficile* strain 630 SlpA (Merrigan et al., 2013, PLoS One 8(11), e78404) overnight at 4° C. and in horseradish peroxidase-conjugated goat anti-rabbit antibody for 1 hour at room temperature (Sigma-Aldrich, St. Louis, Mo.). Membranes were washed five times for 5 minutes in blocking solution between each incubation step and developed with SuperSignal West Femto Chemiluminescent Substrate (ThermoFisher Scientific, Rockford, Ill.).

Immunofluorescence Microscopy. SlpA chimera expression in *L. casei* WT and Syn-LAB 2.0 and Syn-LAB 2.1 strains was evaluated via immunofluorescence staining using antiserum specific to *C. difficile* SlpA. *Lactobacillus* sp cultures were allowed to settle for 10 minutes in 12-well plates with poly-L-lysine-coated coverslips. Unattached bacteria were removed, and samples were fixed with 4% paraformaldehyde in PBS (pH 7.4) for 20 minutes, permeabilized with 0.2% Triton X-100 in PBS for 15 minutes, quenched with 50 mM NH4Cl and 0.125M glycine in PBS for 15 minutes, and blocked with 5% IgG-free bovine serum albumin (BSA) in PBS for 1 hour. Samples were incubated with antiserum specific to *C. difficile* SlpA overnight at 4° C., and then washed three times with 1% IgG-free BSA in PBS. Secondary antibodies (Alexa 488-conjugated goat anti-rabbit IgG antisera; Thermo Fisher Scientific, Waltham, Mass.) were added at 8 µg/ml in 5% IgG-free BSA for 1 hour. Samples were mounted in ProLong Diamond Antifade reagent (Thermo Fisher Scientific, Waltham, Mass.). Intestinal tissue samples (ileum, cecum, and colon) from LGV Golden Syrian Hamsters (Charles River Laboratories, San Diego, Calif.) treated with Syn-LAB 2.0 were frozen in OCT embedding medium (Tissue-Tek, Sakura Finetek, CA) and stored at −80° C. OCT-mounted tissue samples cut at 3 micron thickness were fixed in 4% paraformaldehyde in PBS (pH 7.4) for 20 minutes, and processed for SlpA immunofluorescence staining as described above. Samples were stained with 4,6-diamidino-2-phenylindole (DAPI) prior to mounting in ProLong Diamond Antifade reagent. Images were captured using EVOS® FL Imaging System (Thermo Fisher Scientific, Waltham, Mass.) or DeltaVision Elite Deconvolution Microscope (GE Healthcare, Pittsburgh, Pa.).

Flow cytometry. Parent and transformed *Lactobacillus* sp strains were cultured in MRS broth as described above, and subjected to Gram's staining to verify purity and morphology. Bacteria were pelleted by centrifugation at 4000 g for 2 minutes. Bacterial pellets were washed gently three times with blocking solution (2% IgG-free BSA in PBS) and then incubated with antiserum specific to *C. difficile* SlpA for 30 minutes. Secondary antibodies (Alexa Fluor 555-conjugated goat anti-rabbit IgG antisera; Thermo Fisher Scientific, Waltham, Mass.) were added at 8 µg/ml in 2% IgG-free BSA for 30 minutes. Samples were washed three times with blocking solution after each antibody incubation step. Stained samples were re-suspended in blocking solution at 106 cells/mL density and analyzed via flow cytometry using a BD FACSCANTO II machine (BD Biosciences, San Jose, Calif.). List mode data files consisting of 10,000 events gated on FSC (forward scatter) vs SSC (side scatter) were acquired and analyzed using FACSDiva 8.0.1 software (BD Biosciences, San Jose, Calif.). Appropriate electronic compensation was adjusted by acquiring the cell populations stained with the fluorophore, as well as an unstained control.

Golden Syrian hamster studies. All hamster studies were approved by the Institutional Animal Care and Use Committee of the University of Arizona. The Golden Syrian hamster model was employed to study both colonization/shedding and protection conferred by Syn-LAB strains. For all studies, male hamsters (6-8 weeks; 90-110 g weight) were used. Shedding studies: Prior to any treatment, hamster stool plated on MRS yielded no colonies, confirming that the animals were devoid of endogenous *Lactobacillus* bacteria. Animals received a daily dose of 108 Syn-LAB 2.0 or 108 Syn-LAB 2.1 respectively. Feeding and enumeration were continued for six days. For Syn-LAB 2.0-treated animals only, oral clindamycin (prescription solution; clindamycin sulfate; University of Arizona Pharmacy; 30 mg/kg) was administered on Day 4, and LAB detection monitored until Day 6. Fecal pellets were collected daily, and pellets were re-suspended in PBS, homogenized, serially diluted and plated on the appropriate Syn-LAB selective medium containing chloramphenicol. Colonies were detected only in stool samples from Syn-LAB-treated animals, and not from untreated controls. Shedding from all animals was statistically indistinguishable. For added confirmation, select colonies were 16S PCR-verified for *L. casei* as well as the presence of the chimeric slpA.

Challenge studies: These were performed in two modalities, a "fixed-dose" and a "continuous dose" format. All animals received clindamycin (prescription solution; clindamycin sulfate; University of Arizona Pharmacy; 30 mg/kg). 1000 spores of *C. difficile* strain CD630 was used in the challenge studies where indicated, and 108 CFU LAB was used wherever indicated. Group 1 animals received clindamycin on day −3 but no other intervention (black line in FIGS. 15A and 15B). Group 2 hamsters received clindamycin (day −3) and *C. difficile* challenge (day 0), but no LAB treatment (FIGS. 15A and B). Group 3 hamsters received *L. casei* parent strain/empty vector on days −6, −5, −4, −2, −1 and 0, and clindamycin on day −3, followed by *C. difficile* challenge on day 0 (FIGS. 15A and 15B). Group 4 hamsters received Syn-LAB 2.0 on days −6, −5, −4, −2, −1 and 0, clindamycin on day −3, and *C. difficile* challenge on day 0 (FIGS. 15A and 15B).

For continuous-dose studies, the clindamycin dose and timing was similar to that above, and only the "*C. difficile*", "Empty Vector" and "LAB" groups as above were evaluated. Both "Empty Vector" and Syn-LAB 2.0 ("LAB") were continuously dosed at 108 CFU per animal per day starting at Day −6 before infection, until death/euthanasia.

Where appropriate, infections commenced 72 hours post-antibiotic administration, and the challenge strain used was *C. difficile* strain 630 (1000 spores; orally administered in PBS). Animals monitored for disease symptoms (wet-tail, ruffled coat, lethargy) through the course of the studies. Moribund hamsters or those meeting the criteria for euthanasia were administered 270 mg/kg commercial euthanizing solution (Euthanasia III, MedPharma Inc, Pomona, Calif.). Euthanized hamsters were dissected for visualization of gross pathology, and cecal contents harvested and plated on selective medium for recovery and molecular typing of *C. difficile* (using 16s-23s rDNA intergenic fragment profiling and comparison with the organisms used for infection). In all studies, and all groups, fecal pellets were also collected daily, re-suspended in PBS, homogenized, serially diluted and plated on *C. difficile* or *L. casei* selective medium as appropriate.

Immune response studies. For these experiments, age- and weight-matched Golden Syrian hamsters (at least 3 per group) were administered 108 CFU Syn-LAB 2.0 daily, or left untreated, for 21 days. Animals were then euthanized, whole blood harvested via cardiac puncture, and serum immediately retrieved after blood was centrifuged at 1000 g for 10 minutes. This material was aliquoted and stored at −80 C until further use. For immune response assessments, the same methodology as immunoblotting above was used, but serum from Syn-LAB or mock-treated animals was used as the source of primary antibody.

Neonatal piglet studies. All piglet studies were approved by the Institutional Animal Care and Use Committee of the University of Arizona; we assessed Syn-LAB 2.1 safety, tolerability and efficacy in protecting against *C. difficile* challenge. Newborn male and female piglets were obtained via assisted delivery from a local antibiotic-free, small-volume farm, and transferred to the University of Arizona Central Animal Facility within 2 hours of birth. On Day 2 post-birth, piglets were treated with oral vancomycin (50 mg/kg; prescription solution, University of Arizona Pharmacy) to ablate any pre-existing *C. difficile* colonization. On day 6 post-birth, piglets were administered 1010 Syn-LAB 2.1 in milk replacer every 8 hours. On day 7, a subset of animals was administered a non-lethal dose of 1000 *C. difficile* spores of strain 630. Monitoring included checks every 8 hours thereafter, with weight, stimulus response and dehydrations scores recorded. Upon completion of the study, piglets were anaesthetized with Ketamine/Xylazine, and then humanely euthanized with commercial euthanizing solution (Euthanasia III, MedPharma Inc, Pomona, Calif.) followed by cardiac puncture. Histologic analyses included standard hematoxylin-eosin staining of colonic tissues following standard methodologies (Kiernan, 2008, theory and practice, 4th edition), and immunofluorescence staining of tissues with anti-*C. difficile* SlpA serum as described in detail above for visualization of Syn-LAB 2.0.

Statistical analysis. Multiple statistical tests were employed and utilized the Excel-Stat application to determine significance for experiments involving quantitation. For growth and bacterial burden, Student's t-tests were performed to compute differences between parental and Syn-LAB strains, and errors bars calculated from standard deviation(s). For in vivo studies, Kaplan-Meier survival curves were computed followed by Log-Rank tests for post-hoc analyses.

The results of the experiments are now described.

Example 1: Construction of *C. difficile* SlpA Chimera-Containing Vector

Figure 2A:
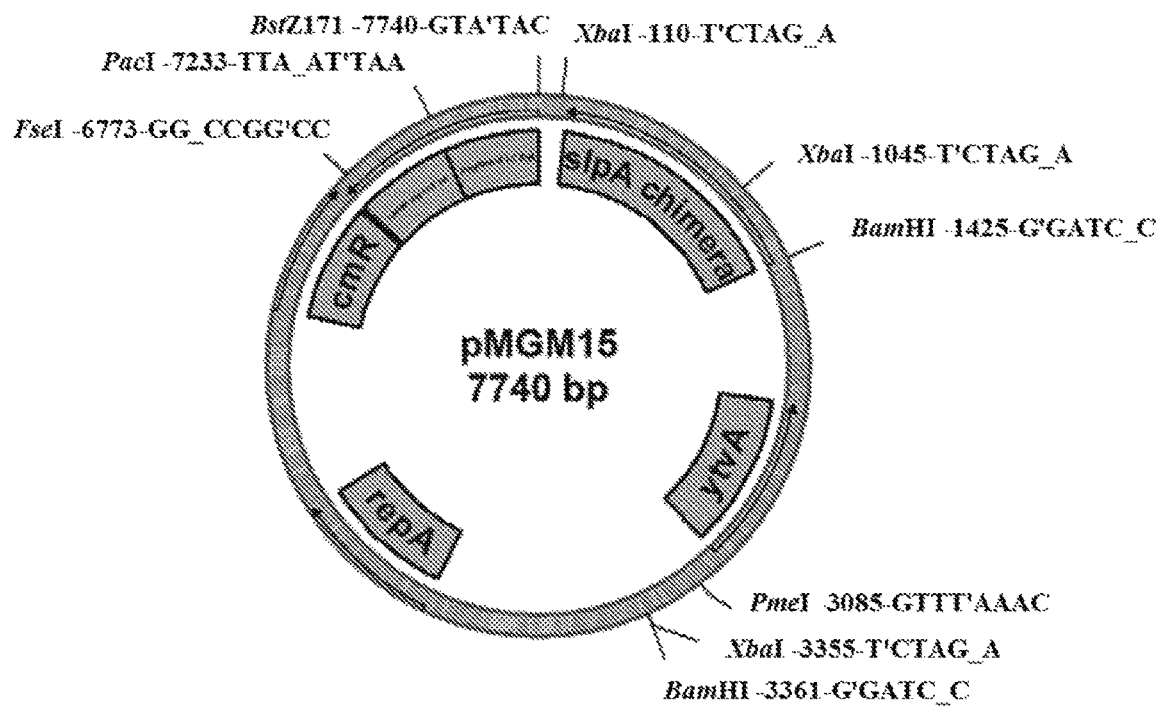
FIGS. 2A-2B are series of drawings illustrating the map of SlpA-chimera-expressing plasmid (pMGM15).
Figure 2B:
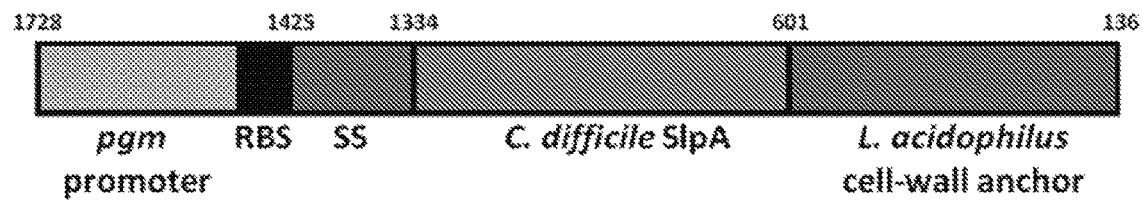
Figures 4A, 4B:
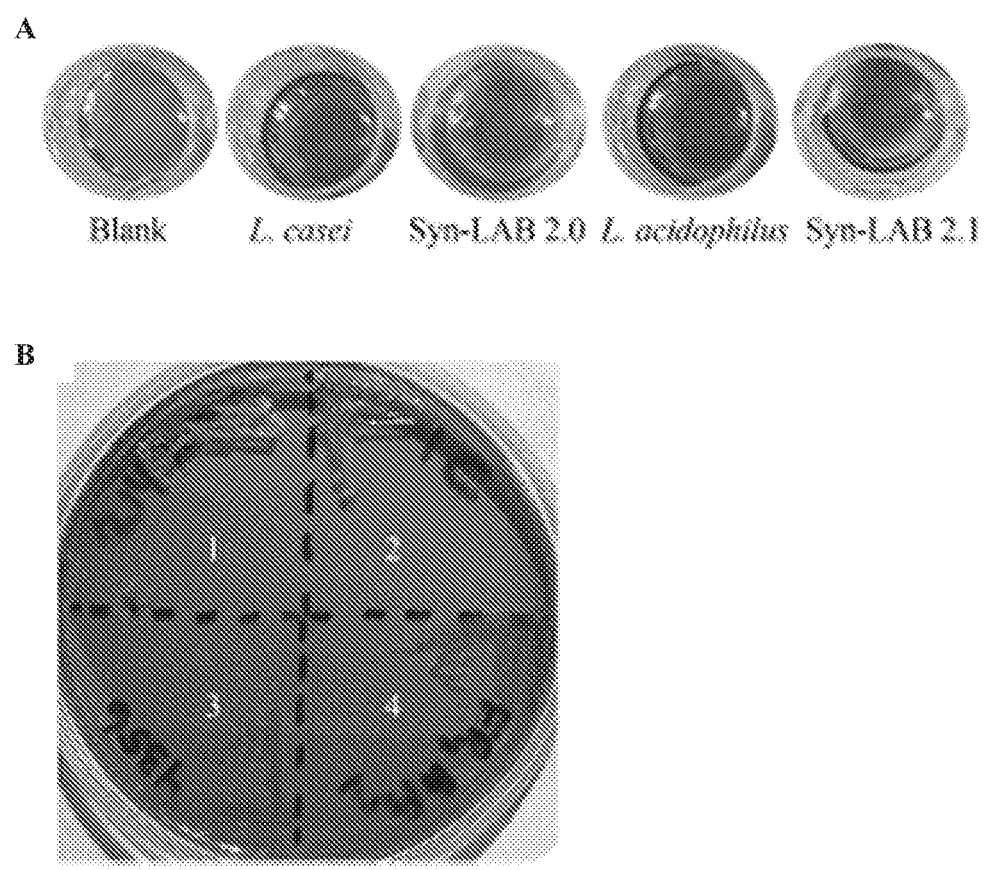
FIG. 4A is a photograph depicting Syn-LABs L Syn-LAB strain confirmation via differential growth on mannitol-MRS broth.
FIG. 4B shows Syn-LAB strain confirmation via differential growth on mMRS-BPB agar: (1) *L. casei* parent strain; (2) Syn-LAB 2.0; (3) *L. acidophilus* parent strain; (4) Syn-LAB 2.1.
Figure 5:
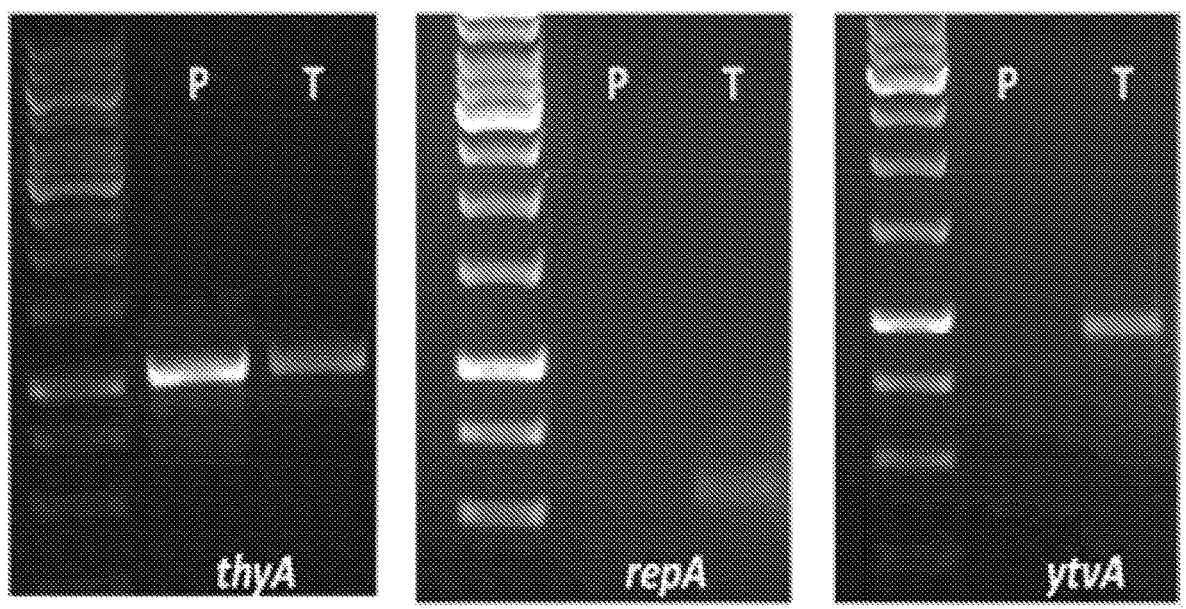
FIG. 5 is a series of images depicting Syn-LABs *L. acidophilus*-based (left; Syn-LAB 2.1) & *L. casei*-based (right; Syn-LAB 2.0) strains confirmation by PCR. P=Parent; T=Transformant. These gel images are representative examples illustrating PCR results for Syn-LAB 2.0. Identical results were obtained with Syn-LAB 2.1.
Figures 7A, 7B, 7C, 7D, 7E, 7F:
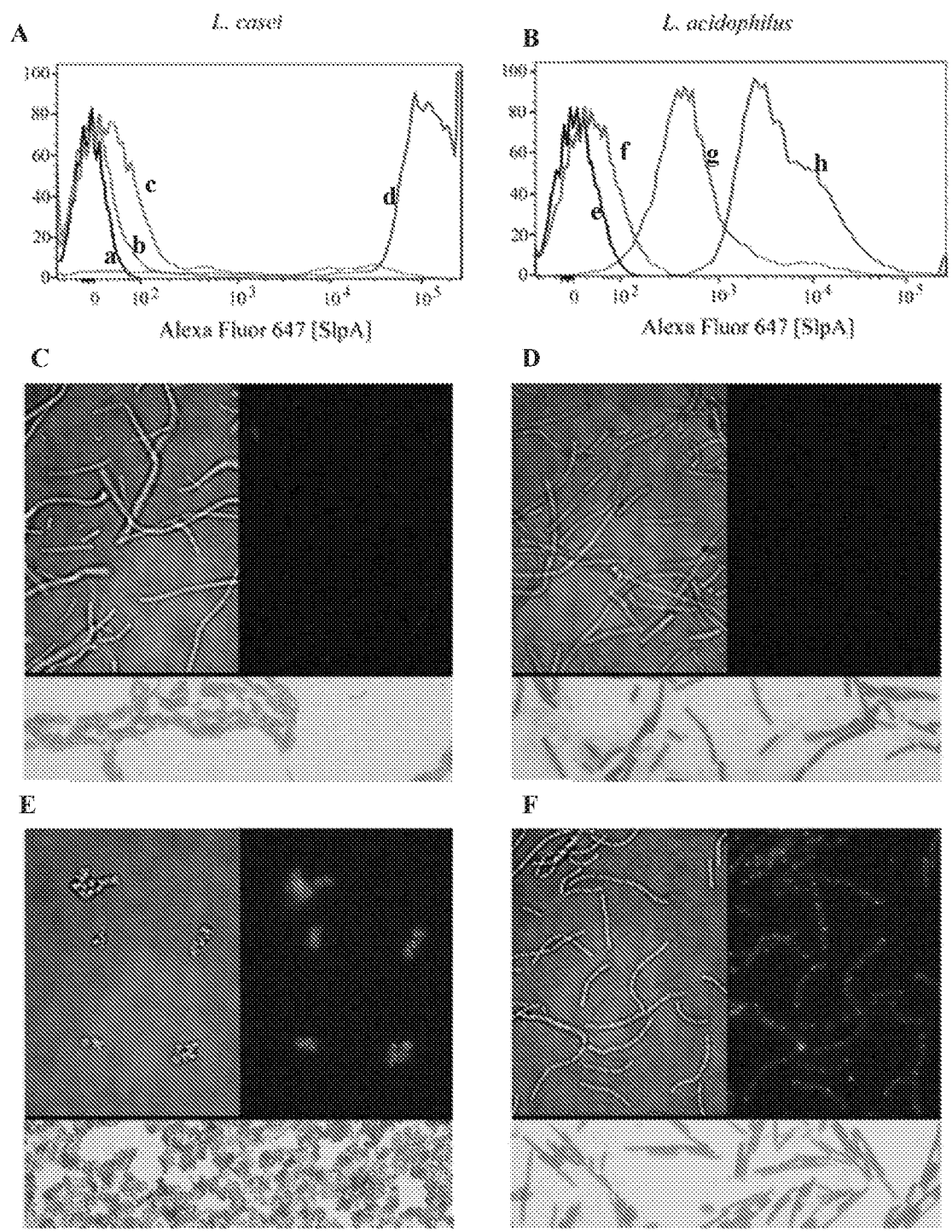
FIGS. 7A-7F show Syn-LAB 2.0 and Syn-LAB 2.1 surface-display chimeric SlpA.
Figure 8:
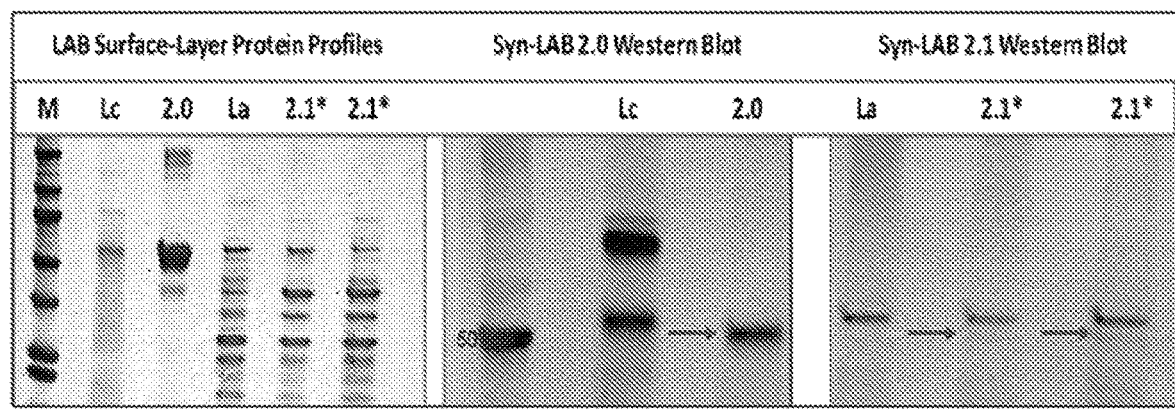
FIG. 8 is a series of images demonstrating that chimeric *C. difficile* SlpA is incorporated into the lactic acid bacterial cell wall. Left Panel, sheared total Surface-Layer Proteins (SLP) from the *L. casei* parent strain (Lc) or *L. casei*-based Syn-LAB 2.0; the *L. acidophilus* parent strain (La), or two independently-isolated clones (asterisks) of the *L. acidophilus*-based Syn-LAB 2.1. Middle and right Panels, immunoblots probing the total Surface Layer Proteins of parents and Syn-LAB strains with an antiserum specific to *C. difficile* SlpA. Red arrows point to unique, expected-size bands present only in Syn-LAB 2.0 and Syn-LAB 2.1. Non-specific bands are also detected in the immunoblots due to the antiserum being polyclonal.

A 7740 base pair (bp) dual-use vector (pMGM15, SEQ ID NO:1) was chemically synthesized in fragments, and ligated via appropriate restriction enzyme-based biology (See FIG. 1 and FIGS. 2A-2B). The pMGM15 vector has the following features:

a) slpA *L. acidophilus/C. difficile* chimera: bp135-bp1424 (SEQ ID NO: 2).

b) Constitutive promoter from *L. acidophilus* phosphoglycerate mutase (pgm) gene: bp1448-bp1728 (Duong et al, Microbial Biotech 2010); (SEQ ID NO: 3).

c) ytvA fluorescent allele of ytvA from *B. subtilis*: bp2119-bp2937; (SEQ ID NO: 4)

d) Temperature sensitive repA gene: bp4415-bp5113; (SEQ ID NO: 5).

e) Chloramphenicol resistance cat gene: bp6067-bp6690; (SEQ ID NO: 6).

f) Internal fragment of *L. acidophilus* thyA (to facilitate Campbell integration): bp6895-7236; (SEQ ID NO: 7).

g) Internal fragment of *L. casei* thyA (to facilitate Campbell integration): bp7238-bp7738; (SEQ ID NO: 8).

The precise engineering of this entire 7740 base pair vector was confirmed by complete DNA sequencing.

Example 2: Generation of Syn-LAB 2.0 (*L. casei*-Based) and Syn-LAB 2.1 (*L. acidophilus*-Based) Biologics

*L. casei* (ATCC strain 334) and *L. acidophilus* (ATCC strain 4356) were tested for purity, confirmed to be the appropriate recipients for Syn-LAB construction via 16S-based speciating PCR, and transformed with the dual use vector PMGM15 (See FIG. 1 and FIG. 2). Specifically, the surface protein layer was stripped using a modified protoplasting procedure that maintained osmoprotection, electroporated with 10 μg plasmid DNA, followed by extended recovery on selective media. All transformants were recovered at the permissive temperature (30° C.) where the repA gene is still functional, confirmed by biochemical tests and selective plating (Mann-Rogosa-Sharp agar with yeast extract+peptone+bromophenol blue; FIG. 4B), and further confirmed by multiple PCR tests (FIG. 5). Finally, transformants were propagated at the non-permissive temperature (37° C.) that forces chromosomal integration. A total of 3 independently-isolated Syn-LAB 2.0 (*L. casei*-based) and 17 independently-isolated Syn-LAB 2.1 (*L. acidophilus*-based) strains were obtained, confirmed via PCR and biobanked. Of these 1 strain each of Syn-LAB 2.0 and Syn-LAB 2.1 were used for all the studies presented herein unless indicated otherwise.

Example 3: Syn-LAB 2.0 and Syn-LAB 2.1 Display Chimeric *C. difficile* SlpA on their Cell Surface(s)

SlpA chimera expression was assessed via multiple methodologies for both engineered synthetic biologics. First, fluorescence-activated cell sorting (FACS) was used to determine the degree of heterologous SlpA surface display. In actively growing cultures, almost 100% of bacteria displayed *C. difficile* SlpA (confirmed by fluorescence shifts in both Syn-LAB 2.0 and Syn-LAB 2.1 compared to the parent strains; FIG. 6). Second, immunofluorescence was performed on the same broth cultures as above to visualize chimeric SlpA display on the surface of Syn-LAB 2.0 and Syn-LAB 2.1. A specific anti-*C. difficile* SlpA antiserum (which was raised against the *C. difficile* strain 630 SlpA) was used. To generate this antiserum, SlpA was purified from *C. difficile* strain 630 by surface shearing (Merrigan et al., PLoS ONE 8, e78404 (2013)), followed by preparative electrophoresis, extraction of the SlpA band, dialysis-based purification and injection into rabbits (immunizations and antiserum generation done via commercial vendor). The un-manipulated parent strains were used as controls. *C. difficile* specific SlpA was clearly evident as dense and uniform staining over the entire LAB surface (FIG. 7).

Example 4: Chimeric *C. difficile* SlpA is Incorporated into the Lactic Acid Bacterial Cell Surface

*C. difficile*-specific SlpA visualization was confirmed to be due to the chimeric protein being incorporated into the lactic acid bacterial cell wall (FIG. 7). Thus, total Surface-Layer proteins was sheared from Syn-LAB 2.0 and Syn-LAB 2.1 as described previously (Chu et al, PLoS Pathogens 2016), and subjected them to agarose gel electrophoresis, followed by immunoblotting. In both biologics, the *C. difficile*-origin SlpA was clearly incorporated into the lactic acid bacterium's Surface Layer (FIG. 8; left), and detectable as a discrete, correctly-sized band upon immunoblotting with *C. difficile*-specific anti-SlpA serum (FIG. 8, middle and right).

Figures 9A, 9B:
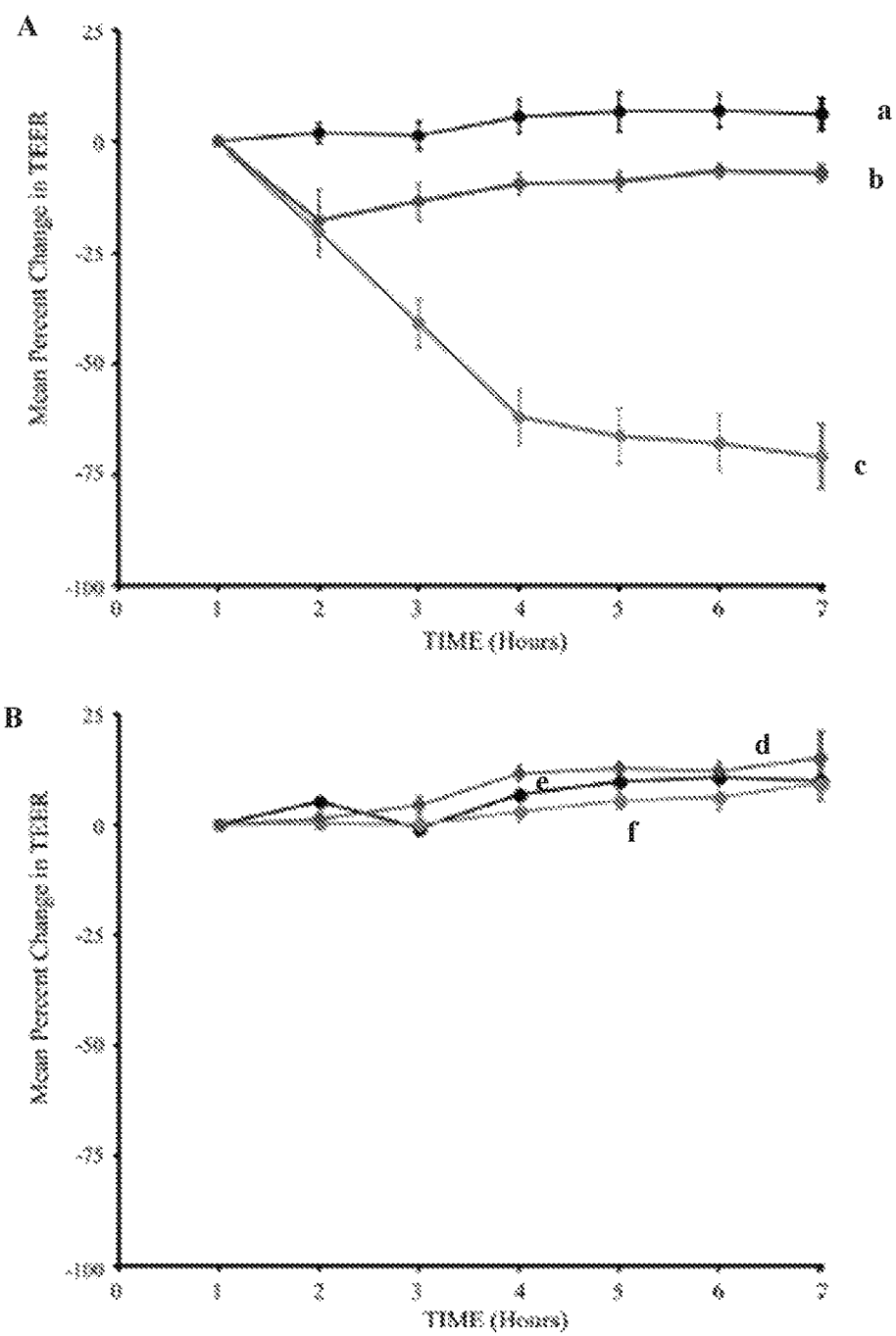
FIGS. 9A and 9B show that Syn-LAB 2.0 protects barrier function of human intestinal epithelial cells. Transepithelial electrical resistance (TEER) measurements of $C2_{BBe}$ monolayers that were mock-treated (a & e), exposed to the parent *L. casei* strain (b), or Syn-LAB 2.0 (c), or parent *L. aci*-

Example 5: Chimeric SlpA Expression in Syn-LAB 2.0 Protects Epithelial Barrier Function Syn-LAB biologics are expected to colonize the mammalian intestine, at least transiently, and likely for longer durations if persistently dosed. To assess any impact on intestinal epithelial cell health and function, a series of studies were performed. First, and to address Syn-LAB's impact on intestinal epithelial barrier function (which is greatly compromised during *C. difficile* infection), sensitive trans-epithelial electrical resistance flux measurements were performed. In these experiments, confluent human intestinal epithelial cells are grown in a polarized, tightly-organized monolayer such that they exhibit all hallmarks of the healthy gut, including apical and basal faces, and vectorized, or directional, transport of nutrients and solutes. Bacteria are then added to the apical layer, if they perturb the tight para-cellular junctional framework (barrier), electrical resistance is offered by the barrier is lost. This loss of resistance is measured using a sensitive voltmeter, and over time, and provides an indication of the robustness of the gut epithelium. Diarrhea normally occurs when barrier functions is lost, resulting in abnormal fluid transport. Addition of the parent *L. casei* strain at 100 bacteria/host cell (standard protocol; Wilbur et al., Infection and Immunity, 2015) perturbed barrier over time, and starting as early as 3 hours post-treatment. Interestingly, however, application of Syn-LAB 2.0 protected epithelial cells from any loss of barrier function. Indeed, electrical resistance measurements mimicked, and were statistically indistinguishable, from those observed for un-treated monolayers (FIGS. 9A and 9B).

Example 6: Syn-LAB 2.0 is More Protective to Host Cells than its Parent Strain

To further assess the impact of prolonged Syn-LAB contact with the host epithelial surface, an in vitro surrogate assay was used to detect host cell death in the presence of the biologic. Human intestinal epithelial cells were grown to confluence, and either mock-treated, or treated with Syn-LAB 2.0, or its parent, for up to 8 hours. Cell death was continuously measured during the treatment by Propidium Iodide (PI) uptake, which stains fragmenting DNA in dead cells, allowing for automated fluorometric measurement. At the end of an 8-hour application, Syn-LAB-treated host cells displayed cell death indistinguishable from mock-treated cells. However, host cells treated with the lactic acid bacterial parent displayed a trend toward increased cell death after 6.5 hours of treatment (FIGS. 10A and 10B).

Example 7: Syn-LAB 2.0 is Safe and Tolerable for Golden Syrian Hamsters, and Robustly Colonizes the Hamster Gastrointestinal Tract (GIT)

All animal studies were performed in accordance with an approved IACUC protocol (14-526; Vedantam PI). Syn-LAB 2.0 was prepared for in vivo dosing ($10^{8-10}$ bacteria per 200 µL volume per day). Golden Syrian hamsters (6-8 weeks old, 90-110 g weight) were divided into three groups. Group 1 animals received no treatment (control). Group 2 animals received one single dose of the broad-spectrum antibiotic Clindamycin (prescription solution; oral suspension; 30 mg/kg), followed by once-daily dosing of Syn-LAB 2.0 (antibiotic "pre-treatment" group). Group 3 animals received 4 days of Syn-LAB 2.0, followed by one single dose of oral Clindamycin (as above), followed by another 4 days of Syn-LAB 2.0 (antibiotic "mid-cycle treatment" group). Standard hamster chow and water were provided ad libitum. Fecal pellets and weights were collected daily, and pellets were re-suspended in PBS, homogenized, serially diluted and plated on Syn-LAB 2.0 selective medium. In all groups, all animals were devoid of any lactic acid bacterial colonization prior to the start of the study. Groups 2 and 3 animals started shedding Syn-LAB 2.0 on Day 1 post-administration; this continued until the end of the study on Day 8. Group 3 animals that received Clindamycin on Day 4 post-Syn-LAB showed no evidence of the biologic on Day 5, confirming the in vivo susceptibility of Syn-LAB 2.0 to standard antimicrobial therapy (also relevant to biological containment). However, when Syn-LAB feeding was resumed, shedding was also resumed in similar numbers to those observed prior to antimicrobial therapy (representative example shown in FIG. 11).

Importantly, all animals were similarly colonized, with Syn-LAB 2.0 fecal titers reaching, or exceeding $10^5$ colony forming units/gram stool on Day 3 post-treatment (FIG. 12A). Finally, Syn-LAB 2.0 was extremely palatable to all animals, as evidenced by their readiness to avidly consume the biologic with no requirement for a pre- or post-dosing sweetened electrolyte "chaser". Safety and tolerability were also confirmed via lack of any adverse effects in any Syn-LAB-treated animals, and appropriate activity and alertness throughout the study (FIG. 13).

Example 8: Immunofluorescence Studies of Colonic Tissues Harvested Post-Necropsy Immunofluorescence studies of colonic tissues harvested post-necropsy revealed dense luminal staining only from Syn-LAB 2.0 treated hamsters (FIG. 12B, right panel) as compared with mock-treated animals (FIG. 12B, left panel), confirming *C. difficile* SlpA expression in the hamster gastrointestinal tract. Finally, Syn-LAB 2.0 was avidly consumed by all hamsters, with no requirement for a pre- or post-dosing sweetened electrolyte "chaser". Safety and tolerability were also confirmed via lack of any adverse effects in any Syn-LAB-treated hamsters, as well as appropriate activity and alertness throughout the study.

Example 9: Continuous Syn-LAB Administration Induces an Anti-*C. difficile* SlpA Immune Response While the primary goal was to design biologic agents that could competitively occupy *C. difficile* attachment sites in the gut, we also explored the possibility of an anti-SlpA immune response following long-term Syn-LAB administration. Golden Syrian hamsters were continuously administered Syn-LAB 2.0 as a once-daily $10^8$ CFU dose for 55 days. Hamsters shed the biologic consistently throughout the process confirming that they were appropriately colonized. Age- and weight-matched control hamsters received no treatment. At the end of the study, hamsters were humanely euthanized, whole blood collected, and immunoblot-based analyses performed to assess anti-Syn-LAB immune response. Serum from Syn-LAB 2.0-treated hamsters (FIG. 14A, top right panel), but not from mock-treated animals (FIG. 14A, top left panel), detected *C. difficile* strain 630 SlpA in a dose-dependent manner. Presence of Slp proteins in the corresponding membranes was verified by re-probing the blots with a SlpA-specific antiserum previously generated in our laboratory (FIG. 14A, lower panels). Finally, the same experiments were performed using Slp preparations from clinically-relevant isolates of diverse *C. difficile* ribotypes (012, 017, 020, 027, 078). Reactivity was observed only when serum from Syn-LAB-treated hamsters was used (FIG. 14B). This suggested that the Syn-LAB SlpA moiety elicited a cross-reactive immune response (recognition of non-cognate *C. difficile* SlpA).

Example 10: Syn-LABs Protect Syrian Golden Hamsters from *C. difficile*-Induced Death Since single-species probiotics are thought to have limited ability to protect against CDI (Wullt et al, Scand J Infect Dis 35(6-7), 365-367(2003); Vernaya et al., JBI Database System Rev Implement Rep 15(1), 140-164(2017)) we used a combination of Syn-LAB 2.0 and Syn-LAB 2.1 in hamster protection studies. A mixed culture of the biologics ($10^8$ CFU total) was administered to antibiotic-sensitized Golden Syrian hamsters either as a fixed dose (FD) formulation (6 doses) or as a continuous dose (CD) formulation (3 days prior to clindamycin until the end of the study). Syn-LAB-treated hamsters were compared to those receiving *C. difficile* alone, or those administered LAB containing the empty vector. Challenge studies used a high inoculum (~1000 spores) of *C. difficile* strain 630 [a virulent, outbreak-associated isolate ((Merrigan et al., PLoS ONE 8, e78404 (2013)).

Fixed dosing of the Syn-LAB combination significantly delayed death of hamsters compared to mock-treated animals, as well as those administered the empty-vector-harboring strains (FIG. 15A). Continuous administration of Syn-LABs afforded statistically significant protection against CDI throughout the course of 12 days of infection (FIG. 15B). Specifically, and as compared with untreated hamsters, protection was highly significant at multiple time points during the infection course ($p=0.0091$, $p=0.0014$, $p=0.0005$, $p=0.0005$ at 6, 8, 11 and 12 days post-infection respectively). This was in contrast to the protection afforded when hamsters were administered the parent LAB strain harboring the empty vector ($p=0.1147$, $p=0.0147$, $p=0.0147$, $p=0.0147$ on Days 6, 8, 11 and 12 post infection respectively; 99% confidence interval for significance). Additionally, parent strain-treated hamsters succumbed to disease earlier in the infectious course, and were more often found moribund, with symptoms consistent with fulminant CDI (profound wet-tail, lethargy, sternal recumbency and cecal hemorrhage).

Re-administration of clindamycin to Syn-LAB-treated, *C. difficile*-challenged hamsters 14 days post infection did not result in disease or mortality (not shown). This suggested that Syn-LAB-mediated colonization resistance also ablated *C. difficile* persistence. Taken together, Syn-LAB administration was highly protective in the hamster model described above.

Example 11: Fixed-Dose Syn-LAB Administration Protects Neonatal Piglets from *C. difficile*-Induced Diarrhea Preliminary neonatal piglet studies used healthy, newborn animals treated with vancomycin on Day 4 post-farrowing to ensure elimination of any carryover *C. difficile* bacteria from the farm. Control piglets were given PBS followed by *C. difficile* challenge, whereas treated piglets were administered three $10^8$ CFU doses of the fast-growing Syn-LAB 2.1 strain over 24 hours. Syn-LAB 2.1 was detected as early as 24 hours after the first dose, and shedding continued until the end of the study (not shown).

In this model, *C. difficile* infection [1000 spores for piglets (Steele et al, (2010). J Infect Dis 201(3), 428-434), resulted in profuse diarrhea (FIG. 16A, left panel, stool score of 1). Diarrheic symptoms in these piglets continued unabated for at least 3 days, at which time the accumulated dehydration and inappetance criteria necessitated euthanasia. Microscopic examination of colonic tissues from infected piglets revealed gross hemorrhage with an abundance of inflammatory infiltrates (FIG. 16B, middle panel). However, piglets that received a one-day administration of Syn-LAB 2.1 had well-formed stool (Stool score of 3-4; FIG. 16A, right panel), as well as normal activity and appetite. Colonic tissue from these animals showed markedly less hemorrhage and inflammatory damage compared to those from piglets with *C. difficile* infection alone (FIG. 16B, right panel).

Example 12: Major Findings of this Invention

This invention provides novel engineered synthetic biologics Syn-LAB 2.0 (*L. casei*-based), and Syn-LAB 2.1 (*L. acidophilus*-based) which incorporate comprehensive biological containment features including (1) suicide-competent repA alleles that force chimeric SlpA integration into the genome obviating the requirement for any antibiotic selection; and (2) short-term GI tract viability via irreversible nucleoside auxotrophy. These biologics target a CDC "Urgent Category" pathogen (*C. difficile*), focus on a non-traditional therapeutics that avoids the use of antibiotics, and are rooted in a "bedside-to-bench-to-bedside" paradigm. Importantly, three mechanisms which have been proposed as being crucial to *C. difficile* infection prevention are all hallmarks of Syn-LAB 2.0 and Syn-LAB 2.1, namely (1) provision of robust colonization resistance, (2) potential for adaptive immune response to SlpA, an essential CD antigen, and (3) accelerated endogenous microbiota recovery via use of a safe non-antibiotic intervention (thereby reducing risk of CDI relapse).

Example 13: Important Consideration of Syn-LAB Use

Appropriate Syn-LAB 2.0 and Syn-LAB 2.1 dosing may confer the advantage of long-term protection against CD colonization by inducing an anti-SlpA immune response. LAB, especially *L. casei*, induce both mucosal and system immune response(s) (Campos et al, Microbes Infect 10, 481-488 (2008)). CD SlpA avidly binds to the surface epithelium and exposed lamina propria in GI tissues (Calabi et al, Infect Immun 70, 5770-5778 (2002)). The specific subunit used herein has also been shown to be antigenic, reacting with sera from CDI patients (Spigaglia et al, J Med Microbiol 60, 1168-1173 (2011)). Importantly, an anti-SlpA response is expected to be sustained across diverse CD molecular types since the construct of this invention was specifically engineered to encode a highly-conserved SlpA domain. Further, SlpA itself is essential; therefore, escape mutants are unlikely. Previous studies on immunization with CD surface-layer proteins (SLPs) included mixtures of multiple SLP antigens (>15), yielding inconsistent results in CDI prevention. The approach followed here, based only on SlpA, the most adherent CD SLP (Ni Eidhin et al, FEMS Immunol Med Microbiol 52, 207-218 (2008); Pechine et al, FEMS Immunol Med Microbiol 63, 73-81 (2011)), is more likely to prove immunologically robust.

Example 14: Summary

Syn-LAB 2.0 and Syn-LAB 2.1 are synthetic biologic agents wherein the lactic acid bacteria *Lactobacillus casei* and *Lactobacillus acidophilus*, respectively, have been engineered to stably and constitutively express the major *Clostridium difficile* adhesin SlpA on their cell-surface. Both agents harbor suicide plasmids expressing a codon optimized chimera of the lactic acid bacterium's cell-wall anchoring surface-protein domain, fused to the conserved, highly-adherent, host-cell-binding domain of *Clostridium difficile* Surface-Layer Protein A (SlpA; the major adhesin). Both agents also contain built-in and engineered biocontrol, in that (1) the plasmid is lost at body temperature unless stably integrated into the chromosome, obviating the need for any antibiotic selection; and (2) the whole strain is lost within a few days at body temperature due to an engineered nucleoside auxotrophy. Both agents also contain a fluorescent, non-toxic allele (ytvA) that allows for selection of the agent under blue-light visualization, and is thus an easy surrogate for in vitro or in vivo detection. Syn-LAB 2.0 and Syn-LAB 2.1 both possess positive biophysical and in vivo properties compared with their lactic acid bacterial antecedents: (1) they both adhere robustly to human intestinal epithelial cells in vitro; and (2) they both strongly and constitutively display the SlpA chimera on their cell surface(s). In addition, Syn-LAB 2.0 also (3) protects human intestinal epithelial barrier function in vitro; (4) is safe, tolerable and palatable to Golden Syrian hamsters at high daily doses; and (5) is detectable in hamster feces within 24 hours of dosing, indicating robust colonization. Most importantly, Syn-LAB 2.0 is rapidly lost from the hamster GI tract unless continuously dosed, or upon antibiotic administration, suggesting that the presently engineered bio-containment is fully functional.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

---

What is claimed is:

1. A chimeric nucleic acid molecule comprising a nucleic acid sequence comprising a phosphoglycerate mutase (pgm) constitutive promoter (pgm promoter) operatively linked to a nucleic acid sequence encoding a chimeric bacterial surface layer protein A (SlpA) comprising a *Clostridium difficile* variable domain having at least 85% identity to a *Clostridium difficile* variable domain having the sequence corresponding to SEQ ID NO:15 and a lactic acid bacterium (LAB) peptidoglycan anchor having at least 85% identity to a LAB peptidoglycan anchor having the sequence corresponding to SEQ ID NO:14.

2. The chimeric nucleic acid molecule of claim 1, wherein the pgm is from a *Lactobacillus* species selected from the group consisting of *Lactobacillus acidophilus* and *Lactobacillus casei*.

3. The chimeric nucleic acid molecule of claim 1, wherein the LAB is *Lactobacillus* species selected from the group consisting of *Lactobacillus acidophilus* and *Lactobacillus casei*.

4. The chimeric nucleic acid molecule of claim 1, wherein the nucleic acid sequence comprising the pgm promoter and the nucleic acid sequence encoding the chimeric bacterial SlpA has the nucleic acid sequence of SEQ ID NO: 18.

5. A method of treating or preventing *Clostridium difficile* infection in a mammal, the method comprising administering to the mammal an engineered cell comprising the chimeric nucleic acid molecule of claim 1, thereby treating or preventing *Clostridium difficile* infection in the mammal.

6. The method of claim 5, wherein the administered engineered cell is selected from the group consisting of *Lactobacillus acidophilus*, and *Lactobacillus casei*.

7. The method of claim 5, wherein the engineered cell is administered orally.

8. The method of claim 5, wherein the engineered cell is administered daily.

9. The method of claim 5, wherein the mammal is a human.

* * * * *